US009408902B2

(12) United States Patent
Bogoch et al.

(10) Patent No.: US 9,408,902 B2
(45) Date of Patent: Aug. 9, 2016

(54) SYNTHETIC REPLIKIN PEPTIDES AGAINST PATHOGENIC INFECTION OF INVERTEBRATES IN AQUACULTURE

(76) Inventors: Samuel Bogoch, New York, NY (US); Elenore S. Bogoch, New York, NY (US); Samuel Winston Bogoch, Oakland, CA (US); Anne Elenore Borsanyi, Brookline, MA (US)

( * ) Notice: Subject to any disclaimer, the term of this patent is extended or adjusted under 35 U.S.C. 154(b) by 1280 days.

(21) Appl. No.: 12/108,458

(22) Filed: Apr. 23, 2008

(65) Prior Publication Data
US 2009/0041795 A1 Feb. 12, 2009

Related U.S. Application Data

(63) Continuation-in-part of application No. 11/755,597, filed on May 30, 2007, now abandoned, and a continuation-in-part of application No. 11/923,559, filed on Oct. 24, 2007, now Pat. No. 8,050,871, and a continuation-in-part of application No. 12/010,027, filed on Jan. 18, 2008.

(60) Provisional application No. 60/594,743, filed on Aug. 8, 2007, provisional application No. 60/935,499, filed on Aug. 16, 2007, provisional application No. 60/935,816, filed on Aug. 31, 2007, provisional application No. 60/982,338, filed on Oct. 24, 2007, provisional application No. 60/982,333, filed on Oct. 24, 2007, provisional application No. 60/982,336, filed on Oct. 24, 2007, provisional application No. 60/991,676, filed on Nov. 30, 2007.

(51) Int. Cl.
*A61K 39/12* (2006.01)
*A61K 39/125* (2006.01)
*C07K 14/72* (2006.01)
*C07K 14/005* (2006.01)
*A61K 39/00* (2006.01)

(52) U.S. Cl.
CPC .............. *A61K 39/125* (2013.01); *A61K 39/12* (2013.01); *C07K 14/005* (2013.01); *C07K 14/72* (2013.01); *A61K 39/00* (2013.01); *A61K 2039/542* (2013.01); *A61K 2039/552* (2013.01); *C12N 2710/18022* (2013.01); *C12N 2760/16022* (2013.01); *C12N 2770/24122* (2013.01); *C12N 2770/32022* (2013.01); *C12N 2770/32034* (2013.01)

(58) Field of Classification Search
None
See application file for complete search history.

(56) References Cited

U.S. PATENT DOCUMENTS 4,132,769 A 1/1979 Osther
5,104,854 A 4/1992 Schlesinger
5,231,167 A 7/1993 Zanetti
5,280,113 A 1/1994 Rademacher
5,679,352 A 10/1997 Chong
5,866,690 A 2/1999 Bogoch
6,023,659 A 2/2000 Seilhamer
6,070,126 A 5/2000 Kokolus
6,090,406 A 7/2000 Popescu
6,242,578 B1 6/2001 Bogoch
6,256,647 B1 7/2001 Toh
6,470,277 B1 10/2002 Chin
6,484,166 B1 11/2002 Maynard
6,638,505 B2 10/2003 Bogoch
7,176,275 B2 2/2007 Bogoch et al.
7,189,800 B2 3/2007 Bogoch et al.
7,267,942 B2 9/2007 Peiris
7,420,028 B2 9/2008 Bogoch et al.
7,442,761 B2 10/2008 Bogoch et al.
7,452,963 B2 11/2008 Bogoch et al.
7,674,880 B2 3/2010 Bogoch et al.
7,705,129 B2 4/2010 Bogoch et al.
7,758,863 B2 7/2010 Bogoch et al.
7,763,705 B2 7/2010 Bogoch et al.
7,774,144 B2 8/2010 Bogoch et al.
7,894,999 B2 2/2011 Bogoch et al.
8,050,871 B2 11/2011 Bogoch et al.
8,417,462 B2 4/2013 Bogoch
8,494,781 B2 7/2013 Bogoch
2002/0120106 A1 8/2002 Bogoch
2002/0151677 A1 10/2002 Bogoch
2003/0180328 A1 9/2003 Bogoch
2003/0194414 A1 10/2003 Bogoch
2003/0195874 A1 10/2003 Akaboshi
2005/0129715 A1 6/2005 Paterson et al.
2005/0202415 A1 9/2005 Bogoch
2005/0271676 A1 12/2005 Sette (Continued)

FOREIGN PATENT DOCUMENTS

DE 3628658 3/1988
EP 0 108 564 A1 5/1984

(Continued)

OTHER PUBLICATIONS

US Marine Shrimp Farming Program Flyer, 2 pages, no date available.*

(Continued)

Primary Examiner — Shanon A Foley
Assistant Examiner — Myron Hill
(74) Attorney, Agent, or Firm — Daren P. Nicholson

(57) ABSTRACT

The present invention provides isolated or synthesized peptides of about 7 to about 50 amino acids identified in the genome of pathogens in invertebrates in aquaculture for prevention and treatment of outbreaks of these pathogens in aquaculture and methods of preventing and treating pathogenic outbreaks using the identified peptides.

17 Claims, 12 Drawing Sheets

(56) References Cited

U.S. PATENT DOCUMENTS

| | | |
|---|---|---|
| 2006/0024669 A1 | 2/2006 | Bogoch |
| 2007/0026009 A1 | 2/2007 | Bogoch |
| 2007/0128217 A1 | 6/2007 | ter Meulen et al. |
| 2008/0176217 A1 | 7/2008 | Bogoch et al. |
| 2008/0241918 A1 | 10/2008 | Sasisekharan et al. |
| 2008/0260764 A1 | 10/2008 | Bogoch et al. |
| 2009/0017052 A1 | 1/2009 | Bogoch et al. |

FOREIGN PATENT DOCUMENTS

| | | |
|---|---|---|
| IT | 98MI0874 | 10/1999 |
| JP | 3-503166 T | 7/1991 |
| JP | 8-287088 | 11/1996 |
| JP | 9121867 | 5/1997 |
| JP | 10-212300 A | 8/1998 |
| JP | 11001493 | 1/1999 |
| JP | 2000-253876 A | 9/2000 |
| KR | 10-1999-0008052 | 1/1999 |
| WO | 8907112 A1 | 10/1989 |
| WO | 96/32106 | 10/1996 |
| WO | 96/036436 | 11/1996 |
| WO | 0018351 | 4/2000 |
| WO | 00/52054 | 9/2000 |
| WO | 0104135 A2 | 1/2001 |
| WO | 02085093 A2 | 10/2002 |
| WO | 03005880 A3 | 1/2003 |
| WO | 0383058 A2 | 10/2003 |
| WO | 200510032 A2 | 2/2005 |
| WO | 200504754 A2 | 11/2005 |
| WO | 2006/088962 | 8/2006 |
| WO | 200688962 A2 | 8/2006 |
| WO | 2007022151 A | 2/2007 |
| WO | 2007149715 A | 12/2007 |
| WO | 2008060669 A2 | 5/2008 |
| WO | 2008121329 A2 | 10/2008 |
| WO | 2008/140557 | 11/2008 |
| WO | 2008/143717 | 11/2008 |
| WO | 2008156914 | 12/2008 |

OTHER PUBLICATIONS

List of Animal Species in Aquaculture, Crustaceans, document retrieved Dec. 15, 2010 at http://www.fao.org/docrep/w2333e/W2333E04.htm.*

List of Animal Species in Aquaculture, Molluscs, document retrieved Dec. 15, 2010 at http://www.fao.org/docrep/w2333e/W2333E05.htm.*

Song et al., Fish and Shellfish Immunology 2003 vol. 14, pp. 317-331.*

Wang et al., Biochemical and Biophysical Research Communications 2004 vol. 325, pp. 899-907.*

Locker et al., Immunological Reviews 2004, vol. 198, pp. 10-24.*

Hauton et al., Bioessays vol. 29, pp. 1138-1146, 2007.*

Japan Patent Office, Office Action in related Japanese Application No. 2009-024307, dated Sep. 8, 2009 Japan.

United States Patent and Trademark Office, US Office Action in related U.S. Appl. No. 11/615,578, dated Oct. 21, 2009, US.

NCBI Swiss-Prot Locus P33795, accessed Jul. 20, 2009.

Betakova et al., "The Vaccinia Virus A14.5L Gene Encodes a Hydrophobic 53-Amino-Acid Virion Membrane Protein That Enhances Virulence in Mice and is Conserved among Vertebrate Poxviruses," Journal of Virology, vol. 74., No. 9, May 2000, p. 4085-4092.

Massung et al., "Potential virulence determinants in terminal regions of variola spallpox virus genome," Nature, vol. 366, Dec. 23-30 1993, p. 748-751.

Replikins, Ltd. Press Release, "Replikins, Ltd. has discovered a group of virus peptides that predict whether a virus is rapidly replicating and whether it is likely to spread" (Apr. 21, 2006).

Replikins, Ltd. Press Release, "Virus Replication Discovery Helps Predict Epidemics" (Apr. 24, 2006).

Hendrickson, D., Mass High Tech, "Flu forecaster firm born" (Apr. 28, 2006).

Boggs, J, Diagnostics & Imaging Week, "Replikins: Predicting global epidemics replication data" (May 4, 2006).

Replikins, Ltd. Press Release, "Replikins' FluForecast® Software Pinpoints Change in Deadly Bird Flu Amino Acid Sequence in Humans" (Jun. 3, 2006).

Replikins, Ltd. Press Release, "Advance Warning of H5N1 Influenza Outbreaks May Be Found in Shrimp Virus Reservoirs" (Oct. 26, 2006).

Replikins, Ltd. Press Release, "Rising H5N1 'Bird Flu' High-Virulence Sequences Found by Replikins, Ltd." (Nov. 6, 2006).

Replikins, Ltd. Press Release, "Human H5N1 Virus Replikin Count Overtakes Levels in H5N1 'Bird Flu'" (Dec. 27, 2006).

Replikins, Ltd. Press Release, "Gene Segment Identified in Virulent Human H5N1 Viruses—Key Discovery May Enable Development of Vaccines, Therapeutics" (Jan. 25, 2007).

Replikins, Ltd. Press Release, "High Host Mortality Rate Quantitatively Related to High Virus Replikin Count" (Mar. 6, 2007).

Replikins, Ltd. Press Release, "FluForecast® Trial in 2006 Predicted High Human H5N1 Mortality in Indonesia" (May 9, 2007).

Replikins, Ltd. Press Release, "Indonesia Reports Experiencing Human H5N1 Mortality Increase, as Predicted Last Year by Replikins' FluForecast® Quantitative Virus Analysis" (Jun. 8, 2007).

Replikins, LLC Press Release, "Replikins, LLC Finds West Nile Virus Replikin Count™ Has Reached Its Highest Recorded Value" (Aug. 3, 2007).

Replikins, LLC Press Release, "AMAS Test Measures Lethal Replikin Gene Activity in Lung and Other Cancers" (Dec. 6, 2007).

Replikins, Ltd. Press Release, "Lethal Human H5N1 Influenza Virus Replikin Gene Still Upregulated" (Dec. 11, 2007).

Replikins, Ltd. Press Release, "FluForecast® Replikin Count™ Predicts That the H5N1 Cycle Which Began in 1996 is Now Over" (Feb. 11, 2008).

Replikins, Ltd. Press Release, "Replikins Oral Vaccine Synthesized in 7 days protects 91% of Shrimp Against Lethal Virus" (Mar. 11, 2008).

Replikins, Ltd. Press Release, "H1N1 Influenza Virus with Highest Replikin Count™ Since the 1918 Pandemic Identified in the U.S. and Austria" (Apr. 7, 2008).

PCT International Search Report and Written Opinion PCT/US2009/041565, Jan. 2010, EPO, International Searching Authority, Rijswijk, NL.

PCT International Preliminary Report on Patentability, PCT/US2006/05343, Aug. 22, 2008, USPTO, International Preliminary Examining Authority, Alexandria, VA, USA.

PCT International Search Report and Written Opinion, PCT/US2007/069978, Jun. 3, 2008, EPO, International Searching Authority, Rijswijk, NL.

PCT International Search Report and Written Opinion, PCT/US2007/82436, 2009, USPTO, International Searching Authority, Alexandria, VA, USA.

PCT International Search Report and Written Opinion, PCT/US2008/00645, 2009, USPTO, International Searching Authority, Alexandria, VA, USA.

EP Office Action 04785929.3, Sep. 1, 2008, EPO, Netherlands.

NZ Office Action Jul. 16, 553983, 2008, IPO, New Zealand.

PepBank entry 42800, corresponding to UniProt database entry P15516, Apr. 1, 1990, available at http://pepbank.mgh.harvard.edu, accessed Oct. 6, 2008.

Bogoch et al. "In vitro production of the general transformation antibody related to survival in human cancer patients: antimalignin antibody," Cancer Detection and Prevention, Sep. 28, 1988, vol. 12, Nos. 1-6, pp. 313-320.

Bogoch et al., "Replikins: The Chemistry of Rapid Replication," Begell House, Inc. NY, NY (2005).

Johansson et al., "Small, novel proteins from the mistletoe Pharadendron tementosum exhibit highly selective cytotoxicity to human breast cancer cells," Cell Mol. Life Sci, Jan. 2003, 60: 165-175.

Kazazic et al., "Mutational analysis of the role of charged residues in target-cell binding, potency and specificity of the pediocin-like bacteriocin sakacin P," Microbiology, (2002) 148: 2019-27.

Patil et al., "Identification of a Talin-binding Site in the Integrin β3 Subunit Distinct from the NPLY Regulatory Motif of a Post-ligand

(56) References Cited

OTHER PUBLICATIONS

Binding Functions," The Journal of Biological Chemistry, vol. 274, No. 1, Oct. 1, 1999, p. 28575-28583.

Sharma et al., "Synthesis and Characterization of a Peptide Identified as a Functional element in αcrystallin," The Journal of Biological Chemistry, vol. 275, No. 6, Feb. 11, 2000, p. 3767-3771.

Witteveldt, et al., "Protection of Penaeus monodon against White Spot Syndrome Virus by oral Vaccination," Journal of Virology, Feb. 2004, p. 2057-2061 vol. 78, No. 4, entire document, esp. p. 2060, col. 1.

PCT International Search Report, PCT/US2002/09240, Jan. 14, 2004, USPTO, International Searching Authority, Washington DC.

PCT International Preliminary Examination Report, PCT/US2002/09240, Feb. 5, 2004, USPTO, International Preliminary Examination Authority, Alexandria, VA, USA.

PCT International Search Report, PCT/US2002/21494, May 30, 2003, USPTO, International Searching Authority, Washington DC.

PCT International Preliminary Examination Report, PCT/US2002/21494, Nov. 26, 2004, USPTO, International Searching Authority, Alexandria, VA, USA.

PCT International Search Report, PCT/US2003/08990, Dec. 7, 2005, International Searching Authority, USPTO, Alexandria, VA, USA.

PCT Written Opinion of the International Searching Authority, PCT/US2004/017936, Apr. 7, 2005, EPO, International Searching Authority, Munich, DE.

PCT International Search Report, PCT/US2004/017936, Apr. 28, 2005, EPO, International Searching Authority, Rijswijk, NL.

PCT International Preliminary Report on Patentability, PCT/US2004/017936, Apr. 13, 2007, USPTO, International Preliminary Examining Authority, Alexandria, VA, USA.

PCT International Search Report, PCT/US2005/014443, Oct. 21, 2005, EPO, International Searching Authority, Rijswijk, NL.

PCT Written Opinion of the International Searching Authority, PCT/US2005/014443, Apr. 12, 2006, EPO, International Searching Authority, Munich, DE.

PCT International Preliminary Report on Patentability, PCT/US2005/014443, Nov. 1, 2006, WIPO, International Bureau of WIPO, Geneva, Switzerland.

PCT International Search Report, PCT/US2006/05343, Sep. 25, 2007, USPTO, International Searching Authority, Alexandria, VA, USA.

Supplementary Partial European Search Report 99944002, Apr. 20, 2004, EPO, Munich, DE.

Supplementary Partial European Search Report 02736514.7, Mar. 9, 2006.

Supplementary Partial European Search Report 02752202.8, Mar. 10, 2006.

Supplementary Partial European Search Report 03721445.9, Dec. 12, 2006, EPO, International Searching Authority, Munich, DE.

NCBI accession # gi 75059 Jul. 16, 1999.

NCBI Listing JQ0032, May 11, 2000.

NCBI Accession # AAK38298, Apr. 19, 2001.

NCBI Accession No. NP 740460 (2000).

NCBI Blast Searching, Gene Gateway—Exploring Genes and Genetic Disorders, "Sequence similarity searching using NCBI Blast" (http:www.ORNL.gov/sciftechresources/Himan_Genome/chromosome/blast.shtml) (screenshot Apr. 27, 2005 by USPTO in U.S. Appl. No. 11/116,203).

NCBI Query Tutorial "Introduction to a Blast Query" (http://www.ncbi.nim.nih.gov/Education/BLASTinfo/tut1.html) (screenshot Apr. 27, 2005 by Uspto in U.S. Appl. No. 11/116,203).

NCBI Query Tutorial "Introduction" (http://www.ncbi.nim.nih.gov/Education/BLASTinfo/query_tutorial.html) (screenshot Apr. 27, 2005 by USPTO in U.S. Appl. No. 11/116,203, filed Apr. 28, 2005).

NCBI Query Tutorial "Setting up a Blast Search" (http://www.ncbi.nim.nih.gov/Education/BLASTinfo/Blast_setup.html) (screenshot Apr. 27, 2005 by USPTO in U.S. Appl. No. 11/116,203).

3MOTIF—Search Instructions, 3motif in three Dimensions, article titles "Submitting a protein sequence": http://brutlag.stanford.edu/3motif/search_instr.html) (screenshot Apr. 27, 2005 by USPTO in U.S. Appl. No. 11/116,203).

Abrams M. B. et al., "Early Detection and Monitoring of cancer with the Anti-Malignin Antibody Test," Cancer detection and Prevention, XX, XX, vol. 18, No. 1, 1994, pp. 65-78, XP000673180, ISSN:0361-090X.

Atassi, M. Z. et al., "A novel approach for localization of the continuous protein antigenic sites by comprehensive synthetic surface scanning: Antibody and T cell activity to several influenza hemagglutinin synthetic sites," Immunological Communications, 1984, pp. 539-551, vol. 13, No. 6, Marcel Dekker, Inc., XP009062995, ISSN: 0090-0877.

Ben-Yedidia, T. et al., "Intranasal administration of peptide vaccine protects human/mouse radiation chimera from influenza infection," International Immunology, 1999, pp. 1043-1051, XP000914818, ISSN: 0953-8178.

Bogoch et al.: In vitro production of the general transformation antibody related to survival in human cancer patients; antimalignin antibody; Abstract, Cancer Detection and Prevention, 1988, vol. 12, Nos. 1-6, pp. 313-320. (Database Medline on STN National Library of Medicine (Bethesda, MD, USA) No. 89028479.

Bogoch, S. et al., "A Checklist for Suitability of Biomarkers as Surrogate Endpoints in Chemoprevention of Breast Cancer," Journal of Cellular Biochemistry, Supplement, Boston, US, vol. 19, pp. 173-185, XP009046492, ISSN: 0733-1959, 1994.

Bogoch et al., "Aglyco Pathology of Viral Receptors in Dementias," Annals of the New York Academy of Sciences, New York Academy of Sciences, New York Academy of Sciences, New York, NY, US, vol. 757, 1995, pp. 413-417, XP008003395, ISSN:0077-8923.

Bogoch et al., "Rapid replication and Replikintm structures: basis of the AMASRTest and CAVAXR," Cancer Detection and Prevention Online, Feb. 9, 2002, XP002350483.

Brown, L. R. et al., "Recognition of the influenza hemagglutinin by Class II MHC-restricted T lymphocytes and antibodies," Journal of Immunology, Oct. 14-15, 1991, pp. 2677-2684, vol. 147, No. 8, American Association of Immunologists, USA, XP002371257, ISSN: 0022-1767.

Brumeanu, T.M. et al., "Immunogenicity of a Contiguous T-B Synthetic Epitope of the A/PR/8/34 Influenza Virus," Journal of Virology, Jul. 1997, vol. 71, No. 7, pp. 5473-5480.

Bucher, D. et al., "M protein (M1) of influenza virus antigenic analysis and intracellular localization with monoclonal antibodies", J Virol. Sep. 1989; 63(9): pp. 3622-3633.

Carr C. M. et al., "A spring-loaded mechanism for the conformational change of influenza hemagglutinin," Cell, May 21, 1993, pp. 823-832, vol. 73, Cell Press, XP002059698, ISSN: 0092-8674.

Chambers, T.M. et al., "Antigenic and molecular characterization of subtype H13 hemagglutinin of influenza virus," Database NCBI on STN, Accession No. HMIVT2, Virology, pp. 180-188, abstract, 1989, 172(1).

Gao, Identification and characterization of T helper epitopes in the nucleoprotein of influenza a virus, J. Immunol. 1989, vol. 143, pp. 3007-3014.

Gelder, C. M. et al., "Human CD4+ T-cell repertoire of response to influnza A virus hemagglutinin after recent natural infection," Journal of Virology, Dec. 1995, vol. 69, No. 12, pp. 7497-7506A.

Keppeler et al., "Elongation of thr N-acyl side chain of sialic acid in MDCK II cells inhibits influenza A virus infection," abstract, Biochemical and Biophysical Research Communications, Dec. 18, 1998, vol. 253, No. 2. Database Medline on STN, National Library of Medicine, (Bethesda, MD, USA), No. 99097253.

Kornblith P. L. et al., "Growth-inhibitory effect of diphenylhydantoin on murine astrocytomas," Neurosurgery, vol. 5, No. 2, pp. 259-63 (Aug. 1979), MEDLINE, XP002199627.

Margalit et al., "Prediction of Immunodominant Helper T Cell Antigenic Sites From the Primary Sequence," Jour. of Immunology, vol. 138, 2213-2229, Apr. 1, 1987.

Marra, M. et al., "The Genome Sequence of the Sars-Associated Coronavirus," Science, American Association for the Advancement of Science, US, v. 300, No. 5624, p. 1399-1404, XP002269483, ISSN: 0036-8075, May 30, 2003.

(56) References Cited

OTHER PUBLICATIONS

O'Donnell, F.T. et al., "Epidemiology and molecular characterization of co-circulating influenza A/H3N2 virus variants in children," Epidemiology and Infection, Jun. 2003, pp. 521-31, abstract, vol. 130, issue 3, The University of Texas-Houston School of Public Health, Houston, Texas. Database Medline U.S. National Library of Medicine (Bethesda, MD) Accession No. 2003:298060.
Orlando, C. et al., "A monoclonal antibody directed against the catalytic site of Bacillus anthracis adenylyl cyclase identifies a novel mammalian brain catalytic subunit," Biochemistry, 1992, pp. 3215-3222, vol. 31, American Chemical Society, XP002371438, ISSN: 0006-2960.
Pannifer, Crystal structure of the anthrax lethal factor, Nature, vol. 414, pp. 229-233 (Nov. 2001).
Qin, E. et al., "A Genome Sequence of Novel SARS-CoV Isolates: the Genotype, GD-INS29, Leads to a Hypothesis of Viral Transmission in South China," Genomics Proteomics & Bioinformatics, vol. 1, No. 2, p. 101-107, XP001206098, ISSN: 1672-0229, May 2003.
Rodman, Toby C. et al., "Human Immunodeficiency Virus (HIV) Tat-reactive Antibodies Present in Normal HIV-negative Sera and Depleted in HIV-positive Sera. Identification of the Epitope," vol. 175, pp. 1247-1253, (May 1992).
Rota, P. et al., "Characterization of a Novel Coronavirus Associated with Severe Acute Respiratory Syndrome," Science, American Association for the Advancement of Science, US, v. 300, No. 5624, p. 1394-1399, XP002269482, ISSN: 0036-8075, May 30, 2003.
Spackman et al., "Characterization of Low-Pathogenicity H5N1 Avian Influenza Viruses from North America," Journal of Virology, vol. 81, No. 21, Nov. 13, 2007, pp. 11612-11619.
Tompkins, S.M. et al., "Matrix protein 2 vaccination and protection against influenza viruses, including subtype H5N1," Emerging Infectious Diseases, vol. 13, No. 3, p. 426-435, Mar. 2007, available at www.cdc.gov/eid.
PCT International Preliminary Report on Patentability, PCT/US2007/069978, May 1, 2009, USPTO, International Preliminary Examining Authority, Alexandria, VA, USA.
EP Office Action 04785929.3, Feb. 2, 2009, EPO, Netherlands.
NZ Office Action 560415, Mar. 6, 2009, IPO, New Zealand.
UnitProt/Swiss-Prot database entry O89746 1 Influenza A virus (strain A/Chicken/Hong Kong/220/1997 H5N1 genotype GS/GD) Nov. 1, 1998.
PCT Invitation to Pay Additional Fees and Communication Relating to the Results of the Partial International Search, PCT/US2009/061108, Mar. 8, 2010, EPO, Rijswijk, NL.
UnitProt A8DXX4, Journal of Virology, vol. 81, No. 21, Nov. 13, 2007, pp. 11612-11619.
Anonymous; "Other News to Note", Bioworld Today, Mar. 12, 2008, vol. 19, No. 49, ISSN: 1541-0595.
International Search Report and Written Opinion, PCT/US2008/061336, Feb. 2, 2009.
Sharma et al., "Synthesis and Characterization of a Peptide Identified as a Functional element in αA-crystallin," The Journal of Biological Chemistry, vol. 275, No. 6, Feb. 11, 2000, p. 3767-3771.
Kazazic et al., "Mutational analysis of the role of charged residues in target-cell binding, potency and specificity of the pediocin-like bacteriocin sakacin P," Microbiology, 2002, 148: 2019-27.
PepBank entry 42800, corresponding to UniProt database entry P15516, Apr. 1, 1990 (Homo sapiens salival protein histatin), available at http://pepbank.mgh.harvard.edu, accessed Oct. 6, 2008.
NZ Office Action 553983, Jul. 16, 2008, IPO, New Zealand.
PCT International Preliminary Report on Patentability, PCT/US2006/05343, Jul. 22, 2008, USPTO, International Preliminary Examining Authority, Alexandria, VA, USA.
PCT International Search Report, PCT/US2007/069978, Jun. 3, 2008, EPO, International Searching Authority, Rijswijk, NL.
PCT International Search Report and Written Opinion, PCT/US2009/061108, Jun. 11, 2010, EPO, Rijswik, NL.
US Office Action, U.S. Appl. No. 11/755,597, May 14, 2010.
AU Office Action, Application No. 2006214332, Jun. 10, 2010.
US Office Action, U.S. Appl. No. 12/010,027, Jul. 21, 2010.
SG Written Opinion, Application No. SG 200602419-4, Aug. 3, 2010.
US Office Action, U.S. Appl. No. 12/495,306, Sep. 1, 2010.
US Office Action, U.S. Appl. No. 11/755,597, Sep. 30, 2010.
NCBI Accession No. AAW59548 (Jan. 24, 2005).
NCBI Accession No. DQ100549 (Jul. 6, 2005).
GenBank Accession No. AAV74400.1 (Dec. 5, 2005).
NCBI Accession No. ABE97631 (Jun. 27, 2006).
Fern, J. "Promiscuous malaria peptide epitope stimulates CD45Ra T cells from peripheral blood of nonexposed donors," J. Immunology 1992, vol. 148, pp. 907-913.
Liu et al. Science, Aug. 19, 2005; 309 (5738); 1206. Epub Jul. 6, 2005 "Highly pathogenic H5N1 influenza virus infection in migratory birds.".
Rodriguez et al., "Plasmodium falciparum EBA-175 kDa protein peptides which bind to human red blood cells." Parasitology (2000), vol. 120, pp. 225-235.
U.S. Appl. No. 11/755,597 Response to Office Action, Nov. 30, 2010.
US Office Action, U.S. Appl. No. 12/170,763, Feb. 15, 2011.
US Office Action, U.S. Appl. No. 12/252,028, Feb. 15, 2011.
US Office Action, U.S. Appl. No. 12/495,306, Feb. 15, 2011.
US Office Action, U.S. Appl. No. 12/010,027, Feb. 16, 2011.
US Office Action, U.S. Appl. No. 12/688,372, Mar. 28, 2011.
SG Written Opinion, Application No. SG 200602420-2, Apr. 6, 2011.
US Office Action, U.S. Appl. No. 12/789,877, Jun. 8, 2011.
EP Supplemental Search, EP 10 01 2944, May 20, 2011, EPO, Munich, DE.
EP Supplemental Search, EP 10 01 2945.1, Jun. 9, 2011, EPO, Munich, DE.
US Notice of Allowance, U.S. Appl. No. 11/923,559, Jun. 23, 2011.
CA Office Action, CA 2,441,540, Jul. 11, 2011, CIPO, CA.
CN Office Action, CN 200580012974.0, Jul. 19, 2011, CIPO, CN.
JP Office Action, JP 2007-555371, Jul. 19, 2011, JPO.
EP Partial Search Report, EP 11 158 084.1, Oct. 7, 2011, EPO.
EP Partial Search Report, EP 11 158 093.2, Oct. 14, 2011, EPO.
U.S. Office Action, U.S. Appl. No. 12/688,372, Nov. 21, 2011, USPTO.
KR Office Action, KR 10-2006-7021152, Dec. 8, 2011, KIPO.
JP Office Action, JP 2007-510929, Aug. 30, 2011, JPO.
UniProt C2W513 (Jun. 16, 2009).
NCBI Accession No. NP_052803 (May 14, 1998).
ACML 01000595 database entry (May 1, 2009).
Buscaglia et al., "The repetitive domain of Trypanosoma cruzi trans-sialidase enhances the immune response against the catalytic domain," Journal of Infectious Diseases, University of Chicago Press, Chicago, IL, vol. 177, No. 2, 1 Feb. 1998, pp. 431-436.
Cross et al., "Studies on influenza haemagglutinin fusion peptide mutants generated by reverse genetics," The EMBO Journal vol. 20 No. 16 pp. 4432-4442, 2001.
Diggs et al. "Plasmodium falciparum: Passive immunization of Aotus lemurinus griselmembra with immune serum," Experimental Parasitology, vol. 80, Issue 2, Mar. 1995, pp. 291-296.
Ferro et al., "The androgen receptor CAG repeat: a modifier of carcinogenesis?" Molecular and Cellular Endocrinology, 193, Jan. 1, 2002, pp. 109-120.
Frankel et al., "Activity of synthetic peptides from the Tat protein of human immunodeficiency virus type 1," Proc. Natl. Acad. Sci.USA, Oct. 1989, vol. 86, pp. 7397-7401.
Guan et al., "Emergence of multiple genotypes of H5N1 avian influenza viruses in Hong Kong SAR," PNAS vol. 99, No. 13, Jun. 25, 2002, pp. 8950-8955.
He, Z. et al., "Identification of epitopes in cucumber mosaic virus using a phage-displayed random peptide library," J Gen Virol 1998, vol. 79, pp. 3145-3153 (accepted Aug. 21, 1998).
Kumar, et al., "Cytotoxic T Cells Specific for the Circumsporozoite Protein of Plasmodium Falciparum," Nature, vol. 334, Jul. 21, 1988, pp. 258-260, XP002027064.
Lal et al., "Identification of T-cell determinants in natural immune responses to the Plasmodium falciparum apical membrane antigen (AMA-1) in an adult population exposed to malaria," Infection and Immunity, vol. 64, No. 3, Mar. 1996, pp. 1054-1059, XP055000060.
Melville et al., "P58IPK, a novel cochaperone containing tetratricopeptide repeats and a J-domain with oncogenic potential,"

(56) References Cited

OTHER PUBLICATIONS

Database accession No. PREV200000253165; & CMLS Cellular and Molecular Life Sciences, vol. 57, No. 2, Feb. 2000, pp. 311-322, ISSN: 1420-682X.

Okuno et al., "A Common Neutralizing Epitope Conserved between the Hemagglutinins of Influenza A Virus H1 and H2 Strains," Journal of Virology, vol. 67, No. 5, May 1993, p. 2552-2558.

Ostroff, "Emerging infectious diseases 1997-1998: The role of molecular epidemiology," Memorias Do Instituto Oswaldo Cruz, vol. 94, No. 1, Jan. 1999, pp. 1-3, XP002636692.

Patarroyo et al., "Induction of protective immunity against experimental infection with malaria using synthetic peptides," Nature, vol. 328, No. 6131, Aug. 13, 1987, pp. 629-632.

Simeckova-Rosenberg et al., "Protection of mice against lethal viral infection by synthetic peptides corresponding to B- and T-cell recognition sites of influenza A hemagglutinin," Vaccine, vol. 13, No. 10, pp. 927-932 (1995).

Smith et al., "Finding sequence motifs in groups of functionally related proteins," PNAS, vol. 87, pp. 826-830, Jan. 1990.

Takahashi et al., "Antibody to Ras proteins in patients with colon cancer," Clin Cancer Res, Oct. 1995, vol. 1, pp. 1071-1077.

Wee et al., "SVM-based prediction of caspase substrate cleavage sites," BMC Bioinformatics 2006, 7(Suppl 5) S14.

Yao et al., "Linear epitopes of sperm whale myoglobin identified by polyclonal antibody screening of random peptide library," Int J Peptide Protein Res, Jun. 30, 1996, vol. 5, pp. 477-485.

Seal et al., "Elevation of Serum Protein-Bound Carbohydrates and Haptoglobin in Schizophrenia," Clinical Chemistry; Oct. 1996, vol. 12, No. 10, pp. 709-716.

Schenk, S. et al., "Four recombinant isoforms of Cor a 1, the major allergen of hazel pollen, show different reactivities with allergen-specific T-lymphocyte clones," European Journal of Biochemistry, 1994, pp. 717-722, vol. 224, XP002371408, ISSN: 0014-2956.

Shi, Immunogenicity and in vitro protective efficacy of a recombinant multistage Plasmodium falciparum candidate vaccine, PNAS vol. 96, No. 4, pp. 1615-1620.

Tanaka, T. et al., "Efficient Generation of Antibodies to Oncoproteins by using Synthetic Peptide Antigens." Proceedings of the National Academy of Sciences of USA, National Academy of Science, Washington, D.C., US, v. 82, No. 10, p. 3400-3404, tables 1, Peptide 21, XP000113798, ISSN: 0027-8424, May 1, 1985.

Weber, E. et al., "Fine Mapping of a Peptide Sequence Containing an Antigenic Site Conserved Among Arenaviruses," Virology, vol. 164, p. 30-38 (1988).

Yasuko, A-O, et al., "Intranasal administration of adjuvant-combined recombinant influenza virus HA vaccine protects mice from the lethal H5N1 virus infection." Microbes and Infection, vol. 8, Issues 12-13, pp. 2706-2714, Oct. 2006.

Zhao, Neutralizing monoclonal antibody against Anthrax lethal factor inhibits intoxication in a mouse model, Human Antibodies, vol. 12, pp. 129-135 (2003).

* cited by examiner

Shrimp vaccinated with T1 and challenged with TSV

Shrimp challenged with TSV (no vaccination)

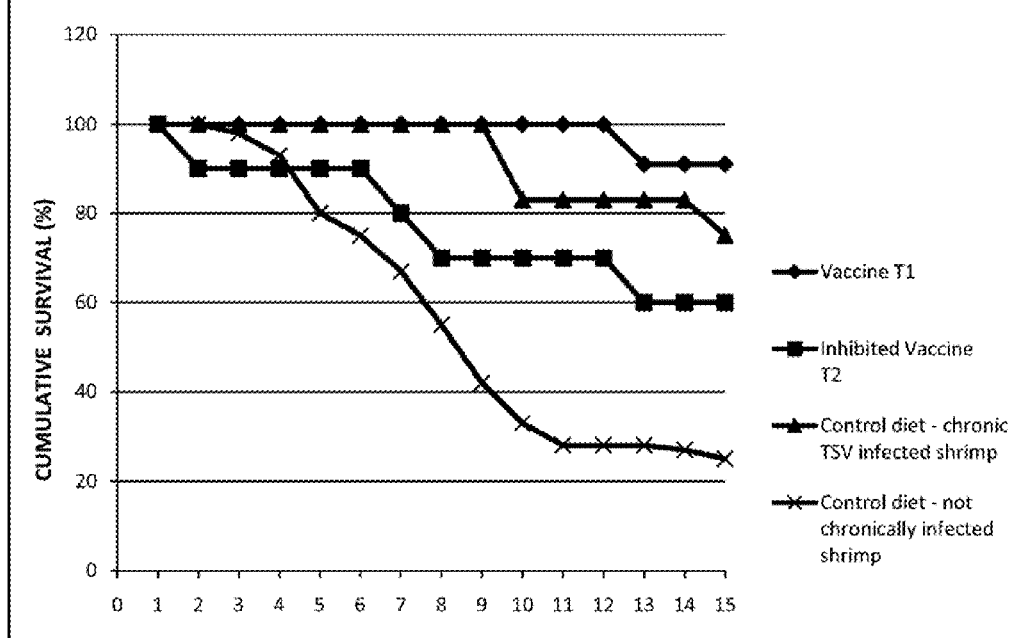

FIGURE 3

Replikin Concentration vs Day of 50% Mortality of Shrimp Challenged with Taura Syndrome Virus

- Belize isolate
- Thailand isolate
- Hawaii isolate
- Venezuela isolate

Replikin Concentration

Day of 50% mortality

Cumulative survival of *Litopenaeus vannamei per os* challenged with TSV isolates; A: Belize; B: Thailand; C: H

Year   2003      2004      2005      2006      2007 1st Qtr
HUMAN H5N1
Light Gray = Whole virus Replikin Concentration (Number of Replikins per 100 amino acids)
Dark Gray = Replikin Peak Gene Replikin Concentration
Uncolored Bar = Standard Deviation
Black = % Human Mortality Rate (x 10)

FIG. 11

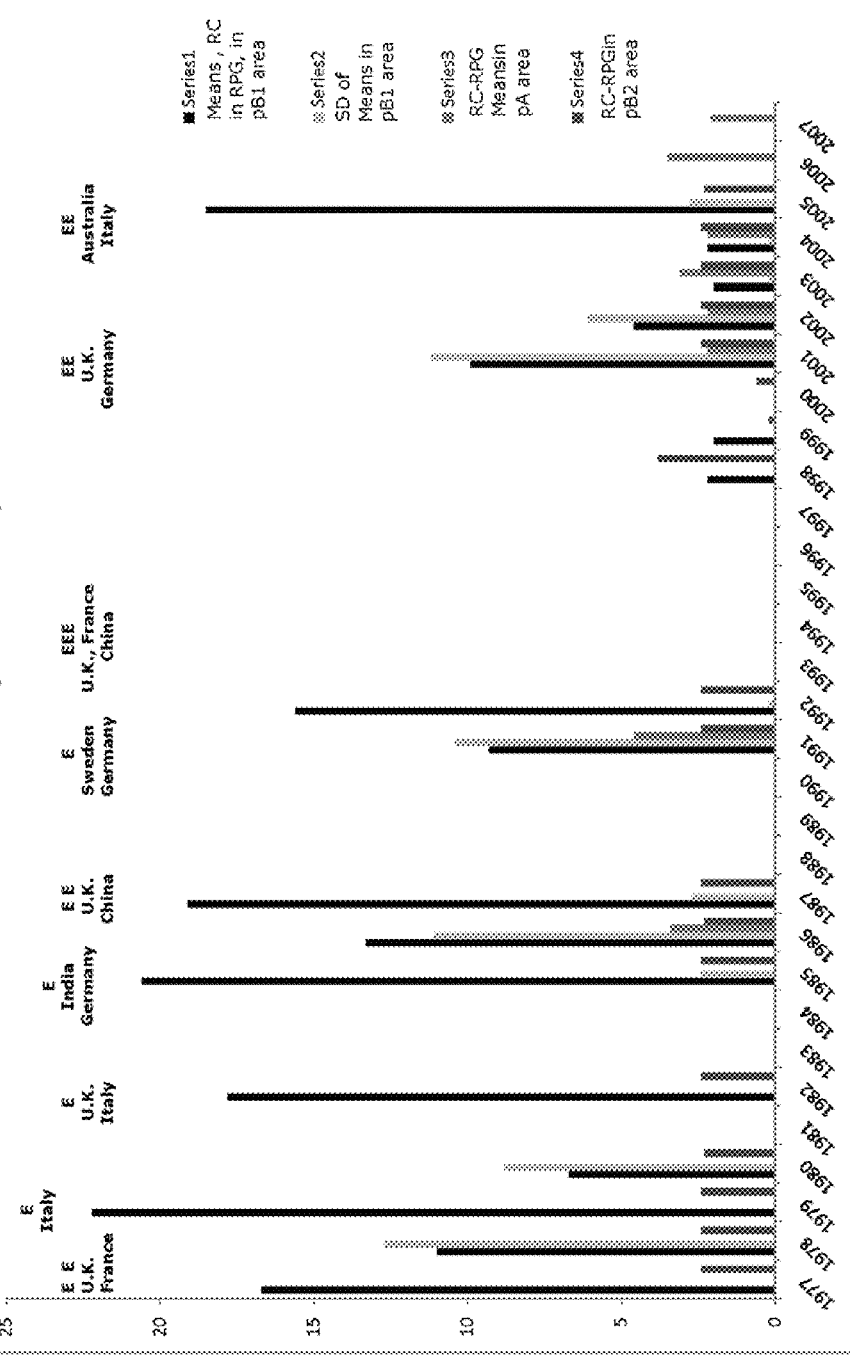

SYNTHETIC REPLIKIN PEPTIDES AGAINST PATHOGENIC INFECTION OF INVERTEBRATES IN AQUACULTURE

This application claims priority to U.S. application Ser. No. 12/010,027, filed Jan. 18, 2008, U.S. Provisional Appln. Ser. No. 60/991,676, filed Nov. 30, 2007, U.S. application Ser. No. 11/923,559, filed Oct. 24, 2007, U.S. Provisional Appln. Ser. No. 60/982,336, filed Oct. 24, 2007, U.S. Provisional Appln. Ser. No. 60/982,333, filed Oct. 24, 2007, U.S. Provisional Appln. Ser. No. 60/982,338, filed Oct. 24, 2007, U.S. Provisional Appln. Ser. No. 60/935,816, filed Aug. 31, 2007, U.S. Provisional Appln. Ser. No. 60/935,499 filed Aug. 16, 2007, U.S. Provisional Appln. Ser. No. 60/954,743, filed Aug. 8, 2007, and U.S. application Ser. No. 11/755,597, filed May 30, 2007, each of which is incorporated herein by reference in its entirety. This application additionally incorporates herein by reference: U.S. Provisional Appln. Ser. No. 60/898,097, filed Jan. 30, 2007, U.S. Provisional Appln. Ser. No. 60/880,966, filed Jan. 18, 2007, U.S. Provisional Appln. Ser. No. 60/853,744, filed Oct. 24, 2006, U.S. application Ser. No. 11/355,120, filed Feb. 16, 2006, U.S. application Ser. No. 11/116,203, filed Apr. 28, 2005, U.S. application Ser. No. 10/860,050, filed Jun. 4, 2004, U.S. application Ser. No. 10/189,437, filed Jul. 8, 2002, U.S. application Ser. No. 10/105,232, filed Mar. 26, 2002, now U.S. Pat. No. 7,189,800, U.S. application Ser. No. 09/984,057, filed Oct. 26, 2001, and U.S. application Ser. No. 09/984,056, filed Oct. 26, 2001, now U.S. Pat. No. 7,176,275, each in its entirety.

Aquaculture refers generally to the breeding and raising of aquatic animals for food. Aquaculture is a rapidly expanding global industry in the $21^{st}$ century. The most significant cause of economic loss in the industry is disease. Meyer, F. P., *J Anim Sci* 1991. 69:4201-4208. Aquaculture, and in particular invertebrate aquaculture, frequently involves short-term holding of dense numbers of animals in pens or tanks before marketing or to induce molting. Id. These concentrations are stressful for the invertebrates such as shrimp, clams, oysters, lobster, scallops, abalone, etc. The stressful conditions are ideal for transmission of pathogens including bacteria, such as *Vibrio, Chlamydia*-like, and *Rickettsia*-like species, viruses, such as taura syndrome virus and white spot syndrome virus, and other microbial pathogens.

One particularly severe viral disease in aquaculture is taura syndrome, which significantly impacts the shrimp farming industry worldwide. Taura syndrome is caused by the taura syndrome virus (TSV), which is a member of the Discistroviridae family in the genus *Cripavirus* and has a single positive stranded genome of about 10,000 nucleotides. The genome contains two open reading frames (ORF). ORF1 reportedly contains coding for a helicase, a protease and an RNA-dependent RNA polymerase. ORF2 reportedly contains coding for three capsid proteins.

Taura Syndrome is now considered endemic in the Americas and outbreaks have been observed in Asia. Infected shrimp generally have a red tail, are anorexic and erratic in their behavior, tail muscles may become opaque, and the cutical may become soft. Mortality rates between 5% and 95% have been observed during the acute phase of the disease. Shrimp that survive outbreaks of TSV seem to be refractory to reinfection while remaining infectious.

Rapid replication is characteristic of virulence in certain bacteria, viruses and malignancies including TSV and other viral and bacterial diseases in aquaculture such as *Chlamydia*-like diseases and white spot syndrome, a viral disease. The inventors have found a family of conserved peptide sequences related to rapid replication, designated Replikins. The inventors have correlated an increase in the concentration of Replikin peptides in strains of influenza and other viruses with increased viral virulence. There is a need in the art for methods of preventing and treating pathogenic infections by manipulating the replicating function of Replikin sequences and for identifying molecular targets related to the replicating function of Replikin sequences for treatment of virulent infections, including vaccines and other therapies. Additionally, there is need in the art for reducing the time required for development of vaccines and other therapies to emerging pathogens that rapidly expand through a population or are highly mutable or both. The present time frame of three to twelve months for development of a vaccine often delivers vaccines after an epidemic has long since ended or, if still active, after mutations in the pathogen have rendered a vaccine less effective or useless. These problems in the art are a significant worry to human and animal health professionals and governments.

SUMMARY OF THE INVENTION

The present invention provides synthetic peptide sequences and isolated, synthetic or synthesized Replikin peptide sequences for prevention and treatment of outbreaks of pathogens in invertebrates in aquaculture, and methods of administering to the invertebrates in aquaculture one or more substances comprising or consisting of one or more of the isolated, synthetic or synthesized Replikin peptide sequences to prevent and/or treat outbreaks of pathogens in the invertebrates.

A first non-limiting aspect of the present invention provides a substance for use in aquaculture comprising at least one synthetic peptide of about seven to about fifty amino acids wherein the at least one synthetic peptide, when administered to at least one invertebrate that is capable of culture in water, increases the resistance of that invertebrate to at least one pathogen. In a non-limiting embodiment, the at least one invertebrate is a crustacean. In a further non-limiting embodiment, the at least one crustacean is a shrimp.

A further non-limiting embodiment of the first aspect of the invention provides a substance for increasing the resistance of an invertebrate in aquaculture comprising at least one isolated or synthetic peptide, which is at least one isolated or synthetic form of at least one peptide from a pathogen to said invertebrate, wherein said at least one isolated or synthetic peptide is at least one isolated or synthetic Replikin peptide consisting of 7 to about 50 amino acids comprising a Replikin motif wherein said Replikin motif comprises:
  (1) at least one lysine residue located at a first terminus of said motif and a least one lysine residue or at least one histidine residue located at a second terminus of said motif;
  (2) at least one lysine residue located six to ten residues from a second lysine residue;
  (3) at least one histidine residue; and
  (4) at least six percent lysine residues.

In a further non-limiting embodiment, the at least one isolated or synthetic Replikin peptide consists of the Replikin motif. In a further non-limiting embodiment, the Replikin motif consists of about 7 to about 10, about 10 to about 15 amino acids, about 15 to about 20 amino acids, about 20 to about 25 amino acids, about 25 to about 30 amino acids, about 30 to about 35 amino acids, about 35 to about 40 amino acids, about 40 to about 45 amino acids, or about 45 to about 50 amino acids.

In a further non-limiting embodiment of the invention, the at least one isolated or synthetic Replikin peptide comprises any one of SEQ ID NOS: 1-11, 86, 87, 103-112, and 114-198. In a further non-limiting embodiment, the substance comprises a mixture of one or more of the isolated or synthetic Replikin peptides of SEQ ID NOS: 1-11, 86, 87, 103-112, and 114-198. In a further non-limiting embodiment, the at least one isolated or synthetic Replikin peptide comprises KVGSRRYKSH (SEQ ID NO: 1), HFATKCFGEVPKK (SEQ ID NO: 2), KAENEFWDGVKQSH (SEQ ID NO: 3), KGHRKVPCEQK (SEQ ID NO: 4), HRKVPCEQK (SEQ ID NO: 5), KVPCEQKIWLH (SEQ ID NO: 6), KIWLHQNPGK (SEQ ID NO: 7), HQNPGKTQQDMK (SEQ ID NO: 8), KGNTRVHVK (SEQ ID NO: 9), KEHVEKIVDK (SEQ ID NO: 10), or HVEKIVDKAK (SEQ ID NO: 11). In a further non-limiting embodiment, the substance of the first aspect of the invention comprises a mixture of any two or more of the synthetic Replikin peptides. In a further non-limiting embodiment, the substance comprises an equal mixture by weight of the synthetic Replikin peptides.

A second non-limiting aspect of the invention provides a vaccine comprising a substance for use in aquaculture, comprising at least one isolated or synthetic peptide of about 7 to about 50 amino acids, wherein the at least one isolated or synthetic peptide, when administered to at least one invertebrate capable of culture in water, increases the resistance of the invertebrate to at least one pathogen.

In a non-limiting embodiment of the second aspect of the invention, the at least one isolated or synthetic peptide of the substance of the vaccine is at least one Replikin peptide wherein the Replikin peptide consists of 7 to about 50 amino acids and comprises a Replikin motif comprising:
(1) at least one lysine residue located at a first terminus of said motif and a least one lysine residue or at least one histidine residue located at a second terminus of said motif;
(2) at least one lysine residue located six to ten residues from a second lysine residue;
(3) at least one histidine residue; and
(4) at least six percent lysine residues.

In a further embodiment, the vaccine further comprises a pharmaceutically acceptable carrier.

In a further non-limiting embodiment of the second aspect of the invention, the vaccine provides protection against at least one pathogen in an invertebrate, such as a crustacean or mollusk. In a further non-limiting embodiment, the vaccine provides protection against at least one pathogen in a shrimp. In a further non-limiting embodiment, the vaccine is mixed with feed for shrimp for administration to shrimp. In a further non-limiting embodiment, the vaccine is mixed with the daily ration of feed for shrimp. In a further non-limiting embodiment, the pathogen is a virus. In a further non-limiting embodiment, the pathogen is a taura syndrome virus.

In a further non-limiting embodiment of the second aspect of the invention, at least one isolated or synthetic peptide of the vaccines is any one of SEQ ID NOS: 1-11, 86, 87, 103-112, and 114-198. In a further non-limiting embodiment, the vaccine comprises a mixture of one or more of the isolated or synthetic Replikin peptides of SEQ ID NOS: 1-11, 86, 87, 103-112, and 114-198.

In a further non-limiting embodiment of a second aspect of the invention, at least one synthetic peptide of the vaccine is KVGSRRYKSH (SEQ ID NO: 1), HFATKCFGEVPKK (SEQ ID NO: 2), KAENEFWDGVKQSH (SEQ ID NO: 3), KGHRKVPCEQK (SEQ ID NO: 4), HRKVPCEQK (SEQ ID NO: 5), KVPCEQKIWLH (SEQ ID NO: 6), KIWLHQNPGK (SEQ ID NO: 7), HQNPGKTQQDMK (SEQ ID NO: 8), KGNTRVHVK (SEQ ID NO: 9), KEHVEKIVDK (SEQ ID NO: 10), or HVEKIVDKAK (SEQ ID NO: 11). In a further non-limiting embodiment, the vaccine comprises a mixture of any two or more of the synthetic peptides. In a further non-limiting embodiment, the vaccine comprises a mixture of each of the synthetic peptides. In a further non-limiting embodiment, the vaccine comprises an equal mixture by weight of each of the synthetic peptides.

In a further non-limiting embodiment of the second aspect of the invention, the vaccine is administered to at least one shrimp at about 0.001 mg to about 10 mg of vaccine per gram of body weight of each treated shrimp per day. In a further non-limiting embodiment, the vaccine is administered to at least one shrimp at about 0.005 mg to about 5 mg of vaccine per gram of body weight of each treated shrimp per day. In a further non-limiting embodiment, the vaccine is administered to at least one shrimp at about 0.01 mg to about 2 mg of vaccine per gram of body weight of each treated shrimp per day. In a further non-limiting embodiment, the vaccine is administered to at least one shrimp at about 0.02 mg to about 1.5 mg of vaccine per gram of body weight of each treated shrimp per day. In a further non-limiting embodiment, the vaccine is administered to at least one shrimp at about 0.08 mg to about 1.0 mg of vaccine per gram of body weight of each treated shrimp per day. In a further non-limiting embodiment, the vaccine is administered to at least one shrimp at about 0.1 mg to about 0.9 mg of vaccine per gram of body weight of each treated shrimp per day. In a further non-limiting embodiment, the vaccine is administered to at least one shrimp at about 0.2 mg to about 0.8 mg of vaccine per gram of body weight of each treated shrimp per day. In a further non-limiting embodiment, the vaccine is administered to at least one shrimp at about 0.5 mg of vaccine per gram of body weight of each treated shrimp per day.

In a further non-limiting embodiment of the second aspect of the invention, the at least one isolated, synthesized or synthetic Replikin peptide of a vaccine of the invention is at least one isolated, synthesized or synthetic form of at least one Replikin peptide present in an emerging strain of taura syndrome virus.

In a further non-limiting embodiment of the second aspect of the invention, a vaccine of the invention is administered to shrimp as a prophylactic therapy prior to the onset of symptoms of taura syndrome virus. In a further non-limiting embodiment, the vaccine of the invention is administered to shrimp as a prophylactic therapy after the onset of symptoms of taura syndrome virus. In a further non-limiting embodiment, the vaccine is administered at sub-therapeutic concentrations. In a further non-limiting embodiment, the vaccine is administered over substantially all of the life cycle of at least one shrimp.

A third non-limiting aspect of the present invention provides a method of providing resistance in an invertebrate in aquaculture, comprising administering a substance comprising at least one synthetic peptide, wherein the at least one synthetic peptide, when administered to at least one invertebrate that is capable of culture in water, is capable of increasing resistance to at least one pathogen. In a non-limiting embodiment, the substance is administered orally, via submersion of the invertebrate in an aqueous medium containing the substance, or via injection. In a further non-limiting embodiment, the substance is administered orally. In a non-limiting embodiment, the invertebrate is a crustacean. In a further non-limiting embodiment, the crustacean is a shrimp.

A fourth non-limiting aspect of the present invention provides an isolated, synthetic or synthesized taura syndrome virus Replikin peptide consisting of 7 to about 50 amino acids wherein the Replikin peptide comprises a Replikin motif comprising:

(1) at least one lysine residue located at a first terminus of said motif and a least one lysine residue or at least one histidine residue located at a second terminus of said motif;
(2) at least one lysine residue located six to ten residues from a second lysine residue;
(3) at least one histidine residue; and
(4) at least six percent lysine residues.

In a further non-limiting embodiment of the invention the isolated, synthetic or synthesized taura syndrome virus Replikin peptide consists of the Replikin motif. A further non-limiting embodiment provides a nucleotide sequence encoding the taura syndrome virus Replikin peptide.

A fifth non-limiting aspect of the present invention provides an isolated, synthetic or synthesized taura syndrome virus Replikin Scaffold peptide consisting of about 16 to about 34 amino acids comprising:
(1) a terminal lysine and optionally a lysine immediately adjacent to the terminal lysine;
(2) a terminal histidine and optionally a histidine immediately adjacent to the terminal histidine;
(3) a lysine within about 6 to about 10 amino acids from another lysine; and
(4) at least 6% lysines.

In a further non-limiting embodiment, the isolated, synthetic or synthesized taura syndrome virus Replikin Scaffold peptide consists of about 28 to about 33 amino acids. In a further non-limiting embodiment, the peptide comprises

KKVQANKTRVFAASNQGLALALRRYYLSFLDH (SEQ ID NO: 197)

or

KKACRNAGYKEACLHELDCKSFLLAQQGRAGAH. (SEQ ID NO: 198)

A sixth non-limiting aspect of the present invention provides a method of increasing resistance of an invertebrate to a pathogen comprising:
(1) challenging a plurality of invertebrates being of the same species as said invertebrate with said pathogen at sufficient levels to cause disease in at least one individual of the plurality of said invertebrates;
(2) discarding at least one individual of the plurality said invertebrates that is diseased or dead;
(3) repeating steps 1 and 2 at least once; and
(4) at least once administering to the plurality of said invertebrates the substance of claim 1 in steps (1), (2) and/or (3) which increases the resistance of said invertebrate to the pathogen.

In a non-limiting embodiment of the sixth aspect of the present invention, the at least one isolated or synthetic peptide is at least one Replikin peptide consisting of 7 to about 50 amino acids and comprising a Replikin motif comprising:
(1) at least one lysine residue located at a first terminus of said motif and a least one lysine residue or at least one histidine residue located at a second terminus of said motif;
(2) at least one lysine residue located six to ten residues from a second lysine residue;
(3) at least one histidine residue; and
(4) at least six percent lysine residues.

In a further non-limiting embodiment, the invertebrate is a shrimp. In a further non-limiting embodiment, the pathogen is taura syndrome virus.

A seventh non-limiting aspect of the present invention provides a method of producing a vaccine comprising: (1) identifying at least one Replikin sequence in a pathogen of an invertebrate capable of culture in an aqueous medium, and (2) chemically synthesizing the at least one identified Replikin sequence as an active agent of the vaccine. In a non-limiting embodiment, the vaccine is produced in seven days or fewer from the time the at least one Replikin sequence in the pathogen is identified.

An eighth non-limiting aspect of the present invention provides animal feed comprising a substance for use in aquaculture, comprising at least one synthetic peptide of about seven to about fifty amino acids, wherein the at least one synthetic peptide, when administered to at least one invertebrate that is capable of culture in an aqueous medium, increases the resistance of that invertebrate to at least one pathogen. In a non-limiting embodiment, the animal feed is feed for a crustacean. In a further non-limiting embodiment, the animal feed is feed for a shrimp. In a further embodiment the synthetic peptide of the substance of the animal feed is a synthetic Replikin peptide. In a further embodiment, the animal feed comprises shrimp production Rangen 35 mash, 1% sodium alginate, 1% sodium hexametaphosphate, and at least one synthetic Replikin peptide that is KVGSRRYKSH (SEQ ID NO: 1), HFATKCFGEVPKK (SEQ ID NO: 2), KAENEFWDGVKQSH (SEQ ID NO: 3), KGHRKVPCEQK (SEQ ID NO: 4), HRKVPCEQK (SEQ ID NO: 5), KVPCEQKIWLH (SEQ ID NO: 6), KIWLHQNPGK (SEQ ID NO: 7), HQNPGKTQQDMK (SEQ ID NO: 8), KGNTRVHVK (SEQ ID NO: 9), KEHVEKIVDK (SEQ ID NO: 10), or HVEKIVDKAK (SEQ ID NO: 11).

A ninth non-limiting aspect of the present invention provides a shrimp treated with a vaccine comprising at least one Replikin peptide wherein the at least one Replikin peptide consists of 7 to about 50 amino acids and comprises a Replikin motif comprising:
(1) at least one lysine residue located at a first terminus of said motif and a least one lysine residue or at least one histidine residue located at a second terminus of said motif;
(2) at least one lysine residue located six to ten residues from a second lysine residue;
(3) at least one histidine residue; and
(4) at least six percent lysine residues.

In a further embodiment, the Replikin peptide is a taura syndrome virus Replikin peptide. In a further embodiment of the ninth aspect of the present invention, the shrimp is (1) challenged with taura syndrome virus along with a plurality of other shrimp at sufficient levels to cause disease in at least one of the plurality of shrimp; (2) the shrimp of the plurality of shrimp that are diseased or dead or both are discarded; (3) steps 1 and 2 are repeated at least once; and (4) said plurality of shrimp are administered a vaccine at least once in steps (1), (2) and/or (3), wherein the vaccine comprises at least one isolated or synthetic taura syndrome virus Replikin peptide.

BRIEF DESCRIPTION OF THE DRAWINGS

FIG. 1 illustrates percent survival of shrimp (*Penaeus vannamei*) challenged with taura syndrome virus over 15 day trials. FIG. 1A illustrates 5 trials each conducted over the same 15 day period along with controls. FIG. 1B illustrates the three control trials over the same 15 day period. After removal of one outlier from a total of six trials (as explained in Example 2 below), the vaccinated shrimp had a cumulative survival of 59% (FIG. 1A). The non-vaccinated shrimp has a cumulative survival of 25% (FIG. 1B). Cumulative survival of vaccinated shrimp was greater than cumulative survival of non-vaccinated shrimp. These data indicate that vaccination with Replikin sequences provided protection from TSV infection. The relative percent survival against TSV after vaccination was 45%.

FIG. 2 illustrates 15 day cumulative survival of shrimp (Penaeus vannamei) previously challenged (chronically infected) with taura syndrome virus (TSV) and subsequently challenged a second time with TSV after treatment with T1 vaccine, T2 inhibited or "blocked" vaccine, or no vaccine (control). An additional control study is illustrated with shrimp that had not been previously challenged with TSV (not chronically infected). This additional control was not treated with vaccine. For T1-vaccinated shrimp, there were no mortalities until day 13. This group had a 91% survival at day 15 after exposure to TSV. For shrimp fed inhibited-vaccine T2, the first mortality was observed at day 2. The group had a survival of 60%. For the non-vaccinated control group that had been subject to previous TSV challenge, the first mortality occurred on day 10, and the group had a survival of 75%. For the additional control group that had not previously been challenged with taura syndrome virus (SPF shrimp), cumulative survival was 25%. These results show that TSV-chronically-infected shrimp had higher percent survivals (60-91%) when re-challenged with TSV. In particular, T1-vaccinated *P. vannamei* had a highest survival and lowest viral load. The percent survival for SPF *P. vannamei* challenged with TSV was 25%. The trial illustrated in FIG. 2 is described in Example 3 below.

FIG. 3 illustrates a direct sequential correlation between Replikin concentration of isolates of taura syndrome virus (TSV) collected from Belize, Thailand, Hawaii and Venezuela, respectively, and mean number of days to 50% mortality in *Litopenaeus vannamei* shrimp challenged with the respective TSV isolates on days 1, 2, and 3. Statistical differences between the Replikin concentration for each isolate are significant at a level of $p<0.001$. The data illustrated in FIG. 3 are described in Example 1 below.

Figure 6:
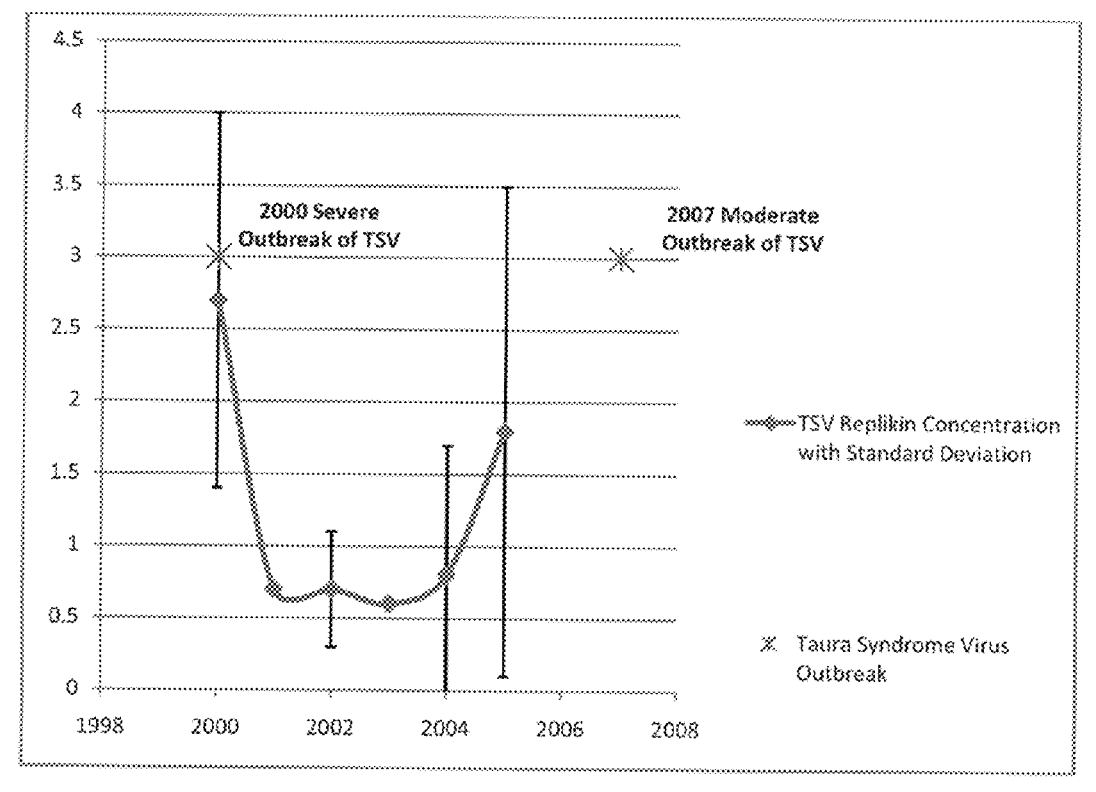

FIG. 6 illustrates a correlation between increased Replikin concentration in the genome of taura syndrome virus and outbreaks of the virus in 2000 and 2007 in shrimp. Taura syndrome virus peptide sequences available at www.pubmed.com were analyzed by the inventors for mean Replikin concentration in the publicly available sequences. FIG. 6 is a graph comparing mean Replikin concentration for each year in which peptide sequences were publicly available between 2000 and 2005 (with standard deviation) and dates of significant outbreaks of taura syndrome virus. The Replikin concentration data reflected in the graph is found in Table 13 below. Significant outbreaks of the disease are noted at years 2000 and 2007. It may be observed from the graph that outbreaks of the virus occur following an increase in Replikin concentration. In year 2000, TSV had a Replikin concentration of 2.7. Between 2001 and 2004, TSV had a lower mean Replikin concentration, as low as 0.6, and an identified Replikin Scaffold disappeared. In 2005 the Replikin Scaffold reappeared, with an increase in lysines and histidines, and a commensurate increase in Replikin concentration to 1.8, followed by an increase in TSV outbreaks in 2006-2007. See Replikin Scaffolds in Example 5 for TSV in 2000 and 2005.

Figure 4:
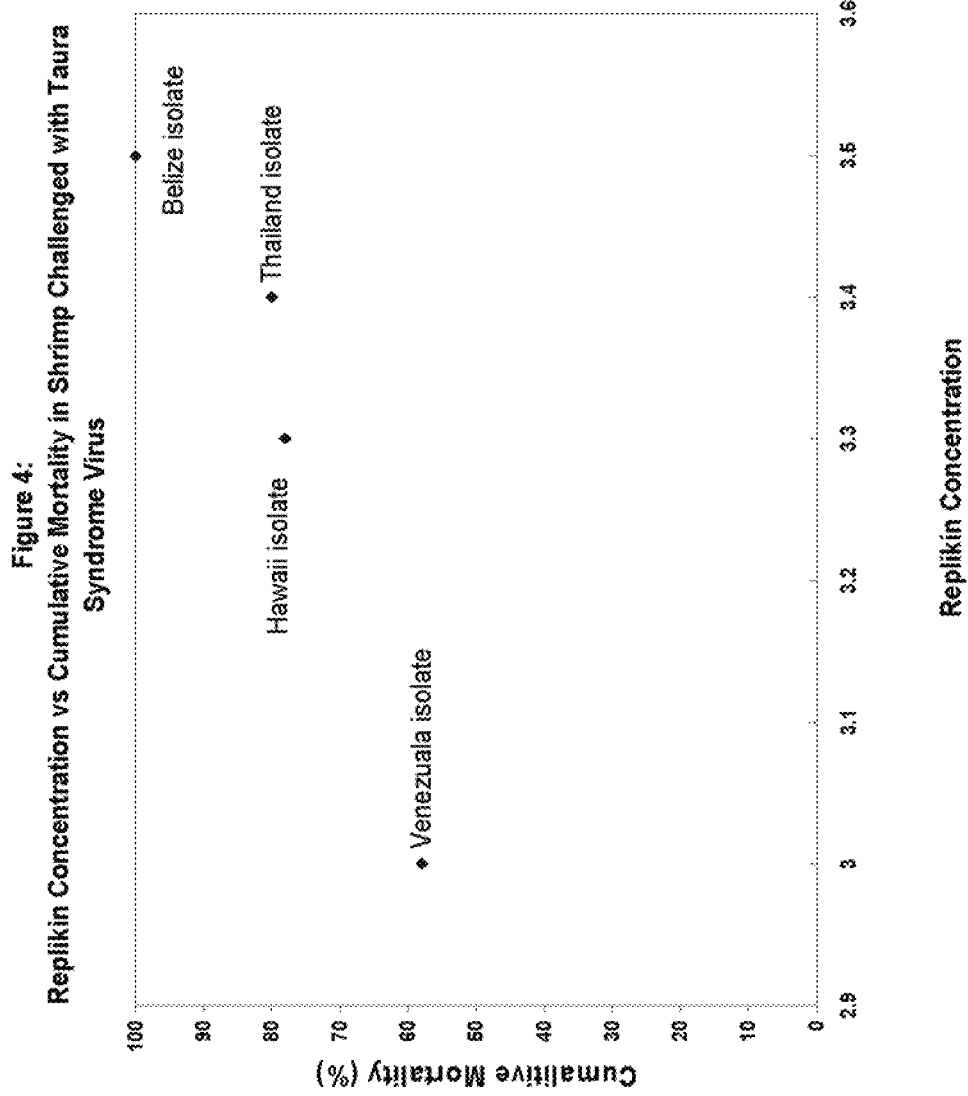
FIG. 4 illustrates a direct correlation between Replikin concentration in isolates of taura syndrome virus (TSV) collected from Belize, Thailand, Hawaii and Venezuela, respectively, and mean cumulative survival of *Litopenaeus vannamei* shrimp at 15 days after challenge with respective TSV isolates. Statistical differences between the Replikin concentrations for each isolate are significant at a level of $p<0.001$. The data illustrated in FIG. 4 are described in Example 1 below.
Figure 5:
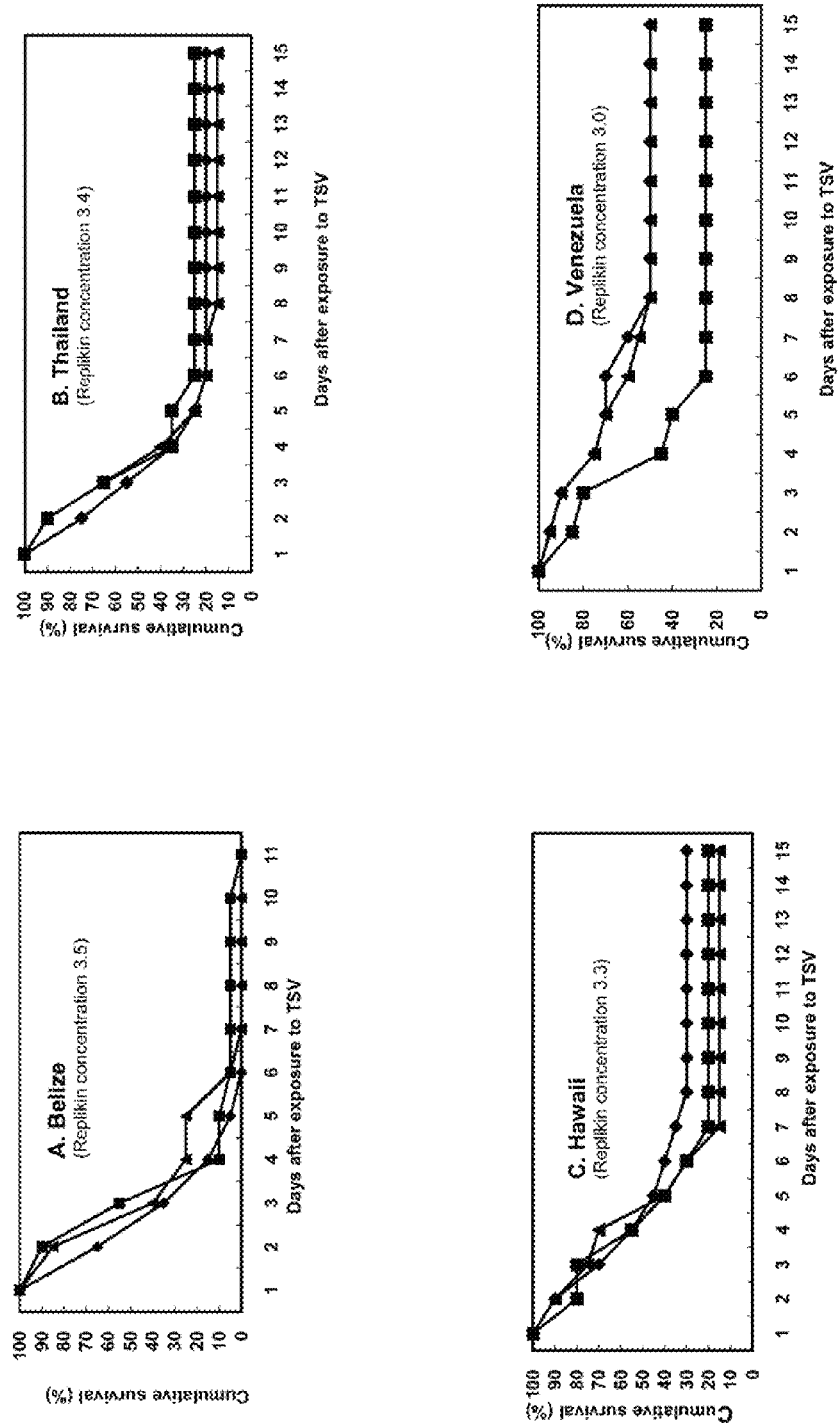
FIG. 5 illustrates a correlation between cumulative survival of *Litopenaeus vannamei* shrimp challenged with four different taura syndrome virus isolates over 15 days (unless 100% mortality occurred prior to 15 days) and the Replikin concentration of Open Reading Frame 1 (ORF1) of each isolate. Translated amino acid sequences of ORF1 of the genome of individual isolates of TSV from Belize, Thailand, Hawaii and Venezuela were analyzed for Replikin concentration. Replikin concentration was determined to be 3.5 for the Belize isolate, 3.4 for the Thailand isolate, 3.3 for the Hawaii isolate and 3.0 for the Venezuela isolate. Graph A illustrates observed percent survival in three trials of shrimp challenged with the Belize isolate of TSV. In one trial, total mortality was observed on day 6. In the other trials, total mortality was observed on day 11. Graphs B, C and D illustrate observed percent survival of shrimp challenged with the Thailand isolate, the Hawaii isolate and the Venezuela isolate, respectively, each in three trials over 15 days. In the Thailand isolate, a mean of 80% percent mortality was observed on day 15. In the Hawaii isolate, a mean of 78.3% mortality was observed on day 15. In the Venezuela isolate, a mean of 58.3% mortality was observed on day 15. The data illustrated in FIG. 5 are described in Example 1 below.

The observed increase in mean Replikin Count from 2000 to 2003 in West Nile virus precedes an increase in the number of human West Nile virus (WNV) cases recorded independently and published by CDC. The same detailed relationship of Replikin Count to morbidity has been shown in influenza strains, for example H5N1 to human mortality (see FIG. 8), and in H3N8 equine encephalitis to horse morbidity (see FIG. 12), and in the trypanosome *Plasmodium falciparum* (malaria) to human mortality (see FIG. 9), and to mortality rate in shrimp with taura syndrome virus (see FIGS. 3-5). Since the relationship has already been demonstrated in several species, namely crustacea, horses, and humans, and since Replikin sequences have been associated with rapid replication in plants, invertebrate animals, vertebrate animals, protozoa (such as trypanosomes), bacteria (such as anthrax) and viruses (see, e.g., U.S. Pat. Nos. 7,176,275 and 7,189,800), relating Replikin Count to morbidity appears to be a broadly distributed general principle.

Figure 7:
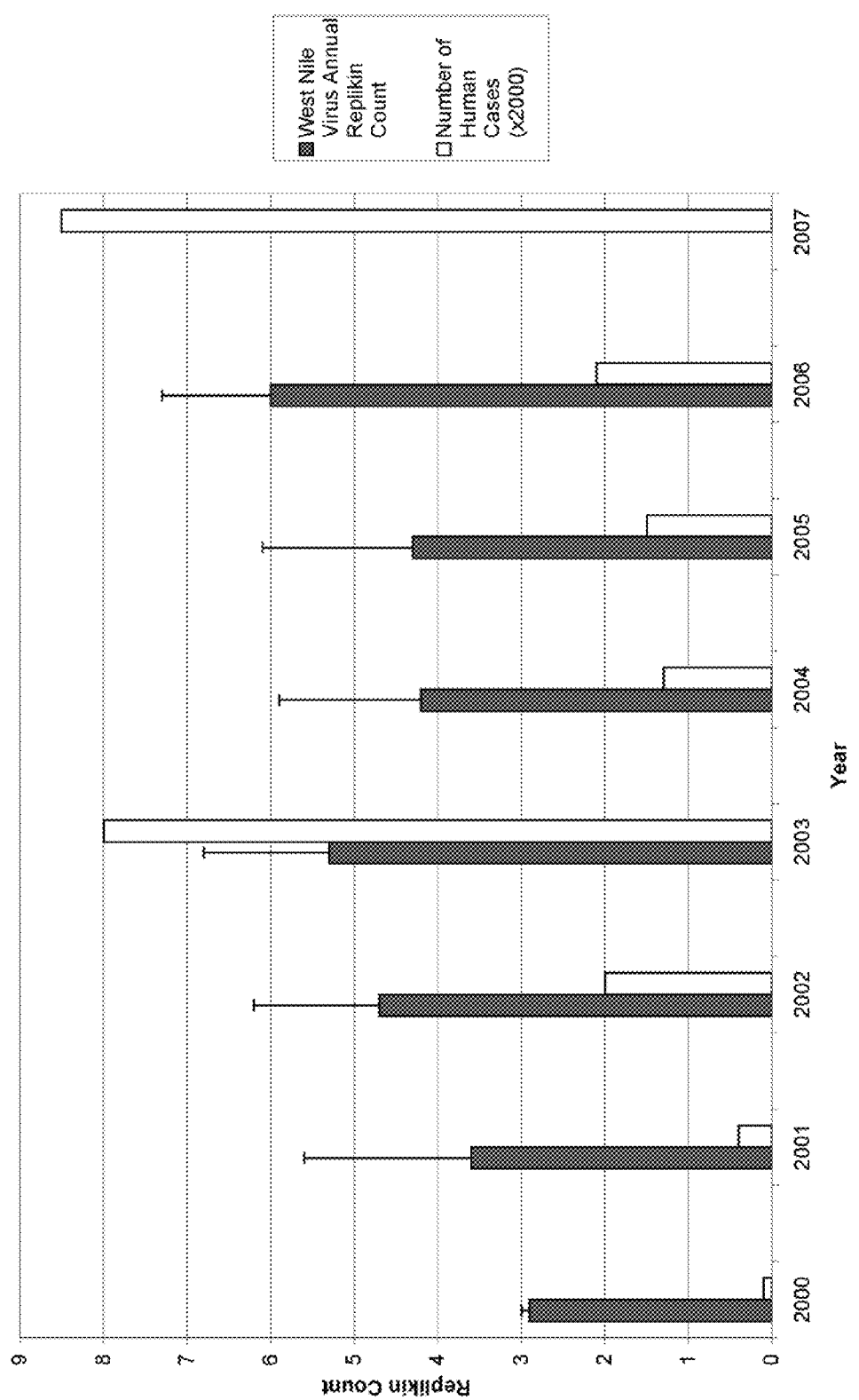
FIG. 7 illustrates cyclic production of West Nile virus Replikins and annual human morbidity by demonstrating a correlation between annual Replikin concentration per 100 amino acids (Replikin Count) of the envelope protein of West Nile virus (Replikin Count mean is illustrated with black bars with standard deviation depicted) and the annual number of human cases in the United States as reported by the Centers for Disease Control (CDC) on a statewide basis. A review of the data reveals that the standard deviation of the mean of the Replikin Count of the envelope protein increases markedly between 2000 and 2001 (statistical significance with a $p<0.001$). This kind of change in standard deviation from the mean of the Replikin Count of a virus population has been observed to signal rapid replication and expansion of the range of the Replikin Count in all common strains of influenza virus (influenza virus is classified in a significantly different family of viruses than is West Nile virus). In influenza, a marked statistical change in the Replikin Count has been observed to precede viral outbreaks.

The data in FIG. 7 additionally illustrate in 2004, and again in 2005, that there was a decrease in both the Replikin Count and the number of human cases of WNV. In 2006, an increase in Replikin Count was followed by an increase in the number of human cases (morbidity) in 2007. FIG. 7, therefore, illustrates two cycles of Replikin concentration (Replikin Count) and two cycles of changing WNV human morbidity. The two cycles (Virus Replikin Cycles) between 2000-2003 and 2004-2008 are observed to correlate in FIG. 7. Cycles in Replikin Count have been observed in previous influenza virus data with H1N1 and H3N2 (see, e.g., FIG. 11). The relationship is even more clearly demonstrated in the WNV data than it is influenza because the actual number of cases resulting from the H1N1 or H3N2 influenza viruses was not historically recorded for the particular strain as accurately as they are now recorded for West Nile Virus. Instead, H1N1 and H3N2 were recorded as outbreaks, epidemics, or pandemics. The stepwise increase in Replikin concentration (Replikin Count) in repeated cycles can serve as a method for predicting viral expansion. Monitoring of stepwise increases in Replikin Count provides the skilled artisan with data predicting expansion in viral population and resultant morbidity including, outbreaks, epidemics, and pandemics of viral diseases. Actual morbidity in these events was not recorded. It should be noted that data for Replikin Count in 2007 and 2008 are excluded from FIG. 7 because CDC reporting of WNV sequences was delayed as of the drafting of this application.

The data in FIG. 7 is also important because, rather than the virus revisiting a country after many previous epidemics, as for example in the case of H1N1 or H3N2, FIG. 7 describes the progress of a virus that arrived for the first time in New York City in 1999 and spread over the entire United States thereafter. The opportunity is present to examine the steps in this spread in terms of the newly recognized Replikin structure of the virus and the excellent epidemiological data provided by CDC.

FIG. 8 illustrates the relationship of Replikin Count of the Replikin Peak Gene pB1 gene area in human H5N1 to percent human mortality between 2003 and 2007 in human cases of H5N1 infection. An increase in Replikin Count in the pB1 gene area of H5N1 is observed to be quantitatively related to higher mortality in the host. In the graph, (1) light gray represents the mean Replikin Count of whole virus isolates at a given year, (2) dark gray represents the mean Replikin Count in the pB1 area of publicly available sequences of isolates of human H5N1 at a given year, (3) the white bars represent the standard deviation from the mean of Replikin Count in a given year, and (4) the black bars represent 10% of the percent mortality of identified human cases of H5N1 infection in the given year, finally reaching 86% mortality (shown in FIG. 8 as 8.6).

Figure 9:
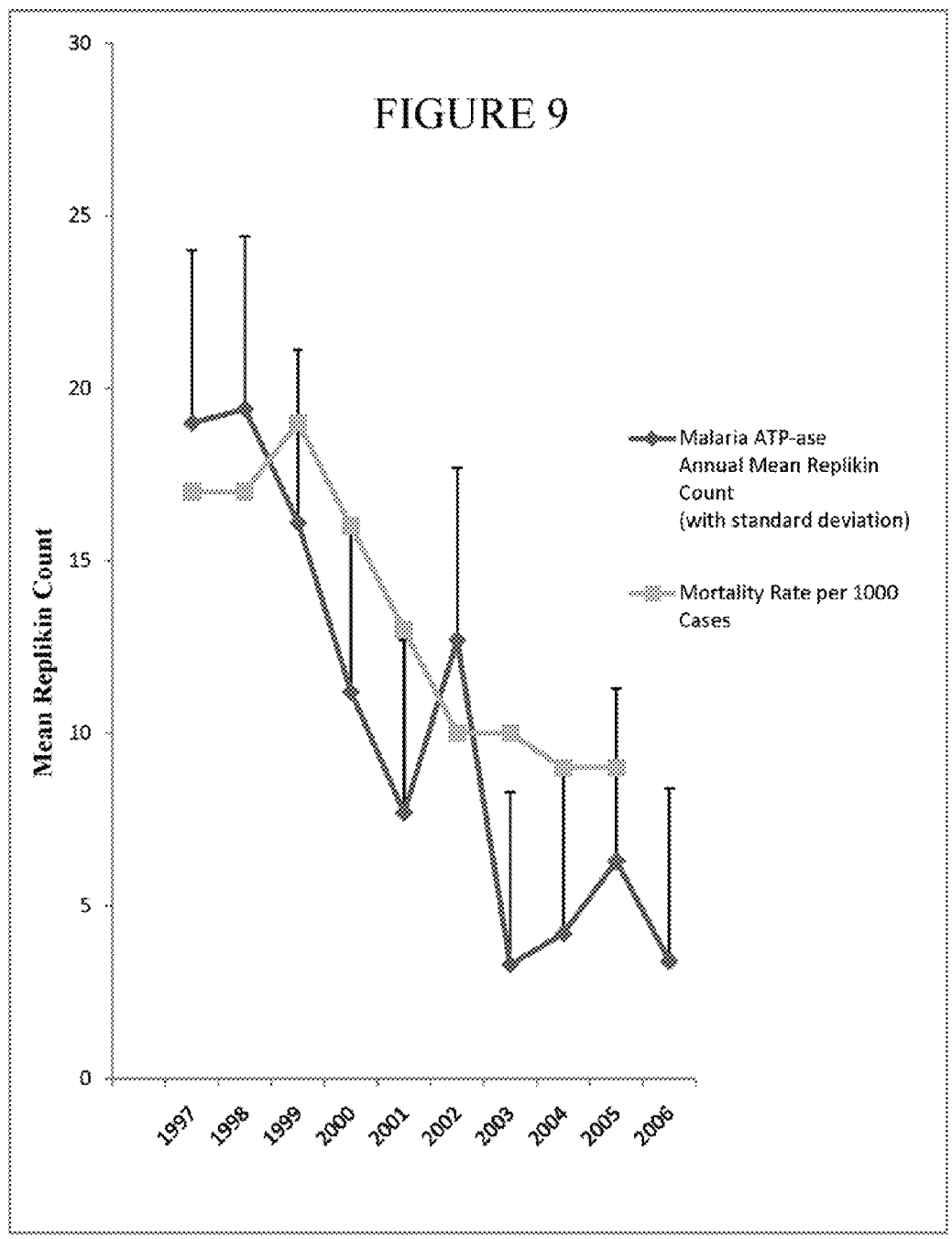

FIG. 9 illustrates that mortality rates per 1000 clinical cases in humans from *Plasmodium falciparum* correlate with Replikin Count in the *P. falciparum* ATP-ase enzyme. High malaria morbidity and mortality rates occurred in the late 1990s and these rates were thought to be due to adaptation of the microorganism and decreased effectiveness of anti-malarials. ATP-ase is a primary target of arteminisin treatment of malaria. With increased use of arteminisin, and improved public health measures, morbidity and mortality rates declined from 1999 to 2006. The Replikin Count of *P. falciparum* ATP-ase increased from 1997 to 1998 along with an increase in mortality per malaria case. The Replikin Count of *P. falciparum* ATP-ase decreased along with mortality rates from 1998 to 2006 (consistent mortality presently available only through 2005). Mortality rates per 1000 human cases of malaria for 1997 to 2005 were as follows: 1997 mortality rate was 17; 1998 mortality rate was 17; 1999 mortality rate was 19; 2000 mortality rate was 16; 2001 mortality rate was 13; 2002 mortality rate was 10; 2003 mortality rate was 10; 2004 mortality rate was 9; and 2005 mortality rate was 9. Mortality rates are recorded as declared by the World Health Organization. See www.who.int.

Figure 10:
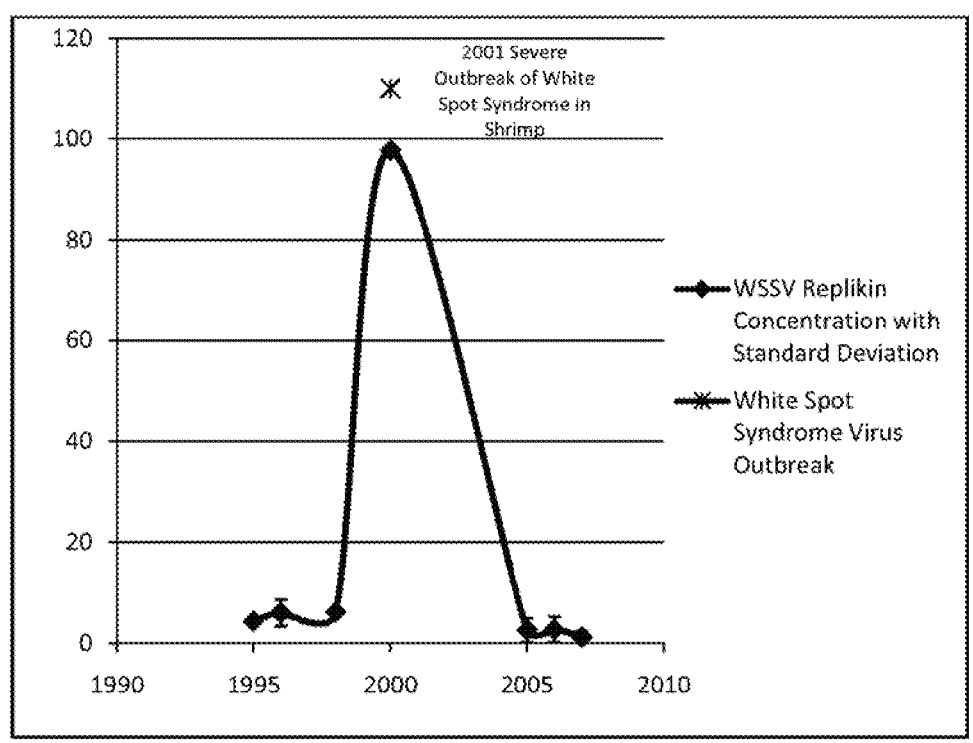

FIG. 10 illustrates a correlation between the mean Replikin Count and standard deviation of Replikin sequences observed in publicly available amino acid sequences of white spot syndrome virus (WSSV) isolated between 1995 and 2007 and a significant outbreak of WSSV in 2001 in shrimp. The Replikin concentration in 2000 of 97.6 foretells the 2001 outbreak. Furthermore, a Replikin concentration of 103.8 was observed in a ribonucleotide reductase protein sequence from a 2000 isolate of WSSV wherein a Replikin Peak Gene was identified with an even higher Replikin concentration of 110.7.

Figure 11:
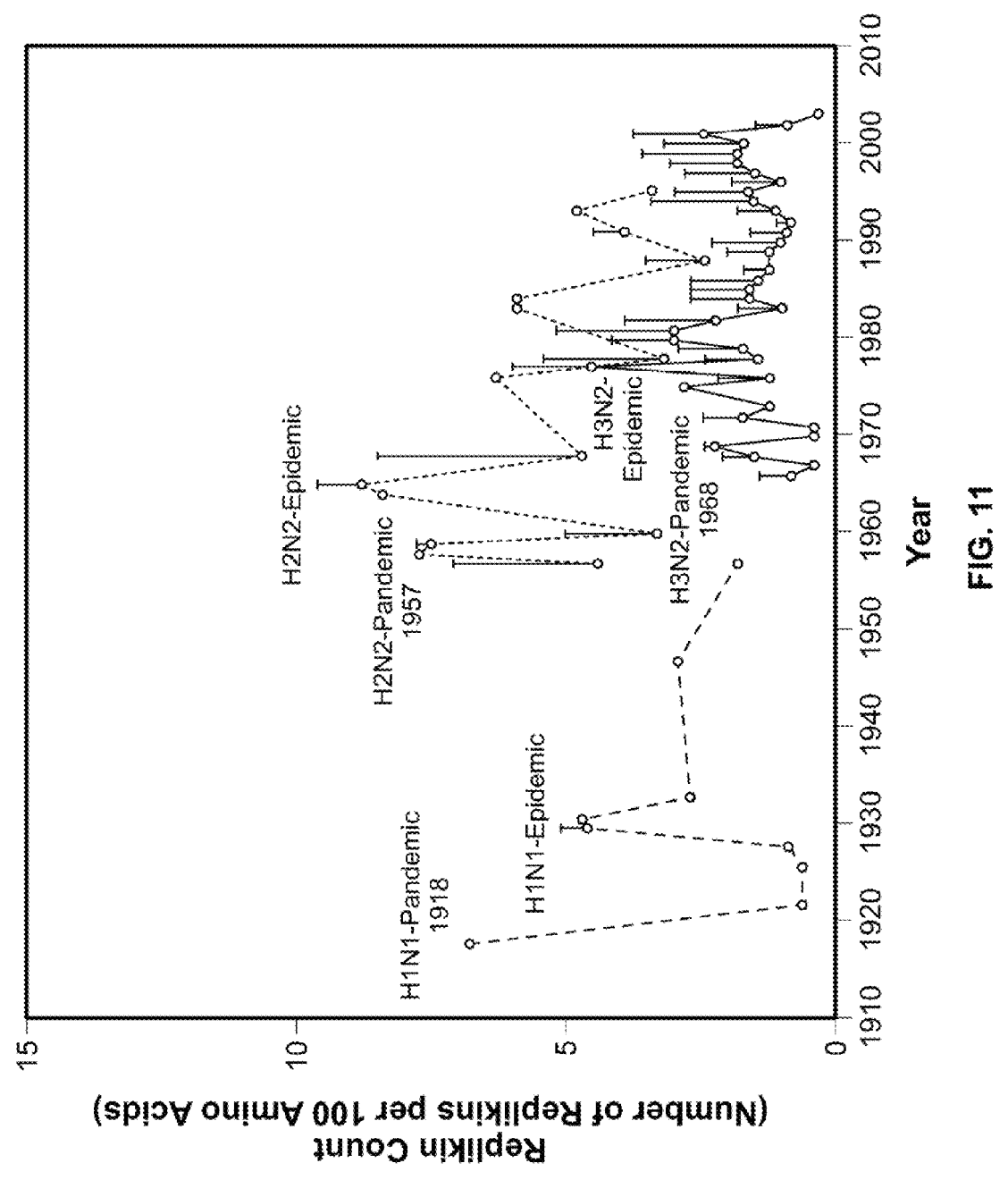

FIG. 11 illustrates total hemagglutinin Replikin Counts in the three influenza pandemics of the last century. Strain-specific high Replikin Counts accompany each of the three pandemics: 1918, 1957, and 1968. In each case, this peak is followed by a decline (likely due to immunity in the hosts), then by a recovery and a "rebound" epidemic. The probability is very low that these correlations are due to chance, since they are specific for each strain, specific for each of the three pandemic years out of the century, specific for each post-pandemic decline, and specific for each rebound epidemic.

FIG. 12 illustrates a relationship between Replikin Counts of Replikin Peak Genes identified within the pB1, pB2, and pA genomic areas of equine influenza 1977-2007 and epidemics of equine encephalitis caused by H3N8 equine influenza. Series 1 reflects the mean Replikin Count identified in the Replikin Peak Gene in the pB1 area of the genome. Series 2 reflects the standard deviation from mean Replikin Count in the pB1 gene area. Series 3 reflects the Replikin Count identified in the Replikin Peak Gene in the pA gene area of the genome, which neighbors the pB1 gene area. Series 4 reflects the Replikin Count identified in the Replikin Peak Gene in the pB2 gene area of the genome, which also neighbors the pB1 gene area. Replikin Count increases in the pB1 gene area are observed to occur one to three years before epidemic outbreaks while no increase in Replikin Count is observed in the pB2 and pA gene areas.

DETAILED DESCRIPTION OF THE INVENTION

Definitions

As used herein, "synthetic peptide" means a peptide produced by a process wherein at least one step in the process is performed outside of a living cell and the process is directly or indirectly initiated or directed by a human.

As used herein, "aquaculture" means cultivation of the natural produce of water, such as cultivation of shellfish.

As used herein, "administer," "administration", or related term means any introduction for therapeutic purposes of a compound to an animal or other subject wherein said introduction may be accomplished through application via the mouth, application to the skin, application through the skin, application through the gills, application via transdermal injection, or application using any other method known to one of skill in the art now and hereafter, whereby the compound is introduced either directly or indirectly into the body of the animal or other subject.

As used herein, a peptide or other compound is "immunogenic" if it is capable, either separately or in combination with other compounds, of stimulating an immune response or a resistance response in a living animal.

As used herein, a compound, treatment, or therapy that stimulates "resistance" or stimulates the development of a "resistant" invertebrate or other animal is a compound, treatment, or therapy that is capable either separately, or in combination with other compounds, treatments, or therapies, of stimulating an immune response or a resistance response in a living animal including, for example, an invertebrate.

As used herein, "therapeutic concentration" means a concentration of a therapeutic agent at which a pathogenic disease is inhibited at a statistically measurable level over at least one life-cycle of the disease.

As used herein, "subtherapeutic concentration" means a concentration of a therapeutic agent at which a pathogenic disease is not inhibited at a statistically measurable level over at least one life-cycle of the disease.

As used herein, "vaccine" means administration to the body of an animal or human a compound capable of stimulating resistance to or an immune response against a pathogen. Administration may be by mouth, gills, transdermal injection, submersion in a concentration of the vaccine or any other method of administration known to one of skill in the art now and hereafter. Details of the immune system of invertebrates such as shrimp, clams, scallops, etc. are not fully understood. For example, shrimp apparently may not produce antibodies. Nevertheless, the phenomenon of resistance to infection is established by the data herein. This resistance may be based in a "primitive immune system." While not being limited by theory, the "primitive immune system" of shrimp and some other invertebrates has been theorized to be similar to the "toll receptor" and related systems in other animals.

As used herein, "animal" includes shrimp and any other animal.

As used herein, "invertebrate" means any animal lacking a spinal column. Invertebrates that are susceptible to aquaculture include but are not limited to mollusks, crustaceans, and echinoderms. Mollusks include but are not limited to clams, mussels, oysters, winkles, scallops, and cephalopods, such as squid, octopus, cuttlefish and terrestrial snails. Crustaceans include but are not limited to shrimp, crab, lobster, prawn, and crayfish. Echinoderms include but are not limited to sea cucumber and sea urchin.

As used herein, "crustacean" is a group of generally aquatic arthropods as understood by one of skill in the art and includes but is not limited to shrimp, crab, lobster, prawn, and crayfish.

As used herein, the term "peptide" or "protein" refers to a compound of two or more amino acids in which the carboxyl group of one amino acid is attached to an amino group of another amino acid via a peptide bond. As used herein, an "isolated" or "purified" peptide or biologically active portion thereof refers to a peptide that is, after purification, substantially free of cellular material or other contaminating proteins or peptides from the cell or tissue source from which the peptide is derived. A "synthetic" or "synthesized" peptide or biologically active portion thereof refers to a peptide that is, after synthesis, substantially free from chemical precursors or other chemicals when chemically synthesized by any method, or substantially free from contaminating peptides when synthesized by recombinant gene techniques.

An "encoded" protein, protein sequence, protein fragment sequence or peptide sequence is a peptide sequence encoded by a nucleic acid sequence that encodes the amino acids of the protein or peptide sequence wherein the nucleic acids encode amino acids using any codon known to one of skill in the art now or hereafter. It should be noted that it is well-known in the art that, due to redundancy in the genetic code, individual nucleotides can be readily exchanged in a codon and still result in an identical amino acid sequence. As will be understood by one of skill in the art, a method of identifying a Replikin amino acid sequence also encompasses a method of identifying a nucleic acid sequence that encodes a Replikin amino acid sequence wherein the Replikin amino acid sequence is encoded by the identified nucleic acid sequence.

As used herein, a Replikin sequence is an amino acid sequence having 7 to about 50 amino acids comprising:
  (1) at least one lysine residue located six to ten amino acid residues from a second lysine residue;
  (2) at least one histidine residue; and
  (3) at least 6% lysine residues.

A Replikin sequence may comprise a terminal lysine and may further comprise a terminal lysine or a terminal histidine. A Replikin peptide or Replikin protein is a peptide or protein consisting of a Replikin sequence. A Replikin sequence may also be described as a Replikin sequence of 7 to about 50 amino acids comprising or consisting of a Replikin motif wherein the Replikin motif comprises (1) at least one lysine residue located at a first terminus of said isolated peptide and at least one lysine residue or at least one histidine residue located at a second terminus of said isolated peptide; (2) a first lysine residue located six to ten residues from a second lysine residue; (3) at least one histidine residue; and (4) at least 6% lysine residues. For the purpose of determining Replikin concentration, a Replikin sequence must have a lysine residue at one terminus and a lysine residue or a histidine residue at the other terminus.

The term "Replikin sequence" can also refer to a nucleic acid sequence encoding an amino acid sequence having 7 to about 50 amino acids comprising:
  (1) at least one lysine residue located six to ten amino acid residues from a second lysine residue;
  (2) at least one histidine residue; and
  (3) at least 6% lysine residues,
wherein the amino acid sequence may comprise a terminal lysine and may further comprise a terminal lysine or a terminal histidine.

As used herein, a Replikin Peak Gene (RPG) or a Replikin Peak Gene Area (RPGA) are used interchangeably to mean a segment of a genome, protein, segment of protein, or protein fragment in which an expressed gene or gene segment has a highest concentration of Replikins (number of Replikin sequences per 100 amino acids) when compared to other segments or named genes of the genome having continuous, non-interrupted and overlapping Replikin sequences. Generally, the gene or gene segment associated with a whole protein or protein-expressing gene is known as the Replikin Peak Gene and the gene or gene segment associated with a protein fragment is known as a Replikin Peak Gene Area. More than one RPG or RPGA may be identified within a gene, gene segment, protein or protein fragment. An RPG or RPGA may have a terminal lysine or a terminal histidine, two terminal lysines, or a terminal lysine and a terminal histidine. An RPG or RPGA may likewise have neither a terminal lysine nor a terminal histidine so long as it contains a Replikin sequence or Replikin sequences defined by the definition of a Replikin sequence, namely, an amino acid sequence having 7 to about 50 amino acids comprising:
  (1) at least one lysine residue located six to ten amino acid residues from a second lysine residue;
  (2) at least one histidine residue; and
  (3) at least 6% lysine residues.

As used herein, "emerging strain" refers to a strain of a virus or other pathogen identified as having an increased or increasing concentration of Replikin sequences in one or more of its protein sequences relative to the concentration of Replikins in other strains of such organism. An emerging strain of virus indicates an increase in virulence or replication.

As used herein, "outbreak" is an increase in virulence, morbidity or mortality in a viral disease as compared to an earlier-arising epidemiological pattern of infection in the same viral disease.

As used herein, "Replikin Count" or "Replikin concentration" refers to the number of Replikins per 100 amino acids in a protein, protein fragment, virus or organism. A higher Replikin concentration in a first strain of virus or organism has been found to correlate with more rapid replication of the first virus or organism as compared to a second, earlier- or later-arising strain of the virus or organism having a lower Replikin concentration.

As used herein a "Replikin Scaffold" refers to a series of conserved Replikin peptides wherein each of said Replikin peptide sequences comprises about 16 to about 34 amino acids and preferably about 28 to about 33 amino acids and further comprises: (1) a terminal lysine and optionally a lysine immediately adjacent to the terminal lysine; (2) a terminal histidine and optionally a histidine immediately adjacent to the terminal histidine; (3) a lysine within 6 to 10 amino acid residues from another lysine; and (4) about 6% lysine. "Replikin Scaffold" also refers to an individual member or a plurality of members of a series of Replikin Scaffolds.

In a taura syndrome virus, a Replikin Scaffold may refer to a Replikin peptide sequence comprising about 16 to about 34 amino acid residues, preferably about 27 to about 33 amino acid residues and more preferably about 30 to 33 amino acid residues. In an influenza virus, a Replikin Scaffold may refer to a Replikin peptide sequence comprising about 16 to about 34 amino acid residues and more preferably about 28 to about 30 amino acid residues. In a White Spot Syndrome Virus, a Replikin Scaffold may refer to a Replikin peptide sequence comprising about 16 to about 34 amino acid residues and more preferably about 27 to about 29 amino acid residues.

As used herein, the "life cycle" of a shrimp extends substantially from the time when a shrimp is capable of consuming food by mouth until the shrimp is harvested.

As used herein, "time periods" or "time points" is any two time periods or points that may be differentiated one from another. For example, an isolate of virus isolated during the year 2004 is isolated in a different time period than an isolate of the same virus isolated during the year 2005. Likewise, an isolate of virus isolated in May 2004 is isolated in a different time period than an isolate of the same virus isolated in June 2004.

Replikin Sequences as Therapeutic Compounds in Invertebrates including Shrimp

The inventors have identified Replikin sequences in the genome of pathogens to invertebrates in aquaculture including Replikin sequences in the genome of taura syndrome virus (TSV) as therapeutic compounds against viral, bacterial and protozoic diseases in invertebrates such as shrimp, scallops, oysters, lobsters, etc. The identified therapeutic compounds stimulate resistance in the invertebrates challenged with the pathogen such as *Chlamydia*-like, *Rickettsia*-like, *Vibrio*, taura syndrome virus, white spot syndrome virus, and other pathogens. The identified sequences are isolated or synthesized Replikin peptides consisting of 7 to about 50 amino acids comprising a Replikin motif comprising (1) at least one lysine residue located at a first terminus of the motif and at least one lysine residue or at least one histidine residue located at a second terminus of the motif, (2) a first lysine residue located six to ten residues from a second lysine residue, (3) at least one histidine residue; and (4) at least 6% lysine residues wherein said isolated or synthesized peptides are isolated or synthesized by selecting the identified motif and isolating or synthesizing said peptide comprising said motif. In a further embodiment, the Replikin peptide consists of the Replikin motif. The skilled artisan will understand how to isolate and synthesize Replikin peptides using the above-described method. Any method of producing peptides of known structure may be used.

Replikin peptides have been related to rapid replication in plants, animals, bacteria, viruses, trypanosomes and other living things. See U.S. Pat. Nos. 7,176,275 and 7,189,800. Replikins have further been correlated with virulence, morbidity, and mortality in pathogens such as influenza, West Nile virus, malaria, white spot syndrome virus, and taura syndrome virus. See FIGS. 6-12. Additionally, Replikin sequences have been shown to be immunogenic and/or resistance stimulating, or both, in all tests or studies undertaken to date including in chickens, rabbits, shrimp and humans. See U.S. application Ser. No. 11/355,120, filed Feb. 16, 2006 (Examples 6 and 7), U.S. Pat. No. 6,638,505. Additionally, the concentration of Replikin sequences in the genome of a pathogen (or in an area of particular interest in the genome of a pathogen known as the Replikin Peak Gene) has been correlated with pathogenic outbreaks, morbidity and mortality. See FIGS. 3-12. In particular, Replikin concentration has been correlated with mortality in invertebrates (shrimp) in taura syndrome virus and with pathogenic outbreaks in invertebrates (in shrimp) in both taura syndrome virus and white spot syndrome virus. See FIGS. 3-6 and 10. Replikin sequences have been widely associated with virulence, morbidity, and mortality and have consistently been associated with immunogenicity and resistance including in horses, rabbits, chickens, humans, and shrimp. These wide-ranging data provide support for vaccines containing Replikin sequences including support for vaccines containing Replikin sequences from pathogens in aquaculture.

The isolated or synthesized Replikin peptides identified in a pathogen to an invertebrate in aquaculture are then fed, injected, otherwise administered to the invertebrate such as shrimp, scallops, oysters, lobsters, etc. as a prophylactic against possible outbreaks of pathogenic diseases including TSV or other pathogenic disease, prior to a predicted outbreak of the disease or during an outbreak of the disease. The peptides may be administered to the invertebrate alone or in combination with regular feed or with supplemental feed formulated for carrying the peptides. The skilled artisan will understand that any method of formulating feed may be used that provides the Replikin sequences to the invertebrate per os. A stabilizer or preservative or both may be added to a mixture of Replikin sequences or a mixture of Replikin sequences and invertebrate feed to maintain a therapeutically effective ration for feeding of and treatment of cultured invertebrates over a period of time, including shrimp, scallops, oysters, clams, crabs, abalone, lobster, etc. The skilled artisan will understand extensive options of methods of stabilizing short peptides in feed and in therapeutic mixtures.

Administration of peptides may be at therapeutic or sub-therapeutic levels before or after infection occurs. Administration may also be made to chronically infected populations.

Any Replikin identified in the genome of or identified as expressed by the pathogen may be administered as a therapeutic compound to stimulate a resistance response in shrimp. The following exemplary sequences may be fed alone or in any combination to shrimp as a vaccine against taura syndrome virus: KVGSRRYKSH (SEQ ID NO: 1), HFATKCF-GEVPKK (SEQ ID NO: 2), KAENEFWDGVKQSH (SEQ ID NO: 3), KGHRKVPCEQK (SEQ ID NO: 4), HRKVPCEQK (SEQ ID NO: 5), KVPCEQKIWLH (SEQ ID NO: 6), KIWLHQNPGK (SEQ ID NO: 7), HQNPGK-TQQDMK (SEQ ID NO: 8), KGNTRVHVK (SEQ ID NO: 9), KEHVEKIVDK (SEQ ID NO: 10), or HVEKIVDKAK (SEQ ID NO: 11). The exemplary sequences, as with all taura syndrome virus Replikin sequences, including Replikin sequences and Replikin Scaffold sequences as discussed below, may be fed, or used in an immersion method of administration or injected. The sequences may be administered individually or in any combination including in an equal combination of peptides by weight. Any Replikin sequence or immunogenic sequence of about 7 to about 50 amino acids may be used as a compound for administration to an invertebrate including use as a vaccine. For example, SEQ ID NOS: 1-11, 86, 87, 103-112, 114-198 may each be used alone or in combination as a compound for administration to an invertebrate against TSV infection.

Reduction of Viral Load and Dose-Response Curves

Immunogenic or resistance-stimulating synthetic peptides may be administered to invertebrates at about 0.001 mg to about 10 mg of synthetic peptide per gram of body weight of each treated invertebrate per day, at about 0.005 mg to about 5 mg of synthetic peptide per gram of body weight of each treated invertebrate per day, at about 0.01 mg to about 2 mg of synthetic peptide per gram of body weight of each treated invertebrate per day, at about 0.02 mg to about 1.5 mg of synthetic peptide per gram of body weight of each treated invertebrate per day, at about 0.08 mg to about 1.0 mg of synthetic peptide per gram of body weight of each treated invertebrate per day, at about 0.1 mg to about 0.9 mg of synthetic peptide per gram of body weight of each treated invertebrate per day, at about 0.2 mg to about 0.8 mg of synthetic peptide per gram of body weight of each treated invertebrate per day, at about 0.5 mg of synthetic peptide per gram of body weight of each treated invertebrate per day. One of skill in the art will understand how to determine dosage of synthetic peptide that is appropriate for therapeutic or sub-therapeutic administration.

TSV vaccine doses containing a mixture of peptides by equal weight have now been tested in shrimp and shown to provide a protective effect. The following peptides have been tested: KVGSRRYKSH (SEQ ID NO: 1), HFATKCFGEV-PKK (SEQ ID NO: 2), KAENEFWDGVKQSH (SEQ ID NO: 3), KGHRKVPCEQK (SEQ ID NO: 4), HRKVPCEQK (SEQ ID NO: 5), KVPCEQKIWLH (SEQ ID NO: 6), KIWL-HQNPGK (SEQ ID NO: 7), HQNPGKTQQDMK (SEQ ID NO: 8), KGNTRVHVK (SEQ ID NO: 9), KEHVEKIVDK (SEQ ID NO: 10), and HVEKIVDKAK (SEQ ID NO: 11). The vaccine has been given in different experiments at approximately 0.02, 0.08 and 0.50 mg of Replikin vaccine per one gram of body weight of tested shrimp per day. The doses are approximate because of individual differences in individual shrimp consumption. Taken orally by shrimp weighing 1 g to 4 g, all three dose levels have been well tolerated, and all produced statistically significant lower viral loads in the shrimp as compared to unvaccinated controls. The 0.08 mg and the 0.5 mg doses provided statistically significant protection. The lowest dose of 0.02 mg, in one of two experiments, gave protection which did not reach statistical significance; nevertheless, as demonstrated above, statistically significant lower viral loads were observed. The 0.50 mg per "shrimp-gram" dose (the highest dose tested to date) provided the best statistically significant protection of 91%. Therefore, from the results to date, it appears that doses of 0.50 mg per "shrimp-gram," and possibly higher, are preferred embodiments of an aspect of the invention.

Production of Vaccine in About Seven Days or Less

Another non-limiting aspect of the present invention provides a method of producing a vaccine wherein at least one Replikin sequence is identified in a pathogen and the at least one Replikin sequence is chemically synthesized as an active agent of the vaccine. The inventors have successfully produced such an effective vaccine in seven days or fewer from the time a pathogen is identified.

Once a pathogen is identified, its genome is determined. The artisan then surveys the genome for Replikin sequences using, for example, ReplikinsForecast™ (Replikins LLC, Boston, Mass.). Once Replikin sequences have been identified, any one or more Replikin sequence may be chosen for chemical synthesis. A preferred Replikin sequence may be a Replikin sequence identified in a Replikin Peak Gene. Chemical synthesis of the identified at least one Replikin sequence is undertaken as understood by one of skill in the art.

The synthetic peptide or peptides are then administered to a host of the pathogen. Administration of the vaccine may be orally, mixed with a food source for oral consumption, through the gills, in a concentrated emersion wherein the vaccine is absorbed into the body through the gills, skin, mouth, etc., via injection, or using any other method known to one of skill in the art now and hereafter. The vaccine may be combined with a pharmaceutically acceptable carrier, excipient, binder, or other helpful compound, adjuvant, solution or mixture known to one of skill in the art.

The process is easily accomplished in seven days or fewer based on the ease of identification of Replikin sequences in a genome of a pathogen and the ease of chemical synthesis of peptides in large volumes. This novel process of providing effective active ingredient for vaccines in seven days or fewer solves a critical problem in the art because current methods of production of vaccines generally requires three to twelve months. This delay in vaccine production may deliver vaccine after an epidemic has long since ended or, if still active, after mutations in the pathogen have rendered the vaccine less effective or useless. The long process of vaccine development is a significant worry among health professionals and government. The inventors have now provided a method for greatly reducing delay in vaccine development.

Development of Resistant Lines of Cultured Invertebrates

Another non-limiting aspect of the present invention provides a method of increasing resistance of an invertebrate to a pathogen comprising:

(1) challenging a plurality of invertebrates being of the same species as said invertebrate with said pathogen at sufficient levels to cause disease in at least one individual of the plurality of said invertebrates;

(2) discarding at least one individual of the plurality said invertebrates that is diseased or dead;

(3) repeating steps (1) and (2) at least once; and (4) at least once administering to the plurality of said invertebrates the substance of claim 1 in steps (1), (2) and/or (3) which increases the resistance of said invertebrate to the pathogen.

The process may be repeated a number of times until a desired level of survival is observed in the cultured invertebrates including 100% survival. The cultured resistant invertebrates may then be used as breeding stock for production of resistant lines of invertebrates for aquaculture. The compound comprising an immunogenic peptide may be administered at each repetition of steps 1 and 2, may be administered in the second repetition of steps 1 and 2, or may be administered at some later repetition of steps 1 and 2. As demonstrated in Example 3 below and in FIG. 2, shrimp chronically infected with taura syndrome virus prior to administration of about 0.5 mg per gram of shrimp body weight of a compound comprising eleven taura syndrome virus immunogenic peptides by equal weight provided 91% survival of shrimp challenged with TSV. In contrast only 25% of shrimp that had not been previously challenged with TSV and had not been administered vaccine survived the challenge. Further, 75% of shrimp chronically infected with TSV not administered vaccine additionally survived the challenge.

The trials reported in Example 3 and FIG. 2 demonstrate that refractory resistance in combination with vaccine treatment has to date provided the highest observed protection against challenge from TSV. As such, one aspect of the invention provides a method of increasing resistance using cycled challenge of invertebrates with a chosen pathogen in combination with administration of a vaccine. In a preferred embodiment, the at least one isolated or synthetic peptide of the vaccine is a Replikin peptide. Replikin peptides have been demonstrated to stimulate immunogenic and/or resistance responses in vertebrates and invertebrates. For example, vaccine products against SARS Replikin sequences and H5N1 influenza virus Replikin Scaffolds have been demonstrated, see, e.g., U.S. application Ser. No. 11/355,120, filed Feb. 16, 2006 (Examples 6 and 7), all Replikin sequences tested in rabbit or chicken have induced an immune response, and the glioma Replikin sequence has been identified in cancer cells and isolated with or synthesized into peptides that induce an immune response in rabbits and react with natural antibody responses in humans. See U.S. Pat. No. 6,638,505.

Conservation of Replikin Structure Relates to Virulence and Lethality

The conservation of any structure is critical to whether that structure provides a stable invariant target to attack and destroy or to stimulate. Replikin sequences have been shown to generally be conserved. When a structure is tied in some way to a basic survival mechanism of the organism, the structures tend to be conserved. A varying structure provides an inconstant target, which is a good strategy for avoiding attackers, such as antibodies that have been generated specifically against the prior structure and thus are ineffective against the modified form. This strategy is used by influenza virus, for example, so that a previous vaccine may be quite ineffective against the current virulent virus.

Certain structures too closely related to survival functions, however, apparently cannot change constantly. An essential component of the Replikin structure is histidine (h), which is known for its frequent binding to metal groups in redox enzymes and is a probable source of energy needed for replication. Since the histidine structure remains constant, Replikin sequence structures remain all the more attractive a target for destruction or stimulation. Additionally, as demonstrated below in Tables 1 and 2, Replikin structures generally are conserved throughout virulent pathogens including pathogens to invertebrates.

In view of the conservation of Replikin structures in invertebrate pathogens, an aspect of the present invention provides an antibody or antibody fragment or anti-Replikin small molecule to at least one isolated or synthesized Replikin sequence within a protein or protein fragment of a pathogen in aquaculture or within a Replikin Peak Gene or within a protein or gene area comprising a Replikin Peak Gene in a pathogen in aquaculture. Antibodies to Replikins and anti-Replikin small molecules are useful as therapies against pathogenic outbreaks. Following identification of Replikin sequences in a pathogen, one of skill in the art knows many ways of developing antibodies or antibody fragments for therapeutic and diagnostic purposes. One of skill in the art likewise knows how to produce small molecules to bind identified Replikin sequences.

Replikin Scaffolds as Therapeutic Targets and Predictors

The inventors have established in strains of influenza, in White Spot Syndrome Virus and in taura syndrome virus, that the presence of Replikin Scaffolds is predictive of epidemics. As such, in addition to the total number of Replikins in a virus, the structure of each Replikin through time is informative and Replikin Scaffolds provide a particularly useful target for identifying and controlling rapid replication including outbreaks of pathogenic diseases in invertebrates in aquaculture, including shrimp. Table 1, below, shows a Replikin Scaffold first observed in a goose infected with influenza in 1917 (Goose Replikin). Constant length, constant lysines at the amino terminal and histidine residues at the carboxy terminal were conserved in different strains in a fixed scaffold for decades. Homologues of the Goose Replikin appeared from 1917 through 2006 in strains including each strain responsible for the three pandemics of 1918, 1957, and 1968, H1N1, H2N2 and H3N2. Homologues with further substitutions are also observed in H1N2, H7N7, H5N2 and H5N1.

TABLE 1

Replikin Scaffold showing ordered substitution in the 89 year conservation of influenza virus Replikin peptides related to rapid replication, from a 1917 goose influenza Replikin and the 1918 human pandemic Replikin to 2006 H5N1 "Bird Flu" homologues. (SEQ ID NOS: 12-74, respectively, in order of appearance)

| [<---------------29 Amino Acids------------->] | Year | Strain |
|---|---|---|
| kkgtsypklsksytnnkgkevlvlwgvhh | 1917 | H1N_ Influenza Goose Replikin |
| kkgssypklsksynnkgkevlvlwgvhh | 1918 | H1N1 Human Influenza Pandemic |
| kkensypklsksynnkgkevlvlwgvhh | 1930 | H1N1 |
| kkgdsypkltnsynnkgkevlvlwgvhh | 1933 | H0N1 |
| kkgtsypklsksytnnkgkevlvlwgvhh | 1976 | H1N1 |
| kkgtsypklsksytnnkgkevlvlwgvhh | 1977 | H1N1 |
| kkgnsypklsksytnnkgkevlviwgvhh | 1979 | H1N1 |
| kkgnsypklsksytnnkgkevlviwgvhh | 1980 | H1N1 |
| kkgtsypklsksytnnkgkevlvlwgvhh | 1980 | H1N1 |
| kkgnsypklsksytnnkgkevlviwgvhh | 1981 | H1N1 |
| kkgnsypklsksytnnkgkevlvlwgvhh | 1981 | H1N1 |
| kkgtsypklsksytnnkgkevlvlwgvhh | 1985 | H1N1 |
| kkgnsypklsksytnnkgkevlviwgvhh | 1991 | H1N1 |
| kkgnsypklsksytnnkgkevlviwgvhh | 1992 | H1N1 |
| kkgnsypklsksytnnkgkevlviwgvhh | 1996 | H1N1 |
| kkgdsypklsksytnnkgkevlviwgvhh | 1996 | H1N1 |
| kkgssypklsksynnkgkevlvlwgvhh | 1997 | H1N1 |
| kkgssypklsksynnkgkevlvlwgvhh | 1998 | H1N1 |
| kkgnsypklsksytnnkgkevlviwgvhh | 1999 | H1N1 |
| kkgnsypklsksytnnkgkevlviwgvhh | 2000 | H1N1 |
| kkgnsypklsksytnnkgkevlviwgvhh | 2001 | H1N1 |
| kkgnsypklsksytnnkgkevlviwgvhh | 2002 | H1N1 |
| kkgnsypkisksynnkekevlvlwgihh | 1999 | H1N2 Influenza |
| kkgnsypklsksynnkkkevlviwgihh | 2000 | H1N2 |
| kkgnsypklsksynnkgkvlvlwgihh | 2001 | H1N2 |
| kkgtsypklsksytnnkkkevlvlwgvhh | 2001 | H1N2 |
| -kngtypnlsksyannkekevlvlwgvhh | 2002 | H1N2 |
| -kngtypnlsksyannkekevlilwgvhh | 2002 | H1N2 |
| kkgpnypyakrsynntsgegmlilwgvhh | 1957 | H2N2 Human Influenza Pandemic |
| kkgpnypyakrsynntsgegmlilwgvhh | 1957 | H2N2 Human Influenza Pandemic |
| kkensypklrksiinkkevklvlwgihh | 1968 | H3N2 Human Influenza Pandemic |

TABLE 1-continued

Replikin Scaffold showing ordered substitution in the 89 year conservation of influenza virus Replikin peptides related to rapid replication, from a 1917 goose influenza Replikin and the 1918 human pandemic Replikin to 2006 H5N1 "Bird Flu" homologues. (SEQ ID NOS: 12-74, respectively, in order of appearance)

| [<---------------29 Amino Acids------------>] | Year | Strain |
|---|---|---|
| ----------ksykntikdpalidlwgihh | 1979-2003 | H7N7 Influenza |
| kknnaypтikrtynntnvedlillwgihh | 2002 | H5N2 Influenza |
| kknnaypтikrsynnтnqedllvlwgihh | 1959 | H5N1 Influenza (Scotland) |
| kknnaypтikrtynntniedllilwgihh | 1975 | H5N1 (Wisconsin) |
| kknnaypтikrtynntnmedllilwgihh | 1981 | H5N1 (Minnesota) |
| kkgnaypтikrtynntnvedllilwgihh | 1983 | H5N1 (Pennsylvania) |
| kknntypтikrsynntnqedllilwgihh | 1988 | H5N1 (Scotland) |
| kknsaypтikrsynntnqedllvlwgihh | 1996 | H5N1 (China) |
| kknsaypтikrsynntnqedllvlwgihh | 1997 | H5N1 (China) |
| kknsaypтikrsynntnqedllvlwgihh | 1998 | H5N1 (China) |
| kknsaypтikrsynntnqedllvlwgihh | 1999 | H5N1 (China) |
| kknsaypтikrsynntnqedllvlwgihh | 2000 | H5N1 (China) |
| kknsaypтikrsynntnqedllvlwgihh | 2001 | H5N1 (China) |
| kknnaypтikrsynntnqedllvlwgihh | 2001 | H5N1 (China) |
| kknsaypтikrsynntnqedllvlwgihh | 2002 | H5N1 (China) |
| kknstypтikrsynntnqedllvlwgihh | 2002 | H5N1 (Thailand) |
| kknstypтikrsynntnqedllvlwgihh | 2002 | H5N1 (Vietnam) |
| kknstypтikrsynntnqedllvlwgihh | 2003 | H5N1 (Vietnam) |
| kknstypтikrsynntnqedllvlwgihh | 2003 | H5N1 (Thailand) |
| kknstypтikrsynntnqedllvlwgihh | 2003 | H5N1 (Sindong, China) |
| kknnaypтikrsynntnqedllvlwgihh | 2003 | H5N1 (China) |
| kknstypтikrsynntnqedllvnwgihh | 2004 | H5N1 (Vietnam, highly pathogenic) |
| kknsaypтikrsynntnqedllvlwgihh | 2004 | H5N1 (Vietnam, highly pathogenic, gull) |
| kknstypтikrsynntnqedllvlwgihh | 2004 | H5N1 (Vietnam highly pathogenic) |
| kknstypтikrsynntnqedllvlwgihh | 2004 | H5N1 (Thailand, highly pathogenic) |
| kknstypтikrsynntnqedllvlwgiqh | 2004 | H5N1 (Thailand, highly pathogenic) |
| kknsaypiikrsynntnqedllvlwgihh | 2004 | H5N1 (China, highly pathogenic) |
| kknsaypтikrsxntnhedllvlwgihh | 2004 | H5N1 (China, highly pathogenic, goose) |
| kknsaypтikrsynntnqedllvlwgihh | 2004 | H5N1 (Japan) |
| kknnaypтikrsynntnqedllvlwgihh | 2005 | H5N1 (Turkey) |
| kknntypтikksynntnhedllvlwgihh | 2006 | H5N1 (China, Anhui) |
| kknstypтikrsynntnqedllvnwgihh | 2006 | H5N1 (Indonesia, highly pathogenic) |

*Residues identical to Goose Replikin amino acids are unshaded; amino acid substitutions are shaded lightly and darkly to show scaffold pattern across years and strains. Substitution at position 24 in 2004 and 2006 H5N1, 1957 H2N2, 1968 H3N2 and H7N7 are boxed.

Table 1 illustrates the history, by year or smaller time period, of the existence in the protein structure of the Goose Replikin and its homologues in other influenza Replikins. Table 1 further illustrates the history of amino acid substitutions in those homologues and the conservation of certain amino acids of the Replikin structure that are essential to the definition of a Replikin and the function of rapid replication supplied by Replikins.

A review of Table 1 illustrates that if random substitution of amino acids were to occur in virulent strains of influenza from 1917 through the present, certain framework amino acids of the Goose Replikin would not be conserved from year to year in strains in which epidemics occurred. However, contrary to what would result from random substitution, virulent strains of influenza from year to year consistently contain conserved amino acids at those positions that define a Replikin. That is, if a substitution were to occur in one of the amino acids that define a Replikin, e.g. lysine or a histidine, the definition of the Replikin would be lost. Nevertheless, the Replikin sequence is conserved over more than 89 years. Thus, since there is conservation of certain amino acids over decades, substitution cannot be said to be completely at random. The fact that substitutions do occur in amino acids that are not essential to the definition of a Replikin (i.e., amino acids other than lysines or histidines) demonstrates the importance of the Replikin and the Replikin Scaffold in the pathogenicity of the strain.

It may be further noted from Table 1 that when substitutions do occur, they are seen to occur at certain apparently preferred positions of the Replikin Scaffold. Table 1 illustrates recurring substitutions at positions 1, 3-24 and 26-27. Further, while substitutions occur throughout these positions, a lysine continues to exist at a position 6 to 10 amino acids from a second lysine (which has not been substituted in these virulent strains).

As seen in Table 1, even when there is a substitution of a lysine position within the 29 amino acid stretch, as is seen in 1957, when K at position 11 shifts to position 10, that new position is maintained until 2005. Additionally, YP (at positions 6-7), SY (at positions 12-13), N (at position 15), and LVLWG (SEQ ID NO: 75) (at positions 22-26) conserve the homologous structure of the Replikin Scaffold with few exceptions.

Homologous Replikin Scaffold Sequences in Influenza, WSSV, and TSV

The inventors have further established a relationship between virulent influenza virus and TSV and white spot syndrome virus (another viral pathogen in shrimp) in the Replikin Scaffold portions of the viruses as may be seen in Table 2 below. Although there is extensive substitution, several short Replikins of the white spot syndrome virus demonstrate significant homologies to the influenza virus Replikin sequences, especially with regard to length and key lysine (k) and histidine (h) residues. Similar, but less extensive homologies are seen in taura syndrome virus. These homologies suggest that the sequences are derived from a shared reservoir and/or that similar mechanisms of Replikin production are used in both virus groups and are significant to virulence in each of the viruses in which the homologues are shared. Because Replikin structure appears to be conserved within a reservoir or within a shared mechanism, it is no surprise that the relationship of the Replikin structure to rapid replication, virulence, mortality, and morbidity appears to be conserved across a wide-range of pathogens and hosts including pathogens in invertebrates in aquaculture including shrimp, scallops, clams, crabs, mussels, etc.

TABLE 2

Shrimp White Spot and Taura Syndrome Scaffolding (SEQ ID NOS 76-87, respectively, in order of appearance)

| Sequence | Year | Virus |
|---|---|---|
| kkgtsypklsksytnnkgkevlvlwgvhh | 1917 | H1N_ Influenza goose peptide |
| kkgnsypklsksytnnkgkevlvlwgvhh | 2002 | H1N1 Swine Influenza |
| kknvksakqlphlkvlkkldvrgakqlph | 2000 | Shrimp White Spot Syndrome Virus |
| -kvhldvkgvkqllhlkvrldvrgakqlh | 2000 | Shrimp White Spot Syndrome Virus |
| kkensypklrksiiinkkevklvlwgihh | 1968 | H3N2 Human Influenza Pandemic |
| ---------keykntrkdpaliiwgihh | 1979-2003 | H7N7 Influenza |
| kkgpnypvakrsynntsgeqmliiwgvhh | 1957 | H2N2 Human Influenza Pandemic |
| kkgpnypvakrsynntsgeqmliiwgihh | 1957 | H2N2 Human Influenza Pandemic |
| kknnayptikrtynntnvedlliiwgihh | 2002 | H5N2 Influenza |
| kknnayptikrsysntngedlivlwgihh | 1959 | H5N1 Influenza |
| kkvqanktrvfaasnqglalalrryylsfldh | 2000 | Taura Syndrome Virus |
| kkacrnagykeaclheldcksfllaqqgragah | 2005 | Taura Syndrome Virus |

Residues identical to original 1917 Goose Replikin residues are shown in medium grey, Amino acid substitutions in light grey and dark grey.

Replikin and Replikin Scaffold Therapeutic Compounds

Another aspect of the invention provides a method of making a preventive or therapeutic compound comprising identifying a Replikin Scaffold comprising about 16 to about 34 amino acids and isolating or synthesizing said Replikin Scaffold for use as a preventive or therapeutic treatment against pathogens in invertebrate aquaculture wherein said Replikin Scaffold comprises: (1) a terminal lysine and a lysine immediately adjacent to the terminal lysine; (2) a terminal histidine and a histidine immediately adjacent to the terminal histidine; (3) a lysine within about 6 to about 10 amino acids from another lysine; and (4) at least 6% lysines. The Replikin Scaffold may consist of 27 to about 33 amino acids and may further consist of about 30 to about 33 amino acids. In a further non-limiting embodiment, the Replikin Scaffold consists of 32 or 33 amino acids.

In another aspect of the invention, a preventive or therapeutic compound is provided comprising at least one isolated or synthesized Replikin sequence from a pathogen of an invertebrate cultured for food in water including taura syndrome virus and white spot syndrome virus in shrimp, and *Chlamydia*-like and *Rickettsia*-like bacterial pathogens in mussels, claims, scallops, etc. In a non-limiting embodiment of the invention, a preventive or therapeutic compound is provided comprising at least one Replikin sequence or at least one Replikin Scaffold sequence isolated or synthesized from a pathogen such as TSV. In a non-limiting embodiment of the invention, the at least one isolated or synthesized Replikin sequence or at least one Replikin Scaffold sequence is present in an emerging strain of a pathogen such as TSV. In a further non-limiting embodiment of the invention, the preventive or therapeutic compound comprises two or more Replikin sequences. In a further non-limiting embodiment, the preventive or therapeutic compound comprises two or more Replikin Scaffold sequences. In a further non-limiting embodiment, the preventive or therapeutic compound comprises at least one Replikin sequence and at least one Replikin Scaffold sequence. In another non-limiting embodiment, the preventive or therapeutic compound comprises at least one Replikin sequence or at least one Replikin Scaffold sequence and a pharmaceutically acceptable carrier.

EXAMPLE 1

Comparison of the Replikin Concentration of Four Strains of Taura Syndrome Virus by an Independent Laboratory The Replikin concentrations of the protein sequences of four taura syndrome virus (TSV) isolates from Hawaii, Belize, Thailand and Venezuela, respectively, were examined without knowledge of the exact order of virulence of the four isolates, and the virulence was ranked quantitatively in the order of the Replikin concentrations. The virulence of the four TSV isolates was compared in an independent laboratory, without knowledge of the exact order of the Replikin concentrations. The virulence was compared through a per os laboratory infection in juvenile *Litopenaeus vannamei* (Kona stock, Oceanic Institute, Hawaii). The results showed that the Belize isolate is the most virulent, the Thailand isolate is the second most virulent, followed by the Hawaii isolate, and the Venezuela isolate, which is the least virulent. This is based on the analyses of cumulative survivals at the end of a bioassay and based on the time of 50% mortality. TSV infection as the cause of death was confirmed by positive reactions in RT-PCR detection and by the appearance of characteristic lesions observed in histological analysis. The correlation of Replikin concentrations with virulence as indicated by Mortality Rate was quantitative and substantially linear.

CHALLENGE METHODS

Small juveniles of specific-pathogen-free *Litopenaeus vannamei* (20 shrimp per tank, mean weight: 1.8 g) were fed minced TSV-infected tissues (infected separately with each of the 4 isolates originating from Belize, Thailand, Venezuela and Hawaii) for 3 days at 5% of their body weight. These shrimp were maintained with pelleted ration (Rangen 35%) for the following 12 days. Each challenge bioassay of a specific isolate was triplicated. During the bioassay period, all tanks were checked daily for dead or moribund shrimp. All mortalities were removed from the tank and frozen. One to three moribund shrimp from each isolate were preserved in Davidson's AFA fixative and processed for routine histology to confirm viral infection. For each isolate, six moribund shrimp were collected during the acute phase infection and total RNA was extracted from their gill tissues with a High Pure RNA tissue kit (Roche). The extracted RNA was analyzed for the presence of TSV by real-time RT-PCR.

All tanks were outfitted with an acclimated biological filter and aeration, and were covered with plastic to contain aerosols. The average salinity of the water was 23 ppt and the water temperature was 28° C. The challenge study was terminated after 15 days with live animals counted as survivors.

RESULTS

Comparison of Virulence: Mortality in Shrimp

First mortality was seen on day 2 after exposure to TSV in all 4 isolates. For the Belize isolate, most (83%) of shrimp died by day 4 and had a 0% survival rate at day 11. For the Thailand isolate, 63% mortalities occurred by day 4 and had a 20% survival rate at the end of 15-day bioassay. For the Hawaii isolate, mortalities increased starting at day 2 and reached a peak at day 5; the final cumulative survival was 22%. For the Venezuela isolate, mortalities occurred slowly at days 2 and 3 with 22% mortality on day 4 followed by a decline in mortality, 42% of shrimp survived through to termination of the study. See FIG. 5 and Table 6. The time period for reaching 50% mortality caused by TSV infection for the isolate of Belize, Thailand, Hawaii and Venezuela were 2.8, 3.5, 4.5 and 7 days, respectively (Table 3).

TABLE 3

Results from per os TSV challenge in SPF *Litopenaeus vannamei* (Kona stock)

| TSV isolate | GenBank No. (ORF1) | Survival (%) (Mean) | Day of 50% mortality |
|---|---|---|---|
| Belize | AAT81157 | 0 | 2.8 |
| Thailand | AAY56363 | 20 | 3.5 |
| US-Hawaii | AAK72220 | 22 | 4.5 |
| Venezuela | ABB17263 | 42 | 7.0* |

*High variation was observed in Venezuela's triplicate tanks, thus the Day of 50% mortality was determined by Kaplan-Meier survival analysis with the Statistix 8 program.

Pathology

Histological analysis of the samples of *L. vannamei* juveniles is summarized in Table 4.

TABLE 4

Summary of histological findings

| UAZ ID# | TSV Isolate | Days after exposure | TSV lesions[1] | LOS[2] |
|---|---|---|---|---|
| O6-407J/1 | Belize | 3 | G4 | G4 |
| 06-407F/1 | Thailand | 3 | G4 | G2 |
| 06-407D/1 | Thailand | 4 | G4 | G3 |
| 06-407E/1 | Thailand | 4 | G3 | G2 |
| 06-407A/1 | Hawaii | 4 | G2 | G3 |
| 06-407C/1 | Hawaii | 4 | G2 | G4 |
| 06-407H/1 | Venezuela | 4 | G4 | G2 |

Severity grade: G1: sign of infection; G2: moderate signs of infection; G3: moderate to high signs of infection; G4: severe infection.
[1]TSV lesions = Presence of TSV pathognomonic lesions in the gills, mouth, stomach, intecumental cuticular epithelium, and appendages.
[2]LOS = presence of lymphoid organ spheroids within the lymphoid organ.

Belize TSV.

Acute lesions of diagnostic TSV infection were found in one representative shrimp sample at a severity grade of G4. Nuclear pyknosis and karyorrhexis were observed in the cuticular epithelium of the general body surface, appendages, gills, stomach and esophagus. Lymphoid organ spheroids were also found at severity grade G4.

Thailand TSV.

Severe (G4) TSV infection was detected in 2 out of 3 shrimp, another shrimp showed a moderate to high grade (G3) of infection. Lymphoid organ spheroids were found at severities of G2 and G3.

Hawaii TSV.

Moderate level (G2) of TSV infection was detected in 2 shrimp collected at day 4. Lymphoid organ spheroids were found at severities of G3 and G4.

Venezuela TSV.

Severe (G4) TSV infection was detected in one representative shrimp sampled at day 4. Lymphoid organ spheroids were found at severity of G2.

Real-Time TSV RT-PCR

All 24 samples (6 from each isolates) were all positive for TSV infection. This confirms that the mortalities observed from bioassays are from TSV infection.

TABLE 5

Mean and range of TSV RNA in gills from shrimp challenge with TSV

| TSV isolate | Mean (Range) TSV copies/:1 RNA |
|---|---|
| Belize | $2.7 \times 10^6$ ($4.8 \times 10^5$-$4.4 \times 10^6$) |
| Thailand | $2.7 \times 10^6$ ($4.3 \times 10^5$-$7.5 \times 10^6$) |
| Hawaii | $5.2 \times 10^7$ ($2.3 \times 10^7$-$7.5 \times 10^7$) |
| Venezuela | $6.5 \times 10^5$ ($6.5 \times 10^2$-$2.0 \times 10^5$) |

TABLE 6

Percent Mortality and Blind Replikin Concentration
The results of 4 TSV virulence (percent mortality) comparisons with blind Replikin Count are:

| Isolate | Percent Mortality | Blind Replikin Concentration |
|---|---|---|
| Belize | 100 | 3.5 |
| Thailand | 80 | 3.4 |
| Hawaii | 78.3 | 3.3 |
| Venezuela | 58.3 | 3.0 |

The order of virulence: Belize>Thailand>(or =) Hawaii>Venezuela, is in agreement with the Replikin concentration. The differences in the Replikin concentrations appear to be small but they are statistically significant at a level of p<0.001. See FIGS. 3 and 4.

EXAMPLE 2

Increased Host Resistance to Taura Syndrome Virus by Administration of Synthetic Replikins

SUMMARY

A vaccine (T1 vaccine) comprising equal parts by weight KVGSRRYKSH (SEQ ID NO: 1), HFATKCFGEVPKK (SEQ ID NO: 2), KAENEFWDGVKQSH (SEQ ID NO: 3), KGHRKVPCEQK (SEQ ID NO: 4), HRKVPCEQK (SEQ ID NO: 5), KVPCEQKIWLH (SEQ ID NO: 6), KIWLHQN-PGK (SEQ ID NO: 7), HQNPGKTQQDMK (SEQ ID NO: 8), KGNTRVHVK (SEQ ID NO: 9), KEHVEKIVDK (SEQ ID NO: 10), and HVEKIVDKAK (SEQ ID NO: 11) was developed in seven days by identifying eleven Replikin sequences in the genome of taura syndrome virus (Hawaii isolate) and chemically synthesizing the eleven Replikin sequences in sufficient volume for a vaccine trial in shrimp as described below.

The T1 vaccine was tested by oral administration to shrimp (*Penaeus vannamei*) in a laboratory bioassay. One month after vaccination, shrimp were challenged per os with TSV to determine if the vaccine induced protection. The results showed that shrimp fed with the vaccine showed resistance to TSV (P=0.0038<0.05). The vaccinated shrimp had a 59% survival and the non-vaccinated shrimp had a 25% survival. The relative percent survival was 45%. That the mortality of the shrimp was caused by TSV infection was confirmed by positive reactions in real-time RT-PCR detection or by the appearance of characteristic lesions observed in histological analysis.

MATERIALS AND METHODS

Animal and Challenge Design:
*P. vannamei* (120 shrimp, Kona stock, from Oceanic Institute, mean weight: 2.0 g) were stocked into 6 tanks (20 shrimp/tank) and fed vaccine T1 5% of total body weight daily for 4 weeks. At the end of 4 weeks, shrimp were exposed to TSV through feeding at 5% of total body weight for 2 days in the morning; in the afternoon, the shrimp were also fed vaccine-mixed feed. Beginning on day 3, all the shrimp were maintained on a vaccine-mixed feed for additional 2 weeks.

For non-vaccinated group, 60 shrimp (20 shrimp per tank) were fed control diet feed for 4 weeks as the positive control for virus-infected tissues.

Preparation of Vaccine-Mixed Feed:
The lyophilized vaccine T1 (Replikins, LLC, Boston, Mass.) was mixed (on ice) with shrimp production 35 mash (Rangen), 1% sodium alginate, 1% sodium hexametaphosphate (added as a binder), and 50% water. The mixed feed was extruded, freeze-dried and then packed into approximately 42 bags for each tank (for each tank: 28 bags for 4-week vaccination and 14 bags for TSV challenge; 2 g per bag) and stored at −20° C. until used. Shrimp feed for positive control was prepared as above without the addition of T1 vaccine (designated as control diet).

TABLE 7

The set up of tanks. All tanks were outfitted with an acclimated biological filter and aeration, and were covered with plastic to contain aerosols.

| Tank # | Vaccine Treatment | | Virus exposure (90-L tank) |
|---|---|---|---|
| A1, 2, 3 20 shrimp per tank | T1 | feed vaccine-mixed feed for 4 weeks | A1: Hawaii TSV (20 shrimp) A2: Hawaii TSV (20 shrimp) A3: Hawaii TSV (20 shrimp) |
| B1, 2, 3 20 shrimp per tank | T1 | feed vaccine-mixed feed for 4 weeks | B1: Hawaii TSV (20 shrimp) B2: Hawaii TSV (20 shrimp) B3: Hawaii TSV (20 shrimp) |
| C1, 2, 3 20 shrimp per tank | Control diet | feed control diet for 4 weeks | C1: Hawaii TSV (20 shrimp) C2: Hawaii TSV (20 shrimp) C3: Hawaii TSV (20 shrimp) |

Statistical Analysis.
The survival between vaccinated and non-vaccinated (positive control) groups were calculated as relative percent survival (RPS: 1-vaccinated group mortality/positive control group mortality)×100 (Amend DF, 1981. Potency testing of fish vaccines. In: Anderson DP, Hennessen W (Eds.) Fish Biologics: Serodiagnostics and vaccines. S. Karger, Basel. Pp. 447-454).

RESULTS

By one-way ANOVA, comparison of the survival at day 15, the percent survival was 51% for the vaccinated groups (6 tanks: combining A1-3 and B1-3), higher than the non-vaccinated group (3 tanks: C1-3), 25%. But the difference is not statistically significant (P=0.1010>0.05). However, tank B-3 in the vaccinated group was an outlier (10% survival). In this tank, severe mortalities occurred early, and the final value for this tank was so far from the others, it was thus was eliminated from the analysis.

Figure 1A:
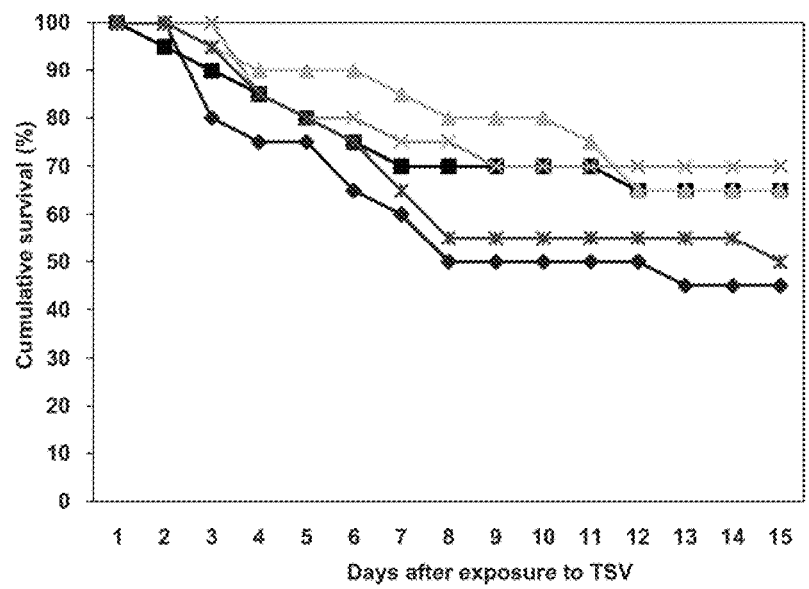
FIG. 1A illustrates shrimp vaccinated with the T1 vaccine containing Replikin sequences from taura syndrome virus (TSV).
Figure 1B:
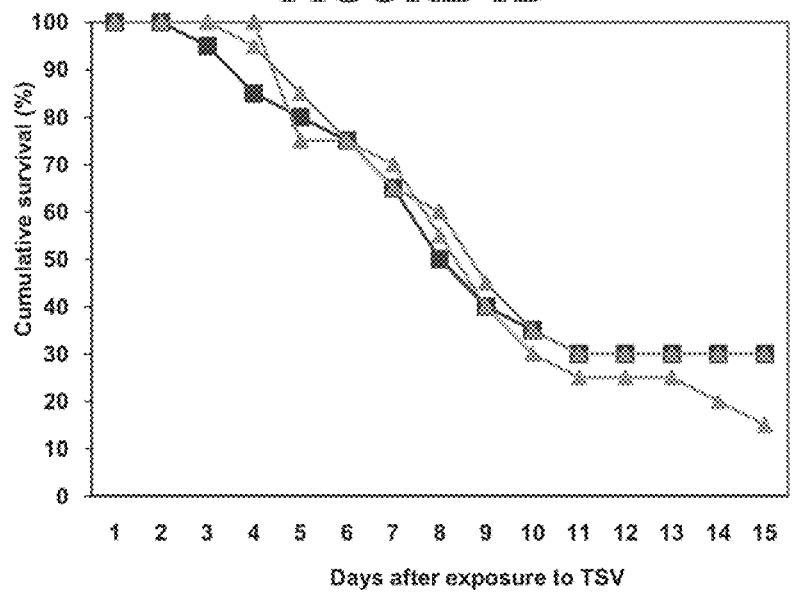
FIG. 1B illustrates non-vaccinated shrimp (a control). The data in FIG. 1 reflect the trials set forth in Example 2 below.

From the 5 vaccinated groups (A1-3 and B1, 2), the first mortality was seen on day 2 after exposure to TSV (FIG. 1A). For the non-vaccinated group, the first mortality occurred on day 3, and 50% of the shrimp died by day 8.5 (FIG. 1B). The vaccinated groups had significant (5% level) resistance to Hawaii TSV infection. The probability is 0.0038 by one-way ANOVA test analysis. The vaccinated groups had a cumulative survival of 59%, higher than the 25% for non-vaccinated group, indicating that vaccination with T1 provided protection from TSV infection. The relative percent survival (RPS) against TSV after vaccination was 45%.

TABLE 8

Percent survival from TSV challenge in vaccinated *Penaeus vannamei*.

| Tank no. | Feed | Survival (%) at day 15 | Day of first mortality |
|---|---|---|---|
| A-1 | Vaccine-mixed | 45 | 3 |
| A-2 | Vaccine-mixed | 65 | 2 |
| A-3 | Vaccine-mixed | 65 | 3 |
| B-1 | Vaccine-mixed | 70 | 4 |
| B-2 | Vaccine-mixed | 50 | 3 |
| B-3 | Vaccine-mixed | 10 | 3 |
| C-1 | control diet | 30 | 3 |
| C-2 | control diet | 30 | 5 |
| C-3 | control diet | 15 | 5 |

Because little is known about the details of the immune system of the shrimp (shrimp appear not to produce antibodies) and other invertebrates, the phenomenon of "resistance" to infection appears to be based in a "primitive immune system" perhaps similar to the "toll receptor" and related systems. Thus the term "increased resistance" is used for the observed phenomenon and Replikin feed is at times used rather than "vaccine" for the administered substance that increases resistance. Nevertheless, vaccine includes the compound administered to shrimp in the trials disclosed in the Examples provided herein.

EXAMPLE 3

Increased Host Resistance to Taura Syndrome Virus by Cycled Challenges with Virus in Combination with Administration of Synthetic Replikins

SUMMARY

Pacific white shrimp (*Penaeus vannamei*) that survived from TSV infection were found to be more tolerant to a second TSV infection. Three groups of TSV chronically-infected shrimp were either fed (1) T1 vaccine containing equal parts by weight KVGSRRYKSH (SEQ ID NO: 1), HFATKCFGEVPKK (SEQ ID NO: 2), KAENEF-WDGVKQSH (SEQ ID NO: 3), KGHRKVPCEQK (SEQ ID NO: 4), HRKVPCEQK (SEQ ID NO: 5), KVPCEQKIWLH (SEQ ID NO: 6), KIWLHQNPGK (SEQ ID NO: 7), HQN-PGKTQQDMK (SEQ ID NO: 8), KGNTRVHVK (SEQ ID NO: 9), KEHVEKIVDK (SEQ ID NO: 10), and HVEKIVD-KAK (SEQ ID NO: 11) (Replikin sequences from Taura syndrome virus-Hawaii isolate), (2) inhibited vaccine T2 containing equal parts by weight KVGSRRYKSHKKKKKHK (SEQ ID NO: 88), HFATKCFGEVPKKKKKKKHK (SEQ ID NO: 89), KAENEFWDGVKQSHKKKKKHK (SEQ ID NO: 90), KGHRKVPCEQKKKKKKHK (SEQ ID NO: 91), HRKVPCEQKKKKKKHK (SEQ ID NO: 92), KVPCEQKI-WLHKKKKKHK (SEQ ID NO: 93), KIWLHQN-PGKKKKKKHK (SEQ ID NO: 94), HQNPGKTQQD-MKKKKKKHK (SEQ ID NO: 95), KGNTRVHVKKKKKKHK (SEQ ID NO: 96), KEH-VEKIVDKKKKKKHK (SEQ ID NO: 97), and HVEKIVD-KAKKKKKKHK (SEQ ID NO: 98) (the same Replikin sequences as T1 except that a seven-residue amino acid tail of KKKKKHK (SEQ ID NO: 204) was added to the C-terminus of each of the eleven Replikin sequences to investigate the effect the exact Replikin structure might have on a resistance effect, or (3) control diet (35% Rangen) for 2 weeks followed by feeding with TSV (Hawaii isolate)-infected tissues for 2 days. A fourth group of shrimp that had not been exposed to TSV infection was also fed a control diet. By day 15 after exposure to TSV, 91% of the vaccinated (T1) shrimp survived. Real-time TSV RT-PCR also showed that the T1-vaccinated shrimp had the lowest viral load of the four groups of shrimp in the trial. For shrimp fed inhibited vaccine (T2), 60% survived, and the shrimp had a slightly higher viral load. For the shrimp fed control diet, there was a 75% survival, and the shrimp contained 10 times higher viral load. The shrimp that had not been previously exposed to TSV (SPF *p. vannamei*) had only 25% survival after exposure to TSV. The trial set up is described in Table 9 below.

TABLE 9

The setup of tanks.

| Tank no. | Number of shrimp | Vaccine | Virus challenged |
|---|---|---|---|
| A | 11 surviving shrimp[1] | T1 | Hawaii TSV |
| B | 10 surviving shrimp[2] | T2 | Hawaii TSV |
| C | 12 surviving shrimp[3] | not vaccinated | Hawaii TSV |
| D | 20 SPF shrimp | not vaccinated | Hawaii TSV |

[1]chronic TSV infection, shrimp were fed T1 and challenged with TSV.
[2]chronic TSV infection, shrimp were fed T2 and challenged with TSV.
[3]chronic TSV infection, shrimp were fed control diet and challenged with TSV.

MATERIALS AND METHODS

Preparation of Vaccine-Mixed Feed:

Each lyophilized vaccine (T1 and T2, provided by Replikins, LLC, Boston, Mass.) was mixed (on ice) with shrimp production 35 mash (Rangen), 1% sodium alginate, 1% sodium hexametaphosphate (added as a binder), and 50% water. The mixed feed was extruded, freeze-dried and then packed into approximately 30 bags (4 g per bag, 120 g of vaccine-mixed feed in total) and stored at −20° C. until used. Shrimp feed for the control group was prepared as above without the addition of vaccine (designated as control diet).

Vaccination Groups:

For each group (vaccine T1 and inhibited vaccine T2), 11 and 10 TSV chronically-infected *P. vannamei* were stocked into each of the 1000-L tanks as described in Table 9 and fed vaccine-mixed feed at 5% of their total body weight, daily, for 2 weeks. The total mass of T1 Replikin sequences administered per gram of total shrimp body weight per day was about 0.50 mg. The shrimp were subsequently fed minced TSV-infected tissues (Hawaii isolate) at 5% of their body weight daily for 2 days in the morning. In the afternoon, the shrimp were also fed vaccine-mixed feed. Beginning on day 3, all the shrimp were maintained on a vaccine-mixed feed for an additional 2 weeks.

Non-Vaccinated Group:

12 shrimp (not vaccinated, previously survived TSV infection) were fed control diet for 2 weeks. The shrimp were subsequently fed minced TSV-infected tissues at 5% of their body weight daily for 2 days. Beginning on day 3, all the shrimp were maintained on the control diet.

Histology.

After exposure to Hawaii TSV, all tanks were checked twice a day for dead or moribund shrimp. All mortalities were removed from the tank and frozen at −70° C. One moribund shrimp from tank C was preserved in Davidson's AFA fixative and processed for routine histology to evaluate the severity of TSV infection.

Real-Time TSV RT-PCR.

For each group, the surviving shrimp were sampled at day 15. Total RNA was extracted from the pleopods and gills with a High Pure RNA tissue kit (Roche). The extracted RNA was analyzed for the presence of TSV by a real-time RT-PCR described by Tang et al (*J. Virol. Method* 115: 109-114, 2004).

RESULTS

Cumulative survival of *Penaeus vannamei* after re-challenge with TSV for shrimp vaccinated with T1, shrimp fed with inhibited T2 vaccine, chronically infected TSV shrimp fed with control diet, and for shrimp not previously exposed to TSV and fed with control diet is set forth in FIG. 2. For T1-vaccinated shrimp, there were no mortalities until day 13. This group had a 91% of survival at day 15 after exposure to TSV (Table 10). For shrimp those fed inhibited-vaccine T2, the first mortality was observed at day 2. The group had a survival rate of 60%. For the non-vaccinated group, the first mortality occurred on day 10, and the group had a survival rate of 75%. The percent survival for SPF shrimp after fed Hawaii TSV was 25%.

TABLE 10

Percent survival from TSV challenge.

| Tank no. | Shrimp | Feed | Survival (%) | Day of first mortality |
|---|---|---|---|---|
| A | Chronic | Vaccine (T1)-mixed | 91 | 13 |
| B | Chronic | Inactive vaccine (T2)-mixed | 60 | 2 |
| C | Chronic | control diet | 75 | 10 |
| D | SPF | control diet | 25 | 3 |

Pathology

Histological analysis of the sample of *P. vannamei* after challenge with TSV is summarized in Table 11.

TABLE 11

Histological findings for TSV infection

| UAZ ID# | Treatment | Days after exposure | TSV lesions |
|---|---|---|---|
| 07-280C (tank C) | non-vaccinated | 10 | LOS@G3 chronic stage of TSV infection |

LOS: lymphoid organ spheroids

Moderate to high (G3) level of lymphoid organ spheroids were found in the non-vaccinated group collected at day 10, indicating chronic TSV infection.

Real-Time TSV RT-PCR

The real-time TSV RT-PCR assay was used to quantify the viral load in the surviving shrimp (Table 12). The results showed that the viral load was lowest in the shrimp vaccinated with T1, $2.46 \times 10^3$ copies/µl RNA. The T2-inhibited vaccine fed shrimp contained higher viral loads, $8.88 \times 10^3$ copies/µl RNA. For the non-vaccinated group, the shrimp had the highest viral loads, $5.20 \times 10^4$ copies/µl RNA.

These results showed that TSV chronically-infected shrimp had higher percent survivals (60-91%) when re-challenged with TSV. In particular, T1-vaccinated *P. vannamei* had the highest survival and lowest viral load. The percent survival for SPF *P. vannamei* challenged with Hawaii TSV was 25%.

EXAMPLE 4

Determination of Replikin Concentration in Publicly Available Accession Numbers for Isolates of TSV from 2000 through 2005

Mean Replikin concentrations were determined for all amino acid sequences for taura syndrome virus with accession numbers publicly available at www.pubmed.com. The amino acid sequences were scanned for Replikin sequences of 7 to 50 amino acids comprising (1) at least one lysine residue located at a first terminus of the sequence and at least one lysine residue or at least one histidine residue located at a second terminus of the sequence; (2) a first lysine residue located six to ten residues from a second lysine residue; (3) at least one histidine residue; and (4) at least 6% lysine residues. The total number of Replikin sequences was determined for each available accession number. The total number of Replikin sequences in each accession number was then divided by the total number of amino acid residues disclosed in the accession number. The result was the Replikin concentration. The mean Replikin concentration was then determined for all viruses isolated and reported in a particular year. Table 13 provides the results.

TABLE 13

TSV Replikin Concentration by Year

| Year | PubMed Accession Number-Replikin Count | No. of Isolates per year | Mean Replikin Concentration per year | S.D. | Significance |
|---|---|---|---|---|---|
| 2000 | NP_149058 70 NP_149057 70 AAK72221 70 AAK72220 70 AAG44834 4 | 5 | 2.7 | 1.3 | low p < 0.02 |
| 2001 | AAM73766 7 | 1 | 0.7 | 0.0 | prev p < 0.02 |
| 2002 | AAN77089 2 AAN77088 2 AAN77087 2 AAN77086 2 AAW32934 2 AAW32932 2 AAW32930 2 AAW32929 1 | 8 | 0.7 | 0.4 | low p > 0.50 |
| 2003 | AAR11292 6 AAR11291 6 AAR11290 6 | 3 | 0.6 | 0.0 | prev p < 0.20 |
| 2004 | AAX07125 2 AAX07117 2 AAT81157 75 AAT81158 75 AAX07127 2 AAX07126 2 AAX07124 2 AAX07123 2 AAX07122 2 AAX07121 2 AAX07120 2 AAX07119 2 AAX07118 2 AAX07116 2 AAX07115 2 AAX07114 2 AAX07113 2 AAX07112 2 AAX35819 2 AAX35818 1 AAX35817 2 AAX35816 1 AAX35815 2 | 23 | 0.8 | 0.9 | low p < 0.40, prev p < 0.20 |
| 2005 | AAY56364 71 AAY56363 71 AAY44822 1 AAY44821 1 AAY44820 1 AAY44819 1 AAY44818 1 AAY44817 1 AAY89097 83 AAY89096 83 ABB17263 63 ABB17264 63 | 12 | 1.8 | 1.7 | low p < 0.02, prev p < 0.05 |

TABLE 12

Mean TSV copies per 1 RNA in TSV surviving shrimp

| Tank no. | Feed | Mean ± S.D. TSV copies/µl |
|---|---|---|
| A | Vaccine (T1)-mixed | $2.46 \times 10^3 \pm 2.22 \times 10^3$ |
| B | Inactive vaccine (T2)-mixed | $8.88 \times 10^3 \pm 8.88 \times 10^3$ |
| C | Control diet | $5.20 \times 10^4 \pm 9.01 \times 10^4$ |

EXAMPLE 5

Determination of Replikin Concentrations in 2001 and 2005 Isolates of TSV Publicly Available at Accession Nos. AAM73766 and AAY89096

The taura syndrome virus (TSV) is generally a less virulent virus than white spot syndrome virus (WSSV) and the structure of the TSV Replikin Scaffold is less closely related to influenza virus than are the structures of WSSV Replikin Scaffolds. See Replikin Scaffold Sequences below. In year 2000, TSV had a Replikin concentration of 2.7. Between 2001 and 2004, TSV had a lower mean Replikin concentration, as low as 0.6, and its Replikin Scaffold disappeared. In 2005 the Replikin Scaffold reappeared along with an increase in lysines and histidines and a commensurate increase in Replikin concentration (1.8) followed by an increase in TSV outbreaks in 2006-2007. See FIG. 6 and Replikin Scaffolds below.

Below is a comparison of the Replikin Scaffold identified in Accession no. AAK72220 in an isolate of TSV from 2000 and the Replikin Scaffold identified in Accession no. AAY89096 in an isolate of TSV from 2005. The TSV Replikin Scaffolds are also compared to two Replikin Scaffold sequences in H1N1 influenza virus in the 1918 pandemic and shrimp WSSV in 2000.

Replikin Scaffold Sequences (SEQ ID NOS 99-104, Respectively, in Order of Appearance)

| | | |
|---|---|---|
| kkgssypklsksyvnnkgkevlvlwgyhh | 1918 | H1N1 Human Influenza Pandemic |
| -kgssypklsksyvnnkgkevlvlwgvhh | 1918 | H1N1 Human Influenza Pandemic |
| -kvhldvkgvkqllhlkvrldvrgakqlh | 2000 | Shrimp White Spot Syndrome Virus |
| kknvksakqlphlkvlkkldvrgakqlph | 2000 | Shrimp White Spot Syndrome Virus |
| kkvqanktrvfaasnqglalalrryylsfldh | 2000 | Taura Syndrome Virus AAK72220 |
| kkacrnagykeaclheldcksfllaqqgragah | 2005 | Taura Syndrome Virus AAY89096 |

The following analysis of Accession Nos. AAM73766 and AAY89096 demonstrate Replikin concentration analysis of amino acid sequences of isolates of taura syndrome virus having publicly available accession numbers at www.pubmed.com.

```
PubMed Code: AAM73766
Isolated: 2001
Source: Taura Syndrome Virus
```
(SEQ ID NO: 105)

$M^1P^2A^3N^4P^5V^6E^7I^8D^9N^{10}F^{11}D^{12}T^{13}T^{14}T^{15}S^{16}G^{17}G^{18}L^{19}I^{20}P^{21}G^{22}G^{23}S^{24}V^{25}T^{26}N^{27}S^{28}E^{29}G^{30}S^{31}T^{32}I^{33}L^{34}M^{35}N^{36}D^{37}$ $I^{38}P^{39}I^{40}T^{41}N^{42}Q^{43}N^{44}V^{45}V^{46}L^{47}S^{48}K^{49}N^{50}V^{51}T^{52}D^{53}N^{54}L^{55}F^{56}E^{57}V^{58}Q^{59}D^{60}Q^{61}A^{62}L^{63}I^{64}E^{65}S^{66}L^{67}S^{68}R^{69}D^{70}V^{71}$ $L^{72}L^{73}H^{74}N^{75}D^{76}S^{77}W^{78}T^{79}S^{80}S^{81}D^{82}D^{83}E^{84}I^{85}G^{86}T^{87}T^{88}M^{89}T^{90}Q^{91}E^{92}Q^{93}L^{94}A^{95}T^{96}E^{97}F^{98}N^{99}Q^{100}P^{101}H^{102}L^{103}$ $Y^{104}E^{105}I^{106}S^{107}L^{108}P^{109}D^{110}I^{111}I^{112}V^{113}R^{114}K^{115}S^{116}L^{117}F^{118}M^{119}S^{120}N^{121}K^{122}L^{123}A^{124}N^{125}I^{126}A^{127}Y^{128}$ $M^{129}R^{130}C^{131}D^{132}$ $Y^{133}E^{134}V^{135}T^{136}V^{137}R^{138}V^{139}Q^{140}A^{141}T^{142}P^{143}F^{144}L^{145}Q^{146}G^{147}A^{148}L^{149}W^{150}L^{151}W^{152}L^{153}K^{154}M^{155}N^{156}A^{157}$ $K^{158}$ $Q^{159}T^{160}S^{161}I^{162}I^{163}R^{164}R^{165}T^{166}L^{167}T^{168}E^{169}H^{170}L^{171}R^{172}S^{173}I^{174}T^{175}S^{176}F^{177}P^{178}G^{179}I^{180}E^{181}M^{182}N^{183}$ $L^{184}Q^{185}S^{186}$ $E^{187}A^{188}R^{189}A^{190}I^{191}T^{192}L^{193}S^{194}I^{195}P^{196}Y^{197}T^{198}S^{199}E^{200}F^{201}Q^{202}V^{203}F^{204}N^{205}P^{206}R^{207}N^{208}V^{209}N^{210}N^{211}$ $L^{212}N^{213}S^{214}$ $I^{215}R^{216}L^{217}S^{218}V^{219}L^{220}S^{221}Q^{222}L^{223}Q^{224}G^{225}P^{226}E^{227}D^{228}V^{229}E^{230}S^{231}A^{232}S^{233}Y^{234}S^{235}I^{236}G^{237}G^{238}R^{239}$ $L^{240}K^{241}N^{242}I^{243}K^{244}L^{245}Y^{246}G^{247}H^{248}A^{249}P^{250}S^{251}V^{252}T^{253}S^{254}S^{255}V^{256}Y^{257}P^{258}S^{259}T^{260}Q^{261}S^{262}G^{263}Y^{264}$ $D^{265}D^{266}D^{267}C^{268}P^{269}I^{270}V^{271}H^{272}A^{273}G^{274}T^{275}D^{276}E^{277}D^{278}S^{279}S^{280}K^{281}Q^{282}G^{283}I^{284}V^{285}S^{286}R^{287}V^{288}A^{289}$ $D^{290}T^{291}V^{292}G^{293}A^{294}V^{295}A^{296}N^{297}V^{298}V^{299}D^{300}G^{301}V^{302}G^{303}V^{304}P^{305}I^{306}L^{307}S^{308}T^{309}I^{310}A^{311}K^{312}P^{313}V^{314}$ $S^{315}W^{316}V^{317}S^{318}G^{319}V^{320}V^{321}S^{322}N^{323}V^{324}$ $A^{325}S^{326}M^{327}F^{328}G^{329}F^{330}S^{331}K^{332}D^{333}R^{334}D^{335}M^{336}T^{337}K^{338}V^{339}N^{340}A^{341}Y^{342}E^{343}N^{344}L^{345}P^{346}G^{347}K^{348}G^{349}$ $F^{350}T^{351}H^{352}G^{353}V^{354}G^{355}F^{356}D^{357}Y^{358}G^{359}V^{360}P^{361}L^{362}S^{363}L^{364}F^{365}P^{366}N^{367}N^{368}A^{369}I^{370}D^{371}P^{372}T^{373}I^{374}$ $A^{375}V^{376}P^{377}E^{378}G^{379}L^{380}D^{381}I^{382}M^{383}S^{384}I^{385}E^{386}Y^{387}L^{388}A^{389}Q^{390}R^{391}P^{392}Y^{393}M^{394}L^{395}N^{396}R^{397}Y^{398}T^{399}$ $I^{400}R^{401}G^{402}G^{403}D^{404}T^{405}P^{406}$ $D^{407}V^{408}H^{409}G^{410}T^{411}T^{412}V^{413}A^{414}D^{415}I^{416}P^{417}V^{418}S^{419}P^{420}V^{421}N^{422}F^{423}S^{424}L^{425}Y^{426}G^{427}K^{428}V^{429}I^{430}A^{431}$ $K^{432}Y^{433}$ $R^{434}T^{435}L^{436}F^{437}A^{438}A^{439}P^{440}V^{441}S^{442}L^{443}A^{444}V^{445}A^{446}M^{447}A^{448}N^{449}W^{450}W^{451}R^{452}G^{453}N^{454}I^{455}N^{456}L^{457}N^{458}$ $L^{459}R^{460}F^{461}A^{462}K^{463}T^{464}Q^{465}Y^{466}H^{467}Q^{468}C^{469}R^{470}L^{471}L^{472}V^{473}Q^{474}Y^{475}L^{476}P^{477}Y^{478}G^{479}S^{480}G^{481}V^{482}Q^{483}$ $P^{484}I^{485}E^{486}S^{487}$

-continued $I^{488}L^{489}S^{490}Q^{491}I^{492}I^{493}D^{494}I^{495}S^{496}Q^{497}V^{498}D^{499}P^{500}K^{501}G^{502}I^{503}D^{504}I^{505}A^{506}F^{507}P^{508}S^{509}V^{510}Y^{511}P^{512}$
$N^{513}K^{514}W^{515}M^{516}R^{517}V^{518}Y^{519}D^{520}P^{521}A^{522}K^{523}V^{524}G^{525}Y^{526}T^{527}A^{528}D^{529}C^{530}A^{531}P^{532}G^{533}R^{534}I^{535}S^{536}I^{537}$
$S^{538}V^{539}L^{540}N^{541}P^{542}$ $L^{543}I^{544}S^{545}A^{546}S^{547}T^{548}V^{549}S^{550}P^{551}N^{552}I^{553}V^{554}M^{555}Y^{556}P^{557}W^{558}S^{559}H^{560}N^{561}S^{562}N^{563}L^{564}E^{565}V^{566}A^{567}$
$E^{568}P^{569}$ $G^{570}T^{571}L^{572}A^{573}K^{574}A^{575}A^{576}I^{577}G^{578}F^{579}N^{580}Y^{581}P^{582}A^{583}D^{584}V^{585}P^{586}E^{587}E^{588}P^{589}T^{590}F^{591}S^{592}V^{593}T^{594}$
$R^{595}A^{596}$ $P^{597}V^{598}S^{599}G^{600}T^{601}L^{602}F^{603}T^{604}L^{605}L^{606}Q^{607}D^{608}T^{609}K^{610}V^{611}S^{612}L^{613}G^{614}E^{615}A^{616}D^{617}G^{618}V^{619}F^{620}S^{621}$
$L^{622}Y^{623}$ $F^{624}T^{625}N^{626}T^{627}T^{628}T^{629}G^{630}R^{631}R^{632}H^{633}R^{634}L^{635}T^{636}Y^{637}A^{638}G^{639}L^{640}P^{641}G^{642}E^{643}L^{644}G^{645}S^{646}C^{647}E^{648}$
$I^{649}V^{650}$ $K^{651}P^{652}L^{653}Q^{654}G^{655}Q^{656}Y^{657}S^{658}I^{659}E^{660}Y^{661}A^{662}A^{663}T^{664}S^{665}A^{666}P^{667}T^{668}L^{669}V^{670}L^{671}D^{672}R^{673}P^{674}I^{675}$
$F^{676}S^{677}E^{678}P^{679}I^{680}G^{681}P^{682}K^{683}Y^{684}V^{685}V^{686}T^{687}K^{688}V^{689}K^{690}N^{691}G^{692}D^{693}V^{694}Y^{695}S^{696}I^{697}S^{698}E^{699}E^{700}$
$T^{701}L^{702}V^{703}T^{704}C^{705}$ $G^{706}S^{707}M^{708}A^{709}A^{710}L^{711}G^{712}T^{713}A^{714}T^{715}V^{716}A^{717}L^{718}Q^{719}S^{720}V^{721}D^{722}E^{723}T^{724}I^{725}E^{726}I^{727}L^{728}K^{729}L^{730}$
$E^{731}S^{732}$ $D^{733}F^{734}E^{735}S^{736}K^{737}A^{738}P^{739}V^{740}K^{741}F^{742}T^{743}P^{744}G^{745}N^{746}Y^{747}T^{748}V^{749}V^{750}T^{751}E^{752}A^{753}S^{754}D^{755}V^{756}E^{757}$
$L^{758}V^{759}$ $T^{760}N^{761}Q^{762}D^{763}I^{764}T^{765}V^{766}N^{767}E^{768}H^{769}N^{770}P^{771}R^{772}T^{773}H^{774}A^{775}G^{776}I^{777}D^{778}E^{779}P^{780}P^{781}P^{782}V^{783}K^{784}$
$R^{785}S^{786}$ $V^{787}I^{788}G^{789}R^{790}I^{791}V^{792}R^{793}V^{794}V^{795}A^{796}R^{797}Y^{798}P^{799}P^{800}N^{801}K^{802}L^{803}I^{804}R^{805}R^{806}I^{807}L^{808}R^{809}D^{810}L^{811}$
$S^{812}Q^{813}S^{814}P^{815}C^{816}I^{817}Y^{818}P^{819}S^{820}T^{821}H^{822}A^{823}G^{824}L^{825}D^{826}Y^{827}S^{828}S^{829}S^{830}D^{831}T^{832}S^{833}T^{834}M^{835}L^{836}$
$T^{837}T^{838}M^{839}G^{840}E^{841}Q^{842}F^{843}V^{844}S^{845}L^{846}R^{847}M^{848}L^{849}T^{850}R^{851}R^{852}S^{853}S^{854}P^{855}Y^{856}D^{857}I^{858}L^{859}R^{860}G^{861}$
$D^{862}L^{863}V^{864}T^{865}L^{866}P^{867}G^{868}S^{870}F^{871}G^{872}T^{873}D^{874}N^{875}S^{876}L^{877}R^{878}Q^{879}S^{880}L^{881}V^{882}N^{883}I^{884}I^{885}S^{886}Y^{887}$
$M^{888}Y^{889}R^{890}F^{891}T^{892}H^{893}G^{894}S^{895}I^{896}S^{897}Y^{898}K^{899}I^{900}I^{901}P^{902}K^{903}N^{904}K^{905}G^{906}D^{907}L^{908}Y^{909}I^{910}T^{911}T^{912}$
$T^{913}S^{914}P^{915}D^{916}S^{917}I^{918}E^{919}T^{920}S^{921}T^{922}S^{923}A^{924}Y^{925}Q^{926}$ $F^{927}D^{928}T^{929}N^{930}R^{931}A^{932}M^{933}H^{934}Y^{935}I^{936}N^{937}T^{938}S^{939}L^{940}N^{941}P^{942}M^{943}A^{944}Q^{945}I^{946}S^{947}L^{948}P^{949}Y^{950}Y^{951}$
$S^{952}P^{953}$ $A^{954}E^{955}N^{956}L^{957}V^{958}I^{959}D^{960}S^{961}K^{962}S^{963}F^{964}P^{965}Q^{966}L^{967}S^{968}D^{969}L^{970}S^{971}I^{972}S^{973}N^{974}L^{975}E^{976}R^{977}T^{978}$
$E^{979}N^{980}E^{981}Y^{982}F^{983}V^{984}L^{985}A^{986}S^{987}A^{988}G^{989}D^{990}P^{991}M^{992}T^{993}F^{994}S^{995}Q^{996}L^{997}A^{998}G^{999}C^{1000}P^{1001}A^{1002}$
$F^{1003}T^{1004}F^{1005}G^{1006}P^{1007}A^{1008}E^{1009}L^{1010}A^{1011}$ Replikin Sequences in Amino-Terminal Portion of Peptide (1) $H^{102}L^{103}Y^{104}E^{105}I^{106}S^{107}L^{108}P^{109}D^{110}D^{111}I^{112}V^{113}R^{114}K^{115}S^{116}L^{117}F^{118}M^{119}S^{120}N^{121}K^{122}$ (SEQ ID NO: 106

-continued

Replikin Sequences in Mid-Molecule Portion of Peptide
Zero Replikins.
Replikin Sequences in Carboxy-Terminal Portion of Peptide (4) $K^{729}L^{730}E^{731}S^{732}D^{733}F^{734}E^{735}S^{736}K^{737}A^{738}P^{739}V^{740}K^{741}F^{742}T^{743}P^{744}G^{745}N^{746}Y^{747}T^{748}V^{749}V^{750}T^{751}E^{752}$ $A^{753}S^{754}D^{755}V^{756}E^{757}L^{758}V^{759}T^{760}N^{761}Q^{762}D^{763}I^{764}T^{765}V^{766}N^{767}E^{768}H^{769}N^{770}P^{771}R^{772}T^{773}H^{774}$ (SEQ ID NO: 109)

(5) $K^{729}L^{730}E^{731}S^{732}D^{733}F^{734}E^{735}S^{736}K^{737}A^{738}P^{739}V^{740}K^{741}F^{742}T^{743}P^{744}G^{745}N^{746}Y^{747}T^{748}V^{749}V^{750}T^{751}E^{752}$ $A^{753}S^{754}D^{755}V^{756}E^{757}L^{758}V^{759}T^{760}N^{761}Q^{762}D^{763}I^{764}T^{765}V^{766}N^{767}E^{768}H^{769}$ (SEQ ID NO: 110)

(6) $H^{893}G^{894}S^{895}I^{896}S^{897}Y^{898}K^{899}I^{900}I^{901}P^{902}K^{903}N^{904}K^{905}$ (SEQ ID NO: 111)

(7) $K^{899}I^{900}I^{901}P^{902}K^{903}N^{904}K^{905}G^{906}P^{907}L^{908}Y^{909}I^{910}T^{911}T^{912}T^{913}S^{914}P^{915}D^{916}S^{917}I^{918}E^{919}T^{920}S^{921}T^{922}$ $S^{923}A^{924}Y^{925}Q^{926}F^{927}D^{928}T^{929}N^{930}R^{931}A^{932}M^{933}H^{934}$ (SEQ ID NO: 112)

Replikin Count = Number of Replikins per 100 amino acids = 7/1011 = 0.7
PubMed Code: AAY89096
Isolated: 2005
Source: Taura Syndrome Virus (SEQ ID NO: 113)

$M^{1}A^{2}S^{3}Y^{4}Y^{5}L^{6}N^{7}I^{8}K^{9}T^{10}H^{11}N^{12}L^{13}R^{14}R^{15}T^{16}P^{17}G^{18}A^{19}H^{20}R^{21}A^{22}F^{23}Y^{24}V^{25}M^{26}N^{27}D^{28}D^{29}G^{30}E^{31}N^{32}R^{33}I^{34}Y^{35}$ $S^{36}L^{37}I^{38}G^{39}T^{40}L^{41}R^{42}R^{43}A^{44}P^{45}A^{46}F^{47}K^{48}V^{49}G^{50}S^{51}R^{52}R^{53}Y^{54}K^{55}S^{56}H^{57}I^{58}P^{59}Y^{60}R^{61}R^{62}K^{63}A^{64}T^{65}V^{66}A^{67}E^{68}$ $L^{69}C^{70}$ $N^{71}Q^{72}L^{73}T^{74}D^{75}R^{76}V^{77}L^{78}P^{79}F^{80}A^{81}N^{82}P^{83}Q^{84}V^{85}W^{86}K^{87}E^{88}V^{89}I^{90}S^{91}E^{92}N^{93}K^{94}V^{95}Q^{96}P^{97}D^{98}S^{99}M^{100}L^{101}K^{102}$ $A^{103}A^{104}F^{105}G^{106}N^{107}W^{108}E^{109}L^{110}W^{111}P^{112}K^{113}D^{114}K^{115}V^{116}C^{117}E^{118}E^{119}L^{120}Y^{121}S^{122}E^{123}C^{124}E^{125}C^{126}G^{127}$ $Y^{128}V^{129}G^{130}T^{131}C^{132}Y^{133}V^{134}S^{135}V^{136}D^{137}W^{138}L^{139}P^{140}F^{141}Q^{142}A^{143}T^{144}K^{145}C^{146}N^{147}D^{148}L^{149}I^{150}L^{151}K^{152}$ $M^{153}N^{154}R^{155}N^{156}V^{157}E^{158}Y^{159}P^{160}Y^{161}H^{162}T^{163}I^{164}G^{165}V^{166}S^{167}G^{168}N^{169}V^{170}V^{171}T^{172}N^{173}T^{174}D^{175}I^{176}V^{177}$ $Y^{178}T^{179}G^{180}Y^{181}A^{182}D^{183}V^{184}$ $F^{185}K^{186}C^{187}E^{188}K^{189}C^{190}D^{191}L^{192}L^{193}M^{194}G^{195}A^{196}W^{197}A^{198}P^{199}N^{200}D^{201}I^{202}P^{203}A^{204}L^{205}T^{206}H^{207}N^{208}I^{209}$ $R^{210}S^{211}$ $S^{212}Q^{213}C^{214}V^{215}Q^{216}F^{217}K^{218}L^{219}P^{220}T^{221}E^{222}N^{223}L^{224}A^{225}A^{226}R^{227}N^{228}Y^{229}V^{230}L^{231}L^{232}C^{233}E^{234}E^{235}I^{236}$ $E^{237}R^{238}$ $E^{239}N^{240}I^{241}P^{242}V^{243}I^{244}F^{245}Q^{246}D^{247}Y^{248}S^{249}E^{250}G^{251}N^{252}V^{253}F^{254}T^{255}C^{256}R^{257}I^{258}V^{259}S^{260}G^{261}D^{262}L^{263}$ $T^{264}A^{265}V^{266}G^{267}T^{268}A^{269}S^{270}N^{271}M^{272}Y^{273}T^{274}A^{275}R^{276}D^{277}V^{278}A^{279}S^{280}K^{281}S^{282}L^{283}L^{284}D^{285}Q^{286}L^{287}H^{288}$ $N^{289}T^{290}P^{291}N^{292}V^{293}H^{294}M^{295}H^{296}S^{297}L^{298}H^{299}S^{300}L^{301}P^{302}Y^{303}E^{304}N^{305}P^{306}P^{307}C^{308}E^{309}A^{310}L^{311}I^{312}F^{313}$ $A^{314}V^{315}E^{316}Q^{317}G^{318}I^{319}I^{320}P^{321}P^{322}V^{323}T^{324}F^{325}D^{326}P^{327}V^{328}F^{329}A^{330}N^{331}D^{332}E^{333}Y^{334}V^{335}I^{336}T^{337}I^{338}$ $S^{339}C^{340}S^{341}L^{342}L^{343}V^{344}V^{345}S^{346}D^{347}V^{348}G^{349}P^{350}T^{351}Q^{352}A^{353}V^{354}A^{355}R^{356}E^{357}R^{358}A^{359}A^{360}K^{361}R^{362}F^{363}$ $L^{364}K^{365}M^{366}Y^{367}D^{368}Y^{369}S^{370}A^{371}S^{372}Y^{373}P^{374}S^{375}T^{376}$ $H^{377}M^{378}F^{379}T^{380}L^{381}S^{382}T^{383}L^{384}P^{385}Q^{386}R^{387}S^{388}G^{389}E^{390}T^{391}L^{392}E^{393}L^{394}A^{395}N^{396}A^{397}T^{398}L^{399}N^{400}N^{401}$ $V^{402}N^{403}$ $N^{404}V^{405}I^{406}D^{407}R^{408}H^{409}D^{410}E^{411}A^{412}I^{413}S^{414}N^{415}V^{416}R^{417}Q^{418}N^{419}V^{420}E^{421}V^{422}K^{423}L^{424}T^{425}D^{426}S^{428}R^{429}$ $Q^{430}$ $V^{431}G^{432}A^{433}M^{434}L^{435}P^{436}K^{437}V^{438}E^{439}T^{440}V^{441}I^{442}D^{443}D^{444}V^{445}S^{446}S^{447}T^{448}L^{449}G^{450}S^{451}F^{452}R^{453}G^{454}V^{455}$ $L^{456}D^{457}$ $K^{458}I^{459}S^{460}A^{461}W^{462}M^{463}P^{464}K^{465}S^{466}N^{467}P^{468}K^{469}I^{470}I^{471}D^{472}L^{473}I^{474}K^{475}E^{476}T^{477}F^{478}V^{479}S^{480}L^{481}F^{482}$ $F^{483}A^{484}I^{485}$ $L^{486}T^{487}K^{488}S^{489}L^{490}Y^{491}P^{492}I^{493}I^{494}Q^{495}G^{496}I^{497}S^{498}S^{499}Y^{500}A^{501}L^{502}R^{503}N^{504}N^{505}L^{506}M^{507}A^{508}N^{509}H^{510}$

-continued $L^{511}T^{512}A^{513}L^{514}S^{515}E^{516}W^{517}L^{518}M^{519}T^{520}L^{521}E^{522}Y^{523}D^{524}S^{525}P^{526}D^{527}E^{528}E^{529}E^{530}M^{531}P^{532}S^{533}T^{534}H^{535}G^{536}F^{537}M^{538}D^{539}D^{540}$ $L^{541}T^{542}S^{543}R^{544}L^{545}P^{546}G^{547}L^{548}N^{549}G^{550}A^{551}K^{552}V^{553}Q^{554}A^{555}A^{556}T^{557}I^{558}Y^{559}E^{560}S^{561}I^{562}G^{563}T^{564}G^{565}L^{566}C^{567}$ $A^{568}A^{569}L^{570}S^{571}G^{572}I^{573}L^{574}S^{575}F^{576}I^{577}A^{578}V^{579}M^{580}C^{581}L^{582}G^{583}I^{584}T^{585}D^{586}L^{587}S^{588}A^{589}V^{590}T^{591}F^{592}N^{593}K^{594}L^{595}L^{596}T^{597}Q^{598}S^{599}S^{600}L^{601}V^{602}G^{603}R^{604}A^{605}L^{606}V^{607}G^{608}V^{609}R^{610}S^{611}F^{612}K^{613}D^{614}V^{615}F^{616}F^{617}G^{618}I^{619}W^{620}D^{621}Y^{622}$ $V^{623}D^{624}N^{625}Q^{626}V^{627}C^{628}E^{629}I^{630}L^{631}Y^{632}G^{633}K^{634}S^{635}R^{636}K^{637}N^{638}L^{639}D^{640}L^{641}L^{642}K^{643}E^{644}Y^{645}P^{646}S^{647}L^{648}D^{649}$ $S^{650}L^{651}L^{652}S^{653}I^{654}F^{655}N^{656}Y^{657}F^{658}H^{659}D^{660}T^{661}V^{662}D^{663}A^{664}N^{665}V^{666}L^{667}I^{668}S^{669}C^{670}N^{671}R^{672}A^{673}A^{674}C^{675}E^{676}L^{677}L^{678}V^{679}K^{680}A^{681}D^{682}N^{683}L^{684}Y^{685}Q^{686}G^{687}Y^{688}L^{689}D^{690}K^{691}S^{692}I^{693}T^{694}L^{695}M^{696}H^{697}R^{698}E^{699}I^{700}S^{701}S^{702}R^{703}L^{704}$ $K^{705}E^{706}A^{707}R^{708}N^{709}S^{710}V^{711}K^{712}D^{713}L^{714}I^{715}A^{716}K^{717}A^{718}Q^{719}V^{720}Y^{721}L^{722}T^{723}C^{724}G^{725}D^{726}G^{727}S^{728}R^{729}V^{730}P^{731}$ $P^{732}V^{733}V^{734}V^{735}Y^{736}M^{737}T^{738}G^{739}D^{740}A^{741}G^{742}C^{743}G^{744}K^{745}T^{746}E^{747}L^{748}S^{749}M^{750}A^{751}L^{752}Q^{753}D^{754}H^{755}F^{756}A^{757}T^{758}K^{759}Y^{760}F^{761}G^{762}F^{763}V^{764}P^{765}K^{766}K^{767}D^{768}V^{769}I^{770}Y^{771}S^{772}R^{773}T^{774}A^{775}E^{776}N^{777}T^{778}F^{779}W^{780}D^{781}G^{782}V^{783}K^{784}Q^{785}S^{786}H^{787}K^{788}I^{789}I^{790}A^{791}Y^{792}D^{793}V^{794}V^{795}L^{796}Q^{797}I^{798}V^{799}D^{800}S^{801}A^{802}Q^{803}K^{804}P^{805}N^{806}P^{807}E^{808}L^{809}F^{810}E^{811}F^{812}I^{813}R^{814}L^{815}N^{816}S^{817}D^{818}I^{819}Q^{820}Y^{821}Q^{822}V^{823}H^{824}M^{825}S^{826}S^{827}V^{828}S^{829}D^{830}K^{831}A^{832}N^{833}T^{834}F^{835}T^{836}A^{837}P^{838}S^{839}F^{840}$ $V^{841}F^{842}A^{843}T^{844}S^{845}N^{846}V^{847}N^{848}P^{849}G^{850}T^{851}Y^{852}V^{853}P^{854}K^{855}S^{856}I^{857}H^{858}S^{859}A^{860}D^{861}A^{862}F^{863}R^{864}R^{865}R^{866}L^{867}$ $D^{868}L^{869}C^{870}V^{871}Y^{872}V^{873}D^{874}V^{875}K^{876}D^{877}E^{878}F^{879}A^{880}R^{881}I^{882}V^{883}A^{884}G^{885}S^{886}K^{887}G^{888}H^{889}R^{890}K^{891}V^{892}P^{893}C^{894}$ $E^{895}Q^{896}K^{897}I^{898}W^{899}L^{900}H^{901}Q^{902}N^{903}P^{904}G^{905}K^{906}T^{907}Q^{908}H^{909}D^{910}M^{911}K^{912}H^{913}E^{914}I^{915}V^{916}A^{917}G^{918}T^{919}Y^{920}K^{921}$ $I^{922}T^{923}P^{924}E^{925}T^{926}A^{927}V^{928}Y^{929}E^{930}L^{931}H^{932}V^{933}D^{934}T^{935}T^{936}L^{937}G^{939}D^{940}A^{941}Q^{942}S^{943}K^{944}V^{945}C^{946}A^{947}Y^{948}$ $D^{949}G^{950}L^{951}V^{952}S^{953}L^{954}I^{955}E^{956}Q^{957}V^{958}R^{959}R^{960}L^{961}R^{962}V^{963}A^{964}A^{965}H^{966}S^{967}D^{968}K^{969}V^{970}E^{971}T^{972}D^{973}V^{974}P^{975}$ $V^{976}L^{977}P^{978}T^{979}R^{980}L^{981}H^{982}E^{983}L^{984}S^{985}Q^{986}E^{987}T^{988}F^{989}P^{990}N^{991}T^{992}H^{993}A^{994}G^{995}V^{996}G^{997}F^{998}Q^{999}F^{1000}A^{1001}T^{1002}D^{1003}W^{1004}L^{1005}G^{1006}D^{1007}F^{1008}D^{1009}R^{1010}P^{1011}V^{1012}E^{1013}A^{1014}L^{1015}S^{1016}Y^{1017}L^{1018}N^{1019}K^{1020}T^{1021}L^{1022}E^{1023}A^{1024}$ $H^{1025}F^{1026}V^{1027}S^{1028}R^{1029}S^{1030}A^{1031}N^{1032}D^{1033}G^{1034}S^{1035}M^{1036}F^{1037}I^{1038}P^{1039}A^{1040}I^{1041}E^{1042}V^{1043}A^{1044}D^{1045}L^{1046}L^{1047}C^{1048}Q^{1049}R^{1050}H^{1051}N^{1052}N^{1053}T^{1054}N^{1055}L^{1056}N^{1057}E^{1058}E^{1059}L^{1060}V^{1061}Y^{1062}L^{1063}T^{1064}W^{1065}M^{1066}T^{1067}Q^{1068}I^{1069}$ $T^{1070}D^{1071}K^{1072}E^{1073}L^{1074}A^{1075}S^{1076}L^{1077}L^{1078}V^{1079}Y^{1080}F^{1081}T^{1082}N^{1083}N^{1084}G^{1085}M^{1086}D^{1087}K^{1088}S^{1089}I^{1090}W^{1091}$ $K^{1092}K^{1093}S^{1094}A^{1095}E^{1096}R^{1097}S^{1098}A^{1099}Q^{1100}A^{1101}I^{1102}S^{1103}Q^{1104}C^{1105}K^{1106}N^{1107}A^{1108}W^{1109}T^{1110}R^{1111}I^{1112}N^{1113}D^{1114}F^{1115}L^{1116}K^{1117}N^{1118}H^{1119}W^{1120}I^{1121}S^{1122}I^{1123}S^{1124}A^{1125}V^{1126}I^{1127}G^{1128}S^{1129}A^{1130}L^{1131}L^{1132}I^{1133}G^{1134}G^{1135}V^{1136}S^{1137}$ -continued $S^{1138}A^{1139}V^{1140}K^{1141}C^{1142}A^{1143}T^{1144}K^{1145}C^{1146}R^{1147}V^{1148}R^{1149}G^{1150}I^{1151}L^{1152}Q^{1153}D^{1154}G^{1155}G^{1156}S^{1157}I^{1158}M^{1159}Q^{1160}L^{1161}V^{1162}G^{1163}V^{1164}R^{1165}S^{1166}C^{1167}M^{1168}Y^{1169}A^{1170}C^{1171}Q^{1172}L^{1173}C^{1174}K^{1175}R^{1176}I^{1177}K^{1178}N^{1179}C^{1180}D^{1181}L^{1182}$ $R^{1183}L^{1184}V^{1185}R^{1186}R^{1187}N^{1188}R^{1189}S^{1190}S^{1191}G^{1192}V^{1193}T^{1194}F^{1195}F^{1196}V^{1197}P^{1198}G^{1199}D^{1200}V^{1201}R^{1202}R^{1203}V^{1204}$ $A^{1205}R^{1206}H^{1207}V^{1208}I^{1209}S^{1210}A^{1211}A^{1212}D^{1213}F^{1214}C^{1215}E^{1216}V^{1217}P^{1218}V^{1219}H^{1220}H^{1221}S^{1222}F^{1223}I^{1224}Q^{1225}S^{1226}L^{1227}C^{1228}D^{1229}E^{1230}A^{1231}F^{1232}T^{1233}V^{1234}H^{1235}S^{1236}D^{1237}K^{1238}E^{1239}E^{1240}T^{1241}F^{1242}S^{1243}I^{1244}L^{1245}D^{1246}F^{1247}T^{1248}P^{1249}E^{1250}$ $A^{1251}K^{1252}G^{1253}R^{1254}N^{1255}S^{1256}P^{1257}E^{1258}S^{1259}A^{1260}V^{1261}V^{1262}E^{1263}S^{1264}H^{1265}Q^{1266}D^{1267}Y^{1268}R^{1269}V^{1270}K^{1271}A^{1272}$ $A^{1273}V^{1274}V^{1275}E^{1276}S^{1277}H^{1278}Q^{1279}D^{1280}F^{1281}K^{1282}P^{1283}K^{1284}D^{1285}A^{1286}I^{1287}V^{1288}E^{1289}S^{1290}T^{1291}I^{1292}D^{1293}T^{1294}V^{1295}F^{1296}T^{1297}E^{1298}S^{1299}H^{1300}Q^{1301}D^{1302}V^{1303}R^{1304}V^{1305}K^{1306}I^{1307}H^{1308}I^{1309}Q^{1310}I^{1311}E^{1312}S^{1313}H^{1314}Q^{1315}D^{1316}F^{1317}R^{1318}A^{1319}K^{1320}N^{1321}P^{1322}I^{1323}V^{1324}E^{1325}S^{1326}R^{1327}K^{1328}P^{1329}D^{1330}Y^{1331}Q^{1332}V^{1333}E^{1334}W^{1335}T^{1336}D^{1337}L^{1338}R^{1339}T^{1340}E^{1341}S^{1342}S^{1343}N^{1344}R^{1345}R^{1346}A^{1347}A^{1348}Q^{1349}D^{1350}L^{1351}S^{1352}N^{1353}R^{1354}I^{1355}L^{1356}S^{1357}R^{1358}N^{1359}F^{1360}V^{1361}R^{1362}L^{1363}Y^{1364}V^{1365}P^{1366}G^{1367}S^{1368}Q^{1369}L^{1370}Y^{1371}T^{1372}H^{1373}G^{1374}L^{1375}F^{1376}A^{1377}Y^{1378}G^{1379}R^{1380}M^{1381}L^{1382}L^{1383}M^{1384}F^{1385}K^{1386}$ $H^{1387}M^{1388}F^{1389}D^{1390}M^{1391}L^{1392}N^{1393}G^{1394}S^{1395}V^{1396}E^{1397}I^{1398}V^{1399}S^{1400}I^{1401}A^{1402}D^{1403}K^{1404}G^{1405}N^{1406}T^{1407}R^{1408}$ $V^{1409}H^{1410}V^{1411}K^{1412}I^{1413}Q^{1414}S^{1415}H^{1416}K^{1417}T^{1418}V^{1419}T^{1420}R^{1421}G^{1422}G^{1423}Y^{1424}E^{1425}V^{1426}D^{1427}I^{1428}V^{1429}I^{1430}C^{1431}E^{1432}M^{1433}G^{1434}N^{1435}S^{1436}I^{1437}S^{1438}A^{1439}R^{1440}K^{1441}D^{1442}I^{1443}T^{1444}S^{1445}Y^{1446}F^{1447}P^{1448}T^{1449}V^{1450}K^{1451}E^{1452}L^{1453}P^{1454}$ $G^{1455}L^{1456}T^{1457}G^{1458}M^{1459}M^{1460}S^{1461}G^{1462}G^{1463}R^{1464}R^{1465}V^{1466}F^{1467}F^{1468}S^{1469}T^{1470}A^{1471}K^{1472}F^{1473}K^{1474}A^{1475}S^{1476}$ $D^{1477}S^{1478}C^{1479}S^{1480}Y^{1481}L^{1482}M^{1483}P^{1484}Q^{1485}D^{1486}F^{1487}V^{1488}A^{1489}K^{1490}Y^{1491}I^{1492}I^{1493}A^{1494}V^{1495}D^{1496}H^{1497}I^{1498}T^{1499}S^{1500}K^{1501}S^{1502}P^{1503}E^{1504}K^{1505}K^{1506}S^{1507}Y^{1508}F^{1509}I^{1510}R^{1511}Q^{1512}G^{1513}F^{1514}E^{1515}A^{1516}E^{1517}S^{1518}D^{1519}S^{1520}M^{1521}Q^{1522}G^{1523}D^{1524}C^{1525}C^{1526}S^{1527}P^{1528}Y^{1529}V^{1530}L^{1531}F^{1532}N^{1533}S^{1534}A^{1535}S^{1536}R^{1537}A^{1538}K^{1539}I^{1540}V^{1541}F^{1542}L^{1543}H^{1544}C^{1545}A^{1546}F^{1547}F^{1548}G^{1549}G^{1550}T^{1551}A^{1552}R^{1553}V^{1554}F^{1555}A^{1556}Q^{1557}I^{1558}I^{1559}T^{1560}Q^{1561}E^{1562}D^{1563}I^{1564}M^{1565}A^{1566}T^{1567}T^{1568}P^{1569}T^{1570}T^{1571}H^{1572}A^{1573}G^{1574}R^{1575}V^{1576}T^{1577}T^{1578}E^{1579}F^{1580}P^{1581}H^{1582}T^{1583}S^{1584}L^{1585}R^{1586}D^{1587}S^{1588}S^{1589}L^{1590}P^{1591}$ $N^{1592}S^{1593}M^{1594}A^{1595}I^{1596}G^{1597}S^{1598}V^{1599}K^{1600}T^{1601}A^{1602}P^{1603}N^{1604}P^{1605}T^{1606}K^{1607}S^{1608}E^{1609}I^{1610}T^{1611}R^{1612}S^{1613}P^{1614}$ $I^{1615}H^{1616}G^{1617}C^{1618}F^{1619}P^{1620}V^{1621}R^{1622}T^{1623}A^{1624}P^{1625}A^{1626}T^{1627}L^{1628}Y^{1629}S^{1630}P^{1631}T^{1632}E^{1633}N^{1634}L^{1635}L^{1636}I^{1637}$ $K^{1637}N^{1639}A^{1640}M^{1641}K^{1642}V^{1643}T^{1644}K^{1645}N^{1646}V^{1647}E^{1648}L^{1649}L^{1650}E^{1651}E^{1652}D^{1653}L^{1654}I^{1655}D^{1656}A^{1657}C^{1658}V^{1659}$ $H^{1660}D^{1661}V^{1662}K^{1663}R^{1664}I^{1665}L^{1666}N^{1667}A^{1668}P^{1669}G^{1670}V^{1671}S^{1672}D^{1673}V^{1674}E^{1675}K^{1676}R^{1677}V^{1678}L^{1679}T^{1680}H^{1681}E^{1682}E^{1683}S^{1684}T^{1685}T^{1686}G^{1687}I^{1688}E^{1689}N^{1690}R^{1691}Q^{1692}Y^{1693}M^{1694}N^{1695}A^{1696}L^{1697}N^{1698}R^{1699}S^{1700}T^{1701}S^{1702}A^{1703}G^{1704}F^{1705}$ $P^{1706}Y^{1707}S^{1708}S^{1709}R^{1710}K^{1711}A^{1712}K^{1713}G^{1714}K^{1715}S^{1716}K^{1717}K^{1718}Q^{1719}T^{1720}W^{1721}L^{1722}G^{1723}S^{1724}E^{1725}E^{1726}F^{1727}I^{1728}V^{1729}D^{1730}N^{1731}P^{1732}D^{1733}L^{1734}K^{1735}E^{1736}H^{1737}V^{1738}E^{1739}K^{1740}I^{1741}V^{1742}D^{1743}K^{1744}A^{1745}K^{1746}D^{1747}G^{1748}I^{1749}V^{1750}$ -continued $D^{1751}V^{1752}S^{1753}L^{1754}G^{1755}I^{1756}F^{1757}A^{1758}A^{1759}T^{1760}L^{1761}K^{1762}D^{1763}E^{1764}R^{1765}R^{1766}P^{1767}L^{1768}E^{1769}K^{1770}$
$V^{1771}Q^{1772}A^{1773}N^{1774}K^{1775}T^{1776}R^{1777}V^{1778}F^{1779}A^{1780}A^{1781}S^{1782}N^{1783}Q^{1784}G^{1785}L^{1786}A^{1787}L^{1788}A^{1789}L^{1790}$
$R^{1791}R^{1792}Y^{1793}Y^{1794}L^{1795}$ $S^{1796}F^{1797}L^{1798}D^{1799}H^{1800}V^{1801}M^{1802}T^{1803}N^{1804}R^{1805}I^{1806}D^{1807}N^{1808}E^{1809}I^{1810}G^{1811}L^{1812}G^{1813}V^{1814}N^{1815}$
$V^{1816}Y^{1817}S^{1818}Y^{1819}D^{1820}W^{1821}T^{1822}R^{1823}I^{1824}V^{1825}N^{1826}K^{1827}T^{1828}K^{1829}R^{1830}V^{1831}G^{1832}D^{1833}K^{1834}V^{1835}$
$I^{1836}A^{1837}G^{1838}D^{1839}F^{1840}$ $S^{1841}N^{1842}F^{1843}D^{1844}G^{1845}S^{1846}L^{1847}N^{1848}S^{1849}Q^{1850}I^{1851}L^{1852}S^{1853}R^{1854}V^{1855}S^{1856}E^{1857}I^{1858}V^{1859}T^{1860}$
$D^{1861}W^{1862}Y^{1863}G^{1864}D^{1865}A^{1867}E^{1868}N^{1869}G^{1870}L^{1871}I^{1872}R^{1873}H^{1874}T^{1875}L^{1876}L^{1877}E^{1878}Y^{1879}L^{1880}$
$F^{1881}N^{1882}A^{1883}T^{1884}W^{1885}L^{1886}M^{1887}N^{1888}G^{1889}K^{1890}V^{1891}F^{1892}Q^{1893}L^{1894}N^{1895}H^{1896}S^{1897}Q^{1898}P^{1899}S^{1900}$
$G^{1901}N^{1902}P^{1903}L^{1904}T^{1905}T^{1906}L^{1907}I^{1908}N^{1909}C^{1910}V^{1911}Y^{1912}N^{1913}M^{1914}I^{1915}I^{1916}F^{1917}R^{1918}V^{1919}V^{1920}$
$Y^{1921}L^{1922}I^{1923}A^{1924}Q^{1925}R^{1926}E^{1927}N^{1928}G^{1929}F^{1930}P^{1931}M^{1932}T^{1933}L^{1934}S^{1935}G^{1936}F^{1937}T^{1938}T^{1939}N^{1940}$
$V^{1941}A^{1942}C^{1943}I^{1944}F^{1945}Y^{1946}G^{1947}D^{1948}D^{1949}S^{1950}L^{1951}C^{1952}S^{1953}V^{1954}S^{1955}D^{1956}K^{1957}V^{1958}S^{1959}E^{1960}$
$W^{1961}F^{1962}N^{1963}Q^{1964}H^{1965}V^{1966}I^{1967}T^{1968}R^{1969}L^{1970}M^{1971}A^{1972}T^{1973}T^{1974}G^{1975}H^{1976}E^{1977}$ $Y^{1978}T^{1979}D^{1980}E^{1981}T^{1982}K^{1983}S^{1984}G^{1985}S^{1986}P^{1987}P^{1988}P^{1989}Y^{1990}R^{1991}S^{1992}L^{1993}N^{1994}E^{1995}V^{1996}T^{1997}$
$F^{1998}L^{1999}K^{2000}R^{2001}E^{2002}F^{2003}V^{2004}L^{2005}R^{2006}D^{2007}H^{2008}F^{2009}W^{2010}I^{2011}A^{2012}P^{2013}L^{2014}S^{2015}R^{2016}N^{2017}$
$T^{2018}I^{2019}E^{2020}D^{2021}M^{2022}C^{2023}M^{2024}W^{2025}S^{2026}R^{2027}K^{2028}N^{2029}I^{2030}D^{2031}A^{2032}Q^{2033}D^{2034}A^{2035}L^{2036}L^{2037}$
$Q^{2038}T^{2039}T^{2040}R^{2041}I^{2042}A^{2043}S^{2044}F^{2045}E^{2046}A^{2047}S^{2048}L^{2049}H^{2050}E^{2051}L^{2052}N^{2053}Y^{2054}F^{2055}L^{2056}M^{2057}$
$F^{2058}C^{2059}D^{2060}V^{2061}I^{2062}K^{2063}K^{2064}A^{2065}C^{2066}R^{2067}N^{2068}$ $A^{2069}G^{2070}Y^{2071}K^{2072}E^{2073}A^{2074}C^{2075}L^{2076}H^{2077}E^{2078}L^{2079}D^{2080}C^{2081}K^{2082}S^{2083}F^{2084}L^{2085}L^{2086}A^{2087}Q^{2088}$
$Q^{2089}G^{2090}R^{2091}A^{2092}G^{2093}A^{2094}H^{2095}D^{2096}S^{2097}E^{2098}F^{2099}L^{2100}S^{2101}Q^{2102}L^{2103}L^{2104}D^{2105}L^{2106}N^{2107}$ Replikin Sequences in Amino-Terminal Portion of Peptide (1) $H^{20}R^{21}A^{22}F^{23}Y^{24}V^{25}M^{26}N^{27}D^{28}D^{29}G^{30}E^{31}N^{32}R^{33}I^{34}Y^{35}S^{36}L^{37}I^{38}G^{39}T^{40}L^{41}R^{42}R^{43}A^{44}P^{45}A^{46}F^{47}K^{48}V^{49}$ (SEQ ID NO: 114)
$G^{50}S^{51}R^{52}R^{53}Y^{54}K^{55}S^{56}H^{57}I^{58}P^{59}Y^{60}R^{61}R^{62}K^{63}$ (2) $K^{48}V^{49}G^{50}S^{51}R^{52}R^{53}Y^{54}K^{55}S^{56}H^{57}$ (SEQ ID NO: 115)

(3) $K^{48}V^{49}G^{50}S^{51}R^{52}R^{53}Y^{54}K^{55}S^{56}H^{57}I^{58}P^{59}Y^{60}R^{61}R^{62}K^{63}A^{64}T^{65}V^{66}A^{67}E^{68}L^{69}C^{70}N^{71}Q^{72}L^{73}H^{74}$ (SEQ ID NO: 116)

(4) $K^{55}S^{56}H^{57}I^{58}P^{59}Y^{60}R^{61}R^{62}K^{63}$ (SEQ ID NO: 117)

(5) $K^{55}S^{56}H^{57}I^{58}P^{59}Y^{60}R^{61}R^{62}K^{63}A^{64}T^{65}V^{66}A^{67}E^{68}L^{69}C^{70}N^{71}Q^{72}L^{73}H^{74}$ (SEQ ID NO: 118)

(6) $H^{57}I^{58}P^{59}Y^{60}R^{61}R^{62}K^{63}A^{64}T^{65}V^{66}A^{67}E^{68}L^{69}C^{70}N^{71}Q^{72}L^{73}H^{74}D^{75}R^{76}V^{77}L^{78}P^{79}F^{80}A^{81}N^{82}P^{83}Q^{84}V^{85}W^{86}K^{87}E^{88}$ (SEQ ID NO: 119)
$V^{89}I^{90}S^{91}E^{92}N^{93}K^{94}$ (7) $H^{57}I^{58}P^{59}Y^{60}R^{61}R^{62}K^{63}A^{64}T^{65}V^{66}A^{67}E^{68}L^{69}C^{70}N^{71}Q^{72}L^{73}H^{74}D^{75}R^{76}V^{77}L^{78}P^{79}F^{80}A^{81}N^{82}P^{83}Q^{84}V^{85}W^{86}K^{87}E^{88}$ (SEQ ID NO: 120)
$V^{89}I^{90}S^{91}E^{92}N^{93}K^{94}V^{95}Q^{96}P^{97}D^{98}S^{99}M^{100}L^{101}K^{102}$ (8) $H^{74}D^{75}R^{76}V^{77}L^{78}P^{79}F^{80}A^{81}N^{82}P^{83}Q^{84}V^{85}W^{86}K^{87}E^{88}V^{89}I^{90}S^{91}E^{92}N^{93}K^{94}V^{95}Q^{96}P^{97}D^{98}S^{99}M^{100}L^{101}K^{102}$ (SEQ ID NO: 121)

(9) $H^{74}D^{75}R^{76}V^{77}L^{78}P^{79}F^{80}A^{81}N^{82}P^{83}Q^{84}V^{85}W^{86}K^{87}E^{88}V^{89}I^{90}S^{91}E^{92}N^{93}K^{94}$ (SEQ ID NO: 122)

(10) $K^{145}C^{146}N^{147}D^{148}C^{149}I^{150}L^{151}K^{152}M^{153}N^{154}R^{155}N^{156}V^{157}E^{158}Y^{159}P^{160}Y^{161}H^{162}$ (SEQ ID NO: 123)

-continued

(11) $K^{469}I^{470}I^{471}D^{472}L^{473}I^{474}K^{475}E^{476}T^{477}F^{478}V^{479}S^{480}L^{481}F^{482}F^{483}A^{484}I^{485}L^{486}T^{487}K^{488}S^{489}L^{490}Y^{491}P^{492}I^{493}I^{494}Q^{495}G^{496}I^{497}S^{498}S^{499}Y^{500}A^{501}L^{502}R^{503}N^{504}N^{505}L^{506}M^{507}A^{508}N^{509}H^{510}$ (SEQ ID NO: 124)

(12) $K^{634}S^{635}R^{636}K^{637}N^{638}L^{639}D^{640}L^{641}L^{642}K^{643}E^{644}Y^{645}P^{646}S^{647}L^{648}D^{649}S^{650}L^{651}L^{652}S^{653}I^{654}F^{655}N^{656}Y^{657}F^{658}H^{659}$ (SEQ ID NO: 125)

(13) $K^{637}N^{638}L^{639}D^{640}L^{641}L^{642}K^{643}E^{644}Y^{645}P^{646}S^{647}L^{648}D^{649}S^{650}L^{651}L^{652}S^{653}I^{654}F^{655}N^{656}Y^{657}F^{658}H^{659}$ (SEQ ID NO: 126)

(14) $H^{697}R^{698}E^{699}I^{700}S^{701}S^{702}R^{703}L^{704}K^{705}E^{706}A^{707}R^{708}N^{709}S^{710}V^{711}K^{712}$ (SEQ ID NO: 127)

Replikin Sequences in Mid-Molecule Portion of Peptide

(15) $K^{705}E^{706}A^{707}R^{708}N^{709}S^{710}V^{711}K^{712}D^{713}L^{714}I^{715}A^{716}K^{717}A^{718}Q^{719}V^{720}Y^{721}L^{722}T^{723}C^{724}G^{725}D^{726}G^{727}S^{728}R^{729}V^{730}P^{731}P^{732}V^{733}V^{734}Y^{735}Y^{736}M^{737}Y^{738}G^{739}D^{740}A^{741}L^{742}C^{743}G^{744}K^{745}T^{746}E^{747}L^{748}S^{749}M^{750}A^{751}L^{752}Q^{753}D^{754}H^{755}$ (SEQ ID NO: 128)

(16) $H^{755}F^{756}A^{757}T^{758}K^{759}Y^{760}F^{761}G^{762}E^{763}V^{764}P^{765}K^{766}$ (SEQ ID NO: 129)

(17) $H^{755}F^{756}A^{757}T^{758}K^{759}Y^{760}F^{761}G^{762}E^{763}V^{764}P^{765}K^{766}K^{767}$ (SEQ ID NO: 130)

(18) $H^{755}F^{756}A^{757}T^{758}K^{759}Y^{760}F^{761}G^{762}E^{763}V^{764}P^{765}K^{766}K^{767}D^{768}V^{769}I^{770}Y^{771}S^{772}R^{773}K^{774}$ (SEQ ID NO: 131)

(19) $H^{755}F^{756}A^{757}T^{758}K^{759}Y^{760}F^{761}G^{762}E^{763}V^{764}P^{765}K^{766}K^{767}D^{768}V^{769}I^{770}Y^{771}S^{772}R^{773}K^{774}A^{775}E^{776}N^{777}E^{778}F^{779}W^{780}D^{781}G^{782}V^{783}K^{784}$ (SEQ ID NO: 132)

(20) $K^{759}Y^{760}F^{761}G^{762}E^{763}V^{764}P^{765}K^{766}K^{767}D^{768}V^{769}I^{770}Y^{771}S^{772}R^{773}K^{774}A^{775}E^{776}N^{777}E^{778}F^{779}W^{780}D^{781}G^{782}V^{783}K^{784}Q^{785}S^{786}H^{787}$ (SEQ ID NO: 133)

(21) $K^{766}K^{767}D^{768}V^{769}I^{770}Y^{771}S^{772}R^{773}K^{774}A^{775}E^{776}N^{777}E^{778}F^{779}W^{780}D^{781}G^{782}V^{783}K^{784}Q^{785}S^{786}H^{787}$ (SEQ ID NO: 134)

(22) $K^{767}D^{768}V^{769}I^{770}Y^{771}S^{772}R^{773}K^{774}A^{775}E^{776}N^{777}E^{778}F^{779}W^{780}D^{781}G^{782}V^{783}K^{784}Q^{785}S^{786}H^{787}$ (SEQ ID NO: 135)

(23) $K^{774}A^{775}E^{776}N^{777}E^{778}F^{779}W^{780}D^{781}G^{782}V^{783}K^{784}Q^{785}S^{786}H^{787}$ (SEQ ID NO: 136)

(24) $K^{774}A^{775}E^{776}N^{777}E^{778}F^{779}W^{780}D^{781}G^{782}V^{783}K^{784}Q^{785}S^{786}H^{787}K^{788}I^{789}I^{790}A^{791}Y^{792}D^{793}D^{794}V^{795}L^{796}Q^{797}I^{798}V^{799}D^{800}S^{801}A^{802}Q^{803}K^{804}P^{805}N^{806}P^{807}E^{808}L^{809}F^{810}E^{811}F^{812}I^{813}R^{814}L^{815}N^{816}N^{817}S^{818}D^{819}P^{820}Y^{821}Q^{822}V^{823}H^{824}$ (SEQ ID NO: 137)

(25) $H^{858}S^{859}A^{860}D^{861}A^{862}F^{863}R^{864}R^{865}R^{866}L^{867}D^{868}L^{869}C^{870}V^{871}Y^{872}V^{873}D^{874}V^{875}K^{876}D^{877}E^{878}F^{879}A^{880}R^{881}I^{882}V^{883}A^{884}G^{885}S^{886}K^{887}G^{888}H^{889}R^{890}K^{891}V^{892}P^{893}C^{894}E^{895}Q^{896}K^{897}I^{898}W^{899}L^{900}H^{901}Q^{902}N^{903}P^{904}G^{905}K^{906}$ (SEQ ID NO: 138)

(26) $H^{858}S^{859}A^{860}D^{861}A^{862}F^{863}R^{864}R^{865}R^{866}L^{867}D^{868}L^{869}C^{870}V^{871}Y^{872}V^{873}D^{874}V^{875}K^{876}D^{877}E^{878}F^{879}A^{880}R^{881}I^{882}V^{883}A^{884}G^{885}S^{886}K^{887}G^{888}H^{889}R^{890}K^{891}V^{892}P^{893}C^{894}E^{895}Q^{896}K^{897}$ (SEQ ID NO: 139)

(27) $K^{887}G^{888}H^{889}R^{890}K^{891}V^{892}P^{893}C^{894}E^{895}Q^{896}K^{897}I^{898}W^{899}L^{900}H^{901}Q^{902}N^{903}P^{904}G^{905}K^{906}T^{907}Q^{908}H^{909}D^{910}M^{911}K^{912}H^{913}E^{914}I^{915}V^{916}A^{917}G^{918}T^{919}Y^{920}K^{921}I^{922}T^{923}P^{924}E^{925}T^{926}A^{927}Y^{928}Y^{929}E^{930}L^{931}H^{932}$ (SEQ ID NO: 140)

(28) $K^{887}G^{888}H^{889}R^{890}K^{891}V^{892}P^{893}C^{894}E^{895}Q^{896}K^{897}I^{898}W^{899}L^{900}H^{901}$ (SEQ ID NO: 141)

(29) $K^{887}G^{888}H^{889}R^{890}K^{891}V^{892}P^{893}C^{894}E^{895}Q^{896}K^{897}$ (SEQ ID NO: 142)

-continued

(30) $K^{887}G^{888}H^{889}R^{890}K^{891}V^{892}P^{893}C^{894}E^{895}Q^{896}K^{897}I^{898}W^{899}L^{900}H^{901}Q^{902}N^{903}P^{904}G^{905}K^{906}T^{907}Q^{908}H^{909}$ (SEQ ID NO: 143)

(31) $K^{887}G^{888}H^{889}R^{890}K^{891}V^{892}P^{893}C^{894}E^{895}Q^{896}K^{897}I^{898}W^{899}L^{900}H^{901}Q^{902}N^{903}P^{904}G^{905}K^{906}T^{907}Q^{908}H^{909}D^{910}$ $M^{911}K^{912}H^{913}$ (SEQ ID NO: 144)

(32) $H^{889}R^{890}K^{891}V^{892}P^{893}C^{894}E^{895}Q^{896}K^{897}I^{898}W^{899}L^{900}H^{901}Q^{902}N^{903}P^{904}G^{905}K^{906}T^{907}Q^{908}H^{909}D^{910}M^{911}K^{912}$ $H^{913}E^{914}I^{915}V^{916}A^{917}G^{918}T^{919}Y^{920}K^{921}$ (SEQ ID NO: 145)

(33) $H^{889}R^{890}K^{891}V^{892}P^{893}C^{894}E^{895}Q^{896}K^{897}I^{898}W^{899}L^{900}H^{901}Q^{902}N^{903}P^{904}G^{905}K^{906}$ (SEQ ID NO: 146)

(34) $H^{889}R^{890}K^{891}V^{892}P^{893}C^{894}E^{895}Q^{896}K^{897}$ (SEQ ID NO: 147)

(35) $H^{889}R^{890}K^{891}V^{892}P^{893}C^{894}E^{895}Q^{896}K^{897}I^{898}W^{899}L^{900}H^{901}Q^{902}N^{903}P^{904}G^{905}K^{906}T^{907}Q^{908}H^{909}D^{910}M^{911}K^{912}$ (SEQ ID NO: 148)

(36) $K^{891}V^{892}P^{893}C^{894}E^{895}Q^{896}K^{897}I^{898}W^{899}L^{900}H^{901}$ (SEQ ID NO: 149)

(37) $K^{891}V^{892}P^{893}C^{894}E^{895}Q^{896}K^{897}I^{898}W^{899}L^{900}H^{901}Q^{902}N^{903}P^{904}G^{905}K^{906}T^{907}Q^{908}H^{909}$ (SEQ ID NO: 150)

(38) $K^{891}V^{892}P^{893}C^{894}E^{895}Q^{896}K^{897}I^{898}W^{899}L^{900}H^{901}Q^{902}N^{903}P^{904}G^{905}K^{906}T^{907}Q^{908}H^{909}D^{910}M^{911}K^{912}H^{913}$ (SEQ ID NO: 151)

(39) $H^{889}R^{890}K^{891}V^{892}P^{893}C^{894}E^{895}Q^{896}K^{897}I^{898}W^{899}L^{900}H^{901}Q^{902}N^{903}P^{904}G^{905}K^{906}T^{907}Q^{908}H^{909}D^{910}M^{911}K^{912}$ $H^{913}E^{914}I^{915}V^{916}A^{917}G^{918}T^{919}Y^{920}K^{921}I^{922}T^{923}P^{924}E^{925}T^{926}A^{927}V^{928}Y^{929}E^{930}L^{931}H^{932}$ (SEQ ID NO: 152)

(40) $K^{897}I^{898}W^{899}L^{900}H^{901}Q^{902}N^{903}P^{904}G^{905}K^{906}$ (SEQ ID NO: 153)

(41) $K^{897}I^{898}W^{899}L^{900}H^{901}Q^{902}N^{903}P^{904}G^{905}K^{906}T^{907}Q^{908}H^{909}$ (SEQ ID NO: 154)

(42) $K^{897}I^{898}W^{899}L^{900}H^{901}Q^{902}N^{903}P^{904}G^{905}K^{906}T^{907}Q^{908}H^{909}D^{910}M^{911}K^{912}H^{913}$ (SEQ ID NO: 155)

(43) $K^{897}I^{898}W^{899}L^{900}H^{901}Q^{902}N^{903}P^{904}G^{905}K^{906}T^{907}Q^{908}H^{909}D^{910}M^{911}K^{912}H^{913}E^{914}I^{915}V^{916}A^{917}G^{918}T^{919}Y^{920}$ $K^{921}I^{922}T^{923}P^{924}E^{925}T^{926}A^{927}V^{928}Y^{929}E^{930}L^{931}H^{932}$ (SEQ ID NO: 156)

(44) $H^{901}Q^{902}N^{903}P^{904}G^{905}K^{906}T^{907}Q^{908}H^{909}D^{910}M^{911}K^{912}$ (SEQ ID NO: 157)

(45) $H^{901}Q^{902}N^{903}P^{904}G^{905}K^{906}T^{907}Q^{908}H^{909}D^{910}M^{911}K^{912}H^{913}E^{914}I^{915}V^{916}A^{917}G^{918}T^{919}Y^{920}K^{921}$ (SEQ ID NO: 158)

(46) $K^{906}T^{907}Q^{908}H^{909}D^{910}M^{911}K^{912}$ (SEQ ID NO: 159)

(47) $K^{906}T^{907}Q^{908}H^{909}D^{910}M^{911}K^{912}H^{913}$ (SEQ ID NO: 160)

(48) $K^{906}T^{907}Q^{908}H^{909}D^{910}M^{911}K^{912}H^{913}E^{914}I^{915}V^{916}A^{917}G^{918}T^{919}Y^{920}K^{921}I^{922}T^{923}P^{924}E^{925}T^{926}A^{927}V^{928}Y^{929}$ (SEQ ID NO: 161)

(49) $H^{909}D^{910}M^{911}K^{912}H^{913}E^{914}I^{915}V^{916}A^{917}G^{918}T^{919}Y^{920}K^{921}$ (SEQ ID NO: 162)

(50) $K^{912}H^{913}E^{914}I^{915}V^{916}A^{917}G^{918}T^{919}Y^{920}K^{921}$ (SEQ ID NO: 163)

(51) $K^{912}H^{913}E^{914}I^{915}V^{916}A^{917}G^{918}T^{919}Y^{920}K^{921}I^{922}T^{923}P^{924}E^{925}T^{926}A^{927}V^{928}Y^{929}E^{930}L^{931}H^{932}$ (SEQ ID NO: 164)

(52) $H^{1119}W^{1120}I^{1121}S^{1122}I^{1123}S^{1124}A^{1125}V^{1126}I^{1127}I^{1128}S^{1129}A^{1130}L^{1131}L^{1132}I^{1133}G^{1134}G^{1135}V^{1136}S^{1137}$ $S^{1138}A^{1139}V^{1140}K^{1141}C^{1142}A^{1143}I^{1144}K^{1145}C^{1145}R^{1147}V^{1148}R^{1149}K^{1150}$ (SEQ ID NO: 165)

-continued

(53) $H^{1278}Q^{1279}D^{1280}F^{1281}K^{1282}P^{1283}K^{1284}D^{1285}A^{1286}I^{1287}V^{1288}E^{1289}S^{1290}I^{1291}I^{1292}D^{1293}I^{1294}V^{1295}F^{1296}T^{1297}E^{1298}$ (SEQ ID NO: 166)

$S^{1299}H^{1300}Q^{1301}D^{1302}V^{1303}R^{1304}V^{1305}K^{1306}L^{1307}H^{1308}P^{1309}Q^{1310}I^{1311}E^{1312}S^{1313}H^{1314}Q^{1315}D^{1316}F^{1317}R^{1318}A^{1319}K^{1320}N^{1321}P^{1322}I^{1323}V^{1324}E^{1325}S^{1326}R^{1327}K^{1328}$

(54) $H^{1300}Q^{1301}D^{1302}V^{1303}R^{1304}V^{1305}K^{1306}L^{1307}H^{1308}P^{1309}Q^{1310}I^{1311}E^{1312}S^{1313}H^{1314}Q^{1315}D^{1316}F^{1317}R^{1318}A^{1319}K^{1320}N^{1321}P^{1322}I^{1323}V^{1324}E^{1325}S^{1326}R^{1327}K^{1328}$ (SEQ ID NO: 167)

(55) $H^{1308}P^{1309}Q^{1310}I^{1311}E^{1312}S^{1313}H^{1314}Q^{1315}D^{1316}F^{1317}R^{1318}A^{1319}K^{1320}N^{1321}P^{1322}I^{1323}V^{1324}E^{1325}S^{1326}R^{1327}K^{1328}$ (SEQ ID NO: 168)

(56) $H^{1314}Q^{1315}D^{1316}F^{1317}R^{1318}A^{1319}K^{1320}N^{1321}P^{1322}I^{1323}V^{1324}E^{1325}S^{1326}R^{1327}K^{1328}$ (SEQ ID NO: 169)

(57) $H^{1373}G^{1374}L^{1375}F^{1376}A^{1377}Y^{1378}G^{1379}R^{1380}M^{1381}L^{1382}L^{1383}M^{1384}P^{1385}K^{1386}H^{1387}M^{1388}F^{1389}D^{1390}M^{1391}L^{1392}$ (SEQ ID NO: 170)

$N^{1393}G^{1394}S^{1395}V^{1396}E^{1397}I^{1398}V^{1399}S^{1400}I^{1401}A^{1402}D^{1403}K^{1404}G^{1405}N^{1406}T^{1407}R^{1408}V^{1409}H^{1410}V^{1411}K^{1412}$

(58) $H^{1387}M^{1388}F^{1389}D^{1390}M^{1391}L^{1392}N^{1393}G^{1394}S^{1395}V^{1396}E^{1397}I^{1398}V^{1399}S^{1400}I^{1401}A^{1402}D^{1403}K^{1404}G^{1405}N^{1406}T^{1407}R^{1408}V^{1409}H^{1410}V^{1411}K^{1412}$ (SEQ ID NO: 171)

(59) $K^{1404}G^{1405}N^{1406}T^{1407}R^{1408}V^{1409}H^{1410}V^{1411}K^{1412}$ (SEQ ID NO: 172)

(60) $K^{1404}G^{1405}N^{1406}T^{1407}R^{1408}V^{1409}H^{1410}V^{1411}K^{1412}I^{1413}Q^{1414}S^{1415}H^{1416}$ (SEQ ID NO: 173)

Replikin Sequences in Carboxy-Terminal Portion of Peptide
(61) $H^{1410}V^{1411}K^{1412}I^{1413}Q^{1414}S^{1415}H^{1416}K^{1417}T^{1418}V^{1419}T^{1420}R^{1421}G^{1422}G^{1423}Y^{1424}E^{1425}V^{1426}D^{1427}I^{1428}V^{1429}I^{1430}$ $C^{1431}E^{1432}M^{1433}G^{1434}N^{1435}S^{1436}I^{1437}S^{1438}A^{1439}R^{1440}K^{1441}D^{1442}I^{1443}T^{1444}S^{1445}Y^{1446}F^{1447}P^{1448}T^{1449}V^{1450}K^{1451}$

(62) $H^{1416}K^{1417}T^{1418}V^{1419}T^{1420}R^{1421}G^{1422}G^{1423}Y^{1424}E^{1425}V^{1426}D^{1427}I^{1428}V^{1429}I^{1430}C^{1431}E^{1432}M^{1433}G^{1434}$ (SEQ ID NO 175)

$N^{1435}S^{1436}I^{1437}S^{1438}A^{1439}R^{1440}K^{1441}D^{1442}I^{1443}T^{1444}S^{1445}Y^{1446}F^{1447}P^{1448}T^{1449}V^{1450}K^{1451}$

(63) $H^{1582}T^{1583}S^{1584}L^{1585}R^{1586}D^{1587}S^{1588}P^{1589}L^{1590}P^{1591}N^{1592}S^{1593}M^{1594}A^{1595}I^{1596}G^{1597}S^{1598}V^{1599}K^{1600}T^{1601}A^{1602}P^{1603}N^{1604}P^{1605}T^{1606}K^{1607}$ (SEQ ID NO: 176)

(64) $K^{1600}T^{1601}A^{1602}P^{1603}N^{1604}P^{1605}T^{1606}K^{1607}S^{1608}E^{1609}I^{1610}T^{1611}R^{1612}S^{1613}P^{1614}I^{1615}H^{1616}$ (SEQ ID NO: 177)

(65) $H^{1616}G^{1617}C^{1618}F^{1619}P^{1620}V^{1621}R^{1622}T^{1623}A^{1624}P^{1625}A^{1626}T^{1627}L^{1628}Y^{1629}S^{1630}P^{1631}T^{1632}E^{1633}N^{1634}L^{1635}L^{1636}I^{1637}K^{1638}N^{1639}A^{1640}M^{1641}K^{1642}V^{1643}T^{1644}K^{1645}$ (SEQ ID NO: 178)

(66) $K^{1638}N^{1639}A^{1640}M^{1641}K^{1642}V^{1643}T^{1644}K^{1645}N^{1646}V^{1647}E^{1648}L^{1649}L^{1650}E^{1651}E^{1652}D^{1653}L^{1654}I^{1655}D^{1656}A^{1657}C^{1658}V^{1659}H^{1660}$ (SEQ ID NO: 179)

(67) $K^{1638}N^{1639}A^{1640}M^{1641}K^{1642}V^{1643}T^{1644}K^{1645}N^{1646}V^{1647}E^{1648}L^{1649}L^{1650}E^{1651}E^{1652}D^{1653}L^{1654}I^{1655}D^{1656}A^{1657}C^{1658}V^{1659}H^{1660}D^{1661}V^{1662}K^{1663}R^{1664}I^{1665}L^{1666}N^{1667}A^{1668}P^{1669}G^{1670}V^{1671}S^{1672}D^{1673}V^{1674}E^{1675}K^{1676}R^{1677}V^{1678}L^{1679}T^{1680}H^{1681}$ (SEQ ID NO: 180)

-continued

(68) $H^{1681}E^{1682}E^{1683}S^{1684}I^{1685}T^{1686}G^{1687}I^{1688}E^{1689}N^{1690}R^{1691}Q^{1692}Y^{1693}M^{1694}N^{1695}A^{1696}L^{1697}N^{1698}R^{1699}$ $S^{1700}T^{1701}S^{1702}A^{1703}G^{1704}F^{1705}P^{1706}Y^{1707}S^{1708}S^{1709}R^{1710}K^{1711}A^{1712}K^{1713}G^{1714}K^{1715}S^{1716}G^{1717}K^{1718}$ (SEQ ID NO: 181)

(69) $K^{1711}A^{1712}K^{1713}G^{1714}K^{1715}S^{1716}G^{1717}K^{1718}Q^{1719}T^{1720}W^{1721}L^{1722}G^{1723}S^{1724}E^{1725}E^{1726}F^{1727}I^{1728}V^{1729}$ $D^{1730}N^{1731}P^{1732}D^{1733}L^{1734}K^{1735}E^{1736}H^{1737}$ (SEQ ID NO: 182)

(70) $K^{1735}E^{1736}H^{1737}V^{1738}E^{1739}K^{1740}I^{1741}V^{1742}D^{1743}K^{1744}$ (SEQ ID NO: 183)

(71) $H^{1737}V^{1738}E^{1739}K^{1740}I^{1741}V^{1742}D^{1743}K^{1744}A^{1745}K^{1746}D^{1747}G^{1748}I^{1749}V^{1750}D^{1751}V^{1752}S^{1753}L^{1754}G^{1755}$ $I^{1756}F^{1757}A^{1758}T^{1759}T^{1760}L^{1761}K^{1762}D^{1763}E^{1764}R^{1765}R^{1766}P^{1767}L^{1768}E^{1769}K^{1770}$ (SEQ ID NO: 184)

(72) $H^{1737}V^{1738}E^{1739}K^{1740}I^{1741}V^{1742}D^{1743}K^{1744}A^{1745}K^{1746}$ (SEQ ID NO: 185)

(73) $K^{1762}D^{1763}E^{1764}R^{1765}R^{1766}P^{1767}L^{1768}E^{1769}K^{1770}V^{1771}Q^{1772}A^{1773}N^{1774}K^{1775}T^{1776}R^{1777}V^{1778}F^{1779}A^{1780}$ $A^{1781}S^{1782}N^{1783}Q^{1784}G^{1785}L^{1786}A^{1787}L^{1788}A^{1789}L^{1790}R^{1791}Y^{1792}Y^{1793}Y^{1794}L^{1795}S^{1796}F^{1797}L^{1798}D^{1799}$ $H^{1800}$ (SEQ ID NO: 186)

(74) $H^{1800}V^{1801}M^{1802}T^{1803}N^{1804}R^{1805}I^{1806}D^{1807}N^{1808}E^{1809}I^{1810}G^{1811}L^{1812}G^{1813}V^{1814}N^{1815}Y^{1816}V^{1817}S^{1818}$ $Y^{1819}D^{1820}W^{1821}T^{1822}R^{1823}I^{1824}V^{1825}N^{1826}K^{1827}L^{1828}K^{1829}R^{1830}V^{1831}G^{1832}D^{1833}K^{1834}$ (SEQ ID NO: 187)

(75) $K^{1827}L^{1828}K^{1829}R^{1830}V^{1831}G^{1832}D^{1833}K^{1834}V^{1835}I^{1836}A^{1837}G^{1838}D^{1839}F^{1840}S^{1841}N^{1842}F^{1843}D^{1844}G^{1845}$ $S^{1846}L^{1847}N^{1848}S^{1849}Q^{1850}I^{1851}L^{1852}S^{1853}R^{1854}V^{1855}S^{1856}E^{1857}I^{1858}V^{1859}T^{1860}D^{1861}W^{1862}Y^{1863}G^{1864}$ $D^{1865}D^{1866}A^{1867}E^{1868}N^{1869}G^{1870}L^{1871}I^{1872}R^{1873}H^{1874}$ (SEQ ID NO: 188)

(76) $H^{2050}E^{2051}K^{2052}N^{2053}Y^{2054}F^{2055}L^{2056}M^{2057}F^{2058}C^{2059}D^{2060}V^{2061}I^{2062}K^{2063}K^{2064}A^{2065}C^{2066}R^{2067}N^{2068}$ $A^{2069}G^{2070}Y^{2071}K^{2072}$ (SEQ ID NO: 189)

(77) $H^{2050}E^{2051}K^{2052}N^{2053}Y^{2054}F^{2055}L^{2056}M^{2057}F^{2058}C^{2059}D^{2060}V^{2061}I^{2062}K^{2063}K^{2064}A^{2065}C^{2066}R^{2067}N^{2068}$ $A^{2069}G^{2070}Y^{2071}K^{2072}E^{2073}A^{2074}C^{2075}L^{2076}H^{2077}E^{2078}L^{2079}D^{2080}C^{2081}K^{2082}$ (SEQ ID NO: 190)

(78) $K^{2063}K^{2064}A^{2065}C^{2066}R^{2067}N^{2068}A^{2069}G^{2070}Y^{2071}K^{2072}E^{2073}A^{2074}C^{2075}L^{2076}H^{2077}$ (SEQ ID NO: 191)

(79) $K^{2063}K^{2064}A^{2065}C^{2066}R^{2067}N^{2068}A^{2069}G^{2070}Y^{2071}K^{2072}E^{2073}A^{2074}C^{2075}L^{2076}H^{2077}E^{2078}L^{2079}D^{2080}C^{2081}$ $K^{2082}S^{2083}F^{2084}L^{2085}L^{2086}A^{2087}Q^{2088}Q^{2089}G^{2090}R^{2091}A^{2092}G^{2093}A^{2094}H^{2095}$ (SEQ ID NO: 192)

(80) $K^{2064}A^{2065}C^{2066}R^{2067}N^{2068}A^{2069}G^{2070}Y^{2071}K^{2072}E^{2073}A^{2074}C^{2075}L^{2076}H^{2077}E^{2078}L^{2079}D^{2080}C^{2081}K^{2082}$ $S^{2083}F^{2084}L^{2085}L^{2086}A^{2087}Q^{2088}Q^{2089}G^{2090}R^{2091}A^{2092}G^{2093}A^{2094}H^{2095}$ (SEQ ID NO: 193)

(81) $K^{2064}A^{2065}C^{2066}R^{2067}N^{2068}A^{2069}G^{2070}Y^{2071}K^{2072}E^{2073}A^{2074}C^{2075}L^{2076}H^{2077}$ (SEQ ID NO: 194)

(82) $K^{2072}E^{2073}A^{2074}C^{2075}L^{2076}H^{2077}E^{2078}L^{2079}D^{2080}C^{2081}K^{2082}$ (SEQ ID NO: 195)

-continued

(83) $K^{2072}E^{2073}A^{2074}C^{2075}L^{2076}H^{2077}E^{2078}L^{2079}2080C^{2081}K^{2082}S^{2083}F^{2084}L^{2085}L^{2086}A^{2087}Q^{2088}Q^{2089}G^{2090}$ (SEQ ID NO: 196)

$R^{2091}A^{2092}G^{2093}A^{2094}H^{2095}$

Replikin Count=Number of Replikins per 100 amino acids=83/2107=3.9

EXAMPLE 6

Cyclic Production of West Nile Virus Replikins and Annual Human Morbidity and Methods of Prediction In a further aspect of the invention, correlation between virus biochemical cycles and virus morbidity cycles are identified and used to predict increases in morbidity in a virus in a host population. A non-limiting embodiment of the aspect of the invention provides a method of predicting an increase in morbidity in a viral disease comprising: (1) determining the mean Replikin Count in genomes of a plurality of isolates of a virus at a plurality of successive time points; (2) comparing the mean Replikin Count at at least four successive time points and identifying at least two cycles of increasing mean Replikin Counts over the at least four time points; and (4) predicting an increase in morbidity following in time the increase in mean Replikin count in at least one of said cycles. In a further non-limiting embodiment, step-wise cycles are identified between successive time points. In a further embodiment, specific conserved Replikin sequences are identified within the step-wise cycles for example, KIIQ-KAHK (SEQ ID NO: 199), HLKCRVKMEK (SEQ ID NO: 200), KLTSGHLK (SEQ ID NO: 201), and HNDKRAD-PAFVCK (SEQ ID NO: 202).

The following data in West Nile virus provides an example of cycling in mean Replikin Count in a virus wherein the cycle predicts morbidity. The data additionally further support vaccines in aquaculture in invertebrates because they support the principles upon which such Replikin vaccines and other therapies are based including, in particular, the role Replikin sequences play in virulence and morbidity in viral diseases, the correlation of Replikin Count in diseases generally with pathogenicity, and the targeting of the Replikin structure in controlling rapid replication and disease.

Cycles are detectable because of repeating conserved virus structures and continuity of the Replikin phenomenon through time. The identified cycles provide a novel method of (1) determining the growth, spread, and path of an emerging disease, (2) predicting and tracking the occurrence and intensity of viral and other organism outbreaks by tracking changes in Replikin Count manually or using computer programs such as ReplikinsForecast™ (Replikins LLC) (see, e.g., U.S. application Ser. No. 11/116,203, filed Apr. 28, 2005, which is incorporated herein in its entirety by reference), (3) designing and chemically synthesizing vaccines that contain both older conserved Replikins as well as newer ones to provide the most accurate and maximal anti-organism immune stimulating properties, (4) designing and chemically synthesizing antibodies that contain reactive sites against both older conserved Replikins and newer ones, to provide the most accurate and maximal anti-organism immune protective properties, and (5) designing and chemically synthesizing compounds that contain reactive sites against both older conserved Replikins and newer ones, to provide the most accurate and maximal anti-organism protective properties.

FIG. 7 provides the data for cycling of Replikin Count in West Nile Virus in correlation with cycling of West Nile Virus morbidity. The annual Replikin Count of the Envelope Protein of WNV (black), mean and standard deviation, is compared to the annual number of human cases in the U.S. per CDC reports (gray).

2000 to 2003:

The standard deviation of the mean of the Replikin Count of the envelope protein increases markedly from 2000 to 2001 ($p<0.001$). This change has been observed in all common strains of influenza virus (not the same virus genus as WNV) to signal rapid replication and expansion of the range of the Replikin Count, thus virus population as defined by Replikin Count, preceding virus outbreak. The increase in the mean Replikin Count from 2000 to 2003 appears to accompany, or precede, the increase in the number of human WNV cases recorded independently and published by the Center for Disease Control (CDC). The same relationship of Replikin Count to morbidity has been shown in influenza strains, for example H5N1 to human mortality, and in H3N8 equine encephalitis to horse morbidity, and in the trypanosome *Plasmodium falciparum* (malaria) to human morbidity, and to mortality rate in shrimp with shrimp virus. Since the relationship has already been demonstrated in several species, including crustacea, horses, and humans, it appears to be a broadly distributed general principle. 2004 to 2008: In 2004 and 2005, there was a decrease from 2003 in both the Replikin Count and the number of human cases of WNV. In 2006, there was an increase in the Replikin Count followed by an increase in 2007 of the number of human cases.

In FIG. 7, two cycles of Replikin concentration (count) and two cycles of WNV human morbidity may be observed. Two 'Virus Replikins Cycles', 2000-2003, and 2004-2008, as reflected by the Replikin Count of the virus, and two 'human-infectivity cycles', of the same dates, as reflected by the number of human WNV cases per year, are shown to correlate in the Figure. That Replikin Count data cycle in this manner was suggested from previous influenza virus data in previous applications, with H1N1 and H3N2, but not as clearly shown because the actual number of cases due to the H1N1 or H3N2 particular strain were not recorded (rather than just "outbreak", "epidemic" or "pandemic") as they are here for West Nile Virus.

The rising numbers for both the Replikin Count and the number of cases in the second cycle, 2004-2008, when compared to the first cycle, suggests an increased or 'improved' infective efficiency accompanying an increased Replikin Count in the second cycle, compared to the first. The drop in efficacy of the virus is probably due to the generation of resistance in the host; the subsequent rise in infectivity in the second cycle is related to the appearance of new Replikins in WNV. Once again, the close relationship of Replikins to infectivity is demonstrated; both literally rise and fall together.

Thus the present data provide direct quantitative evidence of the relationship of Replikins to infectivity at a more accurate level than previously available. For example, in the case of H5N1 influenza, the cycle began in 1996, with the Hong Kong outbreak. It was temporarily ended in 1998 by the complete culling of chickens in Hong Kong. The H5N1 clinical 'sub-cycle' resumed in 2000, continued to the present, and was predicted prospectively each year by the Replikin Count. In this case, occurring mostly in East Asian countries, H5N1 was not as subject to exact epidemiological reports by the WHO of morbidity and mortality as in the case of West Nile Virus in the U.S. as here presented, where the CDC keeps much more accurate surveillance records of the morbidity and mortality.

While not wishing to be limited by theory, the close relationship of Replikin Count to morbidity and mortality, and other evidence, has led to the hypothesis that Replikins, in addition to being closely involved in the biochemistry of rapid replication, are in fact infective units, that the viruses and trypanosomes are merely carriers of the Replikin infective units, but that other virus or trypanosome structures are needed to produce infectivity in the host.

FIG. 7 illustrates that early detection of changes in Replikin Count may be directly translated in a rapid response with vaccines to the emerging Replikin structures that may be synthesized in seven days or fewer after identification of the emerging Replikin sequences using, for example, Replikin-Forecast™ software (Replikins LLC).

The following data provides accession numbers, number of isolates, mean Replikin Count, standard deviation and significance for accession numbers available for West Nile Virus Envelope Protein from www.pubmed.com. The data is reflected in FIG. 7.

| Year | PubMed Accession Number Replikin Count West Nile Virus Envelope Protein | No. of Isolates per year | Mean Replikin Count per year | S.D. | Significance |
|---|---|---|---|---|---|
| 2000 | ABR19638 102 AAK06624 97 AAG02039 98 AAG02038 97 | 4 | 2.9 | 0.1 | low p < .001, prev p < .001 |
| 2001 | AAM70028 28 AAL07765 6 AAL07764 6 AAL07763 6 AAL07762 6 AAL07761 6 AAL14222 30 AAL14221 30 AAL14220 30 AAL14219 30 AAL14218 30 AAL14217 30 AAL14216 30 AAL14215 30 AAK58104 30 AAK58103 31 AAK58102 30 AAK58101 30 AAK58100 30 AAK58099 31 AAK58098 30 AAK58097 30 AAK58096 30 AAK52303 30 AAK52302 30 AAK52301 30 AAK52300 30 AAK62766 32 AAK62765 32 AAK62764 32 AAK62763 32 AAK62762 32 AAK62761 32 AAK62760 32 AAK62759 32 AAK62758 32 AAK62757 32 AAK62756 32 AAK91592 20 ABR19637 111 AAM81753 97 AAM81752 97 AAM81751 97 AAM81750 97 AAM81749 97 AAK67141 7 AAK67140 7 AAK67139 7 AAK67138 7 AAK67137 7 AAK67136 7 AAK67135 7 AAK67134 7 AAK67133 7 AAK67132 7 AAK67131 7 AAK67130 7 AAK67129 7 AAK67128 7 AAK67127 7 AAK67126 7 AAK67125 7 AAK67124 3 AAK67123 7 AAK67122 7 AAK67121 7 AAK67120 7 AAK67119 7 AAK67118 7 AAK67117 7 AAK67116 7 AAK67115 7 AAK67114 7 AAK67113 7 AAK67112 7 AAK67111 7 AAK67110 7 AAK67109 7 AAK67108 7 AAK67107 7 AAK67106 7 AAK67105 7 AAK67104 7 AAK67103 7 AAK67102 7 AAK67101 7 AAK67100 7 AAK67099 7 AAK67098 7 AAK67097 7 AAK67096 7 AAK67095 7 AAK67094 7 AAK67093 7 AAK67092 7 AAK67091 7 AAK67090 7 AAK67089 7 AAK67088 7 AAK67087 7 AAK67086 7 AAK67085 7 AAK67084 7 AAK67083 7 AAK67082 7 AAK67081 7 AAK67080 7 AAK67079 7 AAK67078 7 AAK67077 7 AAK67076 7 AAK67075 7 AAK67074 7 AAK67073 7 AAK67072 7 AAK67071 7 AAK67070 5 AAK67069 7 AAK67068 7 AAK67067 7 AAK67066 7 AAK67065 7 AAK67064 7 AAL87748 19 AAL87747 18 AAL87746 19 AAL87745 18 AAL37596 18 AAM21944 24 AAM21941 32 | 130 | 3.6 | 2.0 | low p < .02, prev p < .001 |
| 2002 | AAM09856 6 AAM09855 6 AAM09854 6 AAO26579 30 AAO26578 30 AAN77484 3 AAN85090 97 AAO73303 36 AAO73302 36 AAO73301 36 AAO73300 36 AAO73299 36 AAO73298 36 AAO73297 36 AAO73296 36 AAO73295 36 AAL87234 96 CAD60131 96 | 18 | 4.7 | 1.5 | low p < .001, prev p < .005 |
| 2003 | AAP20887 96 AAR10793 6 AAR10784 6 AAR17575 32 AAR17574 32 AAR17573 32 AAR17572 32 AAR17571 32 AAR17570 32 AAR17569 32 AAR17568 32 AAR17567 32 AAR17566 32 AAR17565 32 AAR17564 32 AAR17563 32 AAR17562 32 AAR17561 32 AAR17560 32 AAR17559 32 AAR17558 32 AAR17557 32 AAR17556 32 AAR17555 32 AAR17554 32 AAR17553 32 AAR17552 32 AAR17551 32 AAR17550 32 AAR17549 32 AAR17548 32 AAR17547 32 AAR17546 32 AAR17545 32 AAR17544 32 AAR17543 32 AAR17542 32 AAQ87608 16 AAQ87607 16 AAQ87606 14 AAR10804 6 AAR10803 6 AAR10802 6 AAR10801 6 AAR10800 6 AAR10799 6 AAR10798 6 AAR10797 6 AAR10796 6 AAR10795 6 AAR10794 6 AAR10792 6 AAR10791 6 AAR10790 6 AAR10789 6 AAR10788 6 AAR10787 6 AAR10786 6 AAR10785 6 AAR10783 6 AAR10782 6 AAR10781 6 AAR10780 6 AAQ88403 10 AAQ88402 10 AAX99361 97 AAR84198 36 AAQ55854 97 AAR14153 36 AAR84614 95 AAR06948 36 AAR06947 36 AAR06946 36 AAR06945 36 AAR06944 36 AAR06943 36 AAR06942 36 AAR06941 36 AAR06940 36 AAR06939 36 AAR06938 36 AAR06937 36 AAR06936 35 AAR06935 36 AAR06934 36 AAR06933 36 AAR06932 36 AAR06931 36 AAQ00999 100 AAQ00998 97 AAP22087 97 AAP22086 97 AAP22089 97 AAP22088 96 | 94 | 5.3 | 1.5 | low p < .001, prev p < .05 |
| 2004 | AAT11553 32 AAT11552 32 AAT11551 32 AAT11550 32 AAT11549 32 AAT11548 32 AAT11547 32 AAT11546 32 AAT11545 32 AAT11544 32 AAT11543 32 AAT11542 32 AAT11541 32 AAT11540 32 AAT11539 32 AAT11538 32 AAT11537 32 AAT11536 32 AAT11535 32 AAT11534 28 AAS75296 6 AAS75295 6 AAS75294 6 AAS75293 6 AAS75292 6 AAS75291 6 AAT95390 108 AAU00153 96 AAV54504 97 AAT02759 111 ABG67747 99 ABG67746 99 BAD34491 97 BAD34490 97 BAD34489 97 BAD34488 97 ABV82765 97 AAZ91684 106 AAW56064 97 AAW56066 97 AAW56065 97 | 55 | 4.2 | 1.7 | low p < .001, prev p < .001 |

| Year | PubMed Accession Number Replikin Count West Nile Virus Envelope Protein | No. of Isolates per year | Mean Replikin Count per year | S.D. | Significance |
|---|---|---|---|---|---|
| 2005 | AAW28871 97 AAV49728 6 AAV49727 6 AAV49726 6 AAV49725 6 AAV49724 6 AAT92099 97 AAT92098 97 AAV52690 96 AAV52689 97 AAV52688 97 AAV52687 97 AAV68177 97 AAX09982 97 YP_001527880 32 ABC18309 8 ABC18308 9 ABC02196 3 AAY67877 9 AAY67876 11 AAY67875 11 AAY67874 8 AAY67873 8 AAY67872 8 AAY67871 8 AAY67870 8 AAY67869 8 AAY67868 8 AAY67867 8 AAY67866 8 AAY57985 8 ABB01532 97 ABC40712 100 YP_001527877 97 ABB01533 101 ABA62343 97 AAY32590 36 AAY32589 36 YP_001527879 4 AAY55949 97 AAY29684 6 AAY29685 6 AAY29683 6 AAY29682 6 AAY29681 6 AAY29680 6 AAY29679 6 AAY29678 6 AAY29677 7 AAY29676 7 AAZ32750 97 AAZ32749 97 AAZ32748 94 AAZ32747 94 AAZ32746 94 AAZ32745 94 AAZ32744 94 AAZ32743 94 AAZ32742 94 AAZ32741 95 AAZ32740 96 AAZ32739 97 AAZ32738 97 AAZ32737 97 AAZ32736 97 AAZ32735 97 AAZ32734 96 AAZ32733 96 AAZ32732 97 AAZ32731 97 AAZ32730 97 AAZ32729 97 ABC49716 111 ABA43046 36 ABA43045 36 ABA43044 36 ABA43043 36 ABA43042 36 ABA43041 36 ABA43040 36 ABA43039 36 ABA43038 36 ABA43037 36 ABA43036 36 ABA43035 36 ABA43034 36 ABA43033 37 ABA43032 37 ABA43031 36 ABA43030 37 ABA43029 37 ABA43028 36 ABA43027 36 ABA43026 36 ABA43025 36 ABA43024 36 ABA43023 36 ABA43022 36 ABA43021 36 ABA43020 36 ABA43019 36 ABA43018 36 ABA43017 36 ABA43016 36 ABA43015 36 ABA43014 36 ABA43013 36 ABA43012 36 ABA43011 36 ABA43010 36 ABA43009 34 ABA43008 36 ABA43007 36 ABA43006 36 ABA43005 36 ABA43004 36 ABA43003 36 ABA54595 97 ABA54594 97 ABA54593 97 ABA54592 97 ABA54591 97 ABA54590 97 ABA54589 97 ABA54588 97 ABA54587 97 ABA54586 97 ABA54585 98 ABA54584 97 ABA54583 105 ABA54582 97 ABA54581 93 ABA54580 97 ABA54579 97 ABA54578 97 ABA54577 97 ABA54576 97 ABA54575 97 AAY54162 97 | 125 | 4.3 | 1.8 | low p < .001, prev p > .50 |
| 2006 | ABI81406 32 ABI81405 32 ABI81404 32 ABI81403 32 ABI81402 32 ABI81401 32 ABI81400 32 ABI81399 32 ABI81398 32 ABI81397 32 ABI81396 32 ABI81395 32 ABI81394 32 ABI81393 32 ABI81392 32 ABI81391 32 ABI81390 32 ABI81389 32 ABI81388 32 ABI81387 32 ABI81386 32 ABI81385 32 ABI81384 32 ABI81383 32 ABI81382 32 ABI81381 32 ABI81380 32 ABI81379 32 ABI81378 32 ABI81377 32 ABI81376 32 ABI81375 32 ABI81374 32 ABI81373 32 ABI81372 32 ABI81371 32 ABI81370 32 ABI81369 32 ABI81368 32 ABI81367 32 ABI81366 32 ABI81365 32 ABI81364 32 ABI81363 32 ABI81362 32 ABI81361 32 ABI81360 32 ABI81359 32 ABI81358 32 ABI81357 32 ABI81356 32 ABI81355 32 ABI81354 32 ABI81353 32 ABI81351 32 ABI81350 32 ABI81349 32 ABI81348 32 ABI81347 32 ABI81346 32 ABI81345 32 ABI81344 32 ABI81343 32 ABI81342 32 ABI81341 32 ABI81340 32 ABI81339 32 ABI81338 32 ABI81337 32 ABI81336 32 ABI81335 32 ABI81334 32 ABI81333 32 ABI81332 32 ABI81331 32 ABI81330 32 ABI81329 32 ABI81328 32 ABI81327 32 ABI81326 32 ABI81325 32 ABI81324 32 ABI81323 32 ABI81322 32 ABI81321 34 ABI81320 32 ABI81319 32 ABI81318 32 ABI81317 32 ABI81316 32 ABI81315 32 ABI81314 32 ABI81313 32 ABI81312 32 ABI81311 32 ABI81310 32 ABI81309 32 ABI81308 32 ABI81307 32 ABI81306 32 ABI81305 32 ABI81304 32 ABI81303 32 ABI81302 32 ABI81301 32 ABI81300 32 ABI81299 32 ABI81298 32 ABI81297 32 ABI81296 32 ABI81295 32 ABI81294 32 ABI81293 32 ABI81292 32 ABI81291 32 ABI81290 32 ABI81289 32 ABI81288 32 ABI81287 32 ABI81286 32 ABI81285 32 ABI81284 32 ABI81283 32 ABI81282 32 ABI81281 32 ABI81280 32 ABI81279 32 ABI81278 32 ABI81277 32 ABI81276 32 ABI81275 32 ABI81274 32 ABI81273 32 ABI81272 32 ABI81271 32 ABI81270 32 ABI81269 32 ABI81268 32 ABI81267 32 ABI81266 32 ABI81265 32 ABI81264 32 ABI81263 32 ABI81262 32 ABI81261 32 ABI81260 32 ABI81259 32 ABI81258 32 ABI81257 32 ABI81256 32 ABI81255 32 ABI81254 32 ABI81253 32 ABI81252 32 ABI81251 32 ABI81250 32 ABI81249 32 ABI81248 32 ABI81247 32 ABI81246 32 ABI81245 32 ABI81244 32 ABI81243 32 ABI81242 32 ABI81241 32 ABI81240 32 ABI81239 32 ABI81238 32 ABI81237 32 ABI81236 32 ABI81235 32 ABI81234 32 ABI81233 32 ABI81232 32 ABI81231 32 ABI81230 32 ABI81229 32 ABI81228 32 ABJ90133 32 ABJ90132 32 ABJ90131 32 ABJ90130 32 ABJ90129 32 ABJ90128 32 ABJ90127 32 ABJ90126 32 ABJ90125 32 ABJ90124 32 ABJ90123 32 ABJ90122 32 ABJ90121 32 ABJ90120 32 ABJ90119 32 ABJ90118 32 ABJ90117 32 ABJ90116 32 ABJ90115 32 ABJ90114 32 ABJ90113 32 ABJ90112 32 ABJ90111 32 ABJ90110 32 ABJ90109 32 ABJ90108 32 ABJ90107 32 ABJ90106 32 ABJ90105 32 ABJ90104 32 ABJ90103 32 ABJ90102 32 ABJ90101 32 ABJ90100 32 ABJ90099 32 ABJ90098 32 ABJ90097 32 ABJ90096 32 ABJ90095 32 ABJ90094 32 ABJ90093 32 ABJ90092 32 ABJ90091 32 ABJ90090 32 ABJ90089 32 ABJ90088 32 ABJ90087 32 ABJ90086 32 ABJ90085 32 ABJ90084 32 ABJ90083 32 ABJ90082 32 | 312 | 6.0 | 1.3 | low p < .001, prev p < .001 |

| Year | PubMed Accession Number Replikin Count West Nile Virus Envelope Protein | No. of Isolates per year | Mean Replikin Count per year | S.D. | Significance |
|---|---|---|---|---|---|
| | ABJ90081 32 ABJ90080 32 ABJ90079 32 ABJ90078 32 ABJ90077 32 ABJ90076 32 ABJ90075 32 ABJ90074 32 ABJ90073 32 ABJ90072 32 ABJ90071 32 ABJ90070 32 ABJ90069 32 ABJ90068 32 ABJ90067 32 ABJ90066 32 CAL49454 98 ABI97486 99 ABG36517 36 ABG81344 92 ABG81343 97 ABG81342 97 ABG81341 97 ABG81340 99 ABG76816 41 ABG76815 43 ABG76814 43 ABG76813 43 ABG76812 43 ABG76811 43 ABG76810 43 ABG76809 43 ABG76808 43 ABG76807 43 ABG76806 43 ABG76805 43 ABG76804 43 ABG76803 43 ABG76802 43 ABG76801 43 ABG76800 43 ABG76799 43 ABG76798 43 ABG76797 43 ABG76796 43 ABG76795 43 ABI26622 40 ABI26621 40 ABD19642 97 ABD19641 97 ABD19640 97 ABD19513 97 ABD19512 96 ABD19511 97 ABD19510 97 ABD85083 98 ABD85082 93 ABD85081 97 ABD85080 97 ABD85078 97 ABD85077 97 ABD85076 97 ABD85075 97 ABD85074 99 ABD85073 97 ABD85072 99 ABD85070 97 ABD85069 96 ABD85068 97 ABD85067 97 ABD85066 95 ABD85065 97 ABD85064 97 ABD67762 97 ABD67761 97 ABD67760 97 ABD67759 97 ABD67758 97 ABD67757 97 | | | | |
| 2007 | ABR19639 111 ABV22897 97 ABU54838 97 ABU52997 98 ABQ52692 97 ABO69610 36 ABO69609 36 ABO69608 36 ABO69607 36 ABO69606 36 ABO69605 36 ABO69604 36 ABO69603 36 ABO69602 36 ABO69601 36 ABO69600 36 ABO69599 36 ABO69598 36 ABO69597 36 ABO69596 36 ABO69595 36 ABO69594 36 ABO69593 36 ABO69592 36 ABU41789 114 CAM91200 97 ABR10608 56 | (Incomplete) 27 | (Incomplete) 4.6 | (Incomplete) 1.2 | (Incomplete) low p < .001, prev p < .001 |
| 2008 | ABZ10682 21 ABZ10681 29 ABZ10680 29 ABZ10679 29 ABZ10678 29 | (Incomplete) 5 | (Incomplete) 5.5 | (Incomplete) 0.7 | (Incomplete) low p < .002, prev p < .04 |

Examples of Conserved WNV Replikins

Sequence History by Year: Note that entries for years before WNV appeared in the U.S., approx. 2000, are from non-U.S. specimens, as from the Middle East and Africa.

KIIQKAHK (SEQ ID NO: 199)
All occurrences of the sequence by year:
1988
P14335 position 835, BAA00176 position 835.

1999
AAF20205 position 835, AAF20092 position 835,

AAG02040 position 835, AAF18443 position 835.

2000
AAK06624 position 835, AAG02039 position 835,

AAG02038 position 835.

2001
AAM81753 position 835, AAM81752 position 835,

AAM81751 position 835, AAM81750 position 835,

AAM81749 position 835.

2002
AAN85090 position 835, AAL87234 position 835,

CAD60131, position 835.

2003
AAP20882 position 835, AAX99361 position 835,

AAQ55854 position 835, AAR84614 position 835,

AAQ00999 position 835, XAP22087 position 835,

AAP22086 position 835, AAP22089 position 835.

2004
AAU00153 position 835, AAV54504 position 835,

ABG67747 position 835, ABG67746 position 835,

BAD34491 position 835, BAD34490 position 835,

BAD34489 position 835, BAD34488 position 835,

ABV82765 position 835, AAW56064 position 835,

AAW56066 position 835, AAW56065 position 835,

AAW28871 position 835, AA197099 position 835,

AAT92098 position 835, AAV52690 position 835,

AAV52689 position 835, AAV52688 position 835,

AAV52687 position 835, AAV68177 position 835,

AAX09982 position 835.

2005
YP_001527877 position 835, ABB01533 position 835,

ABA62343 position 835, AAY55949 position 835,

AAZ32750 position 835, AAZ32749 position 835,

AAZ32748 position 835, AAZ32747 position 835,

AAZ32746 position 835, AAZ32745 position 835,

AAZ32744 position 835, AAZ32743 position 835,

AAZ32747 position 835, AAZ32741 position 835,

AAZ32740 position 835, AAZ32739 position 835,

AAZ32738 position 835, AAZ32737 position 835,

AAZ32736 position 835, AAZ32735 position 835,

AAZ32734 position 835, AAZ37733 position 835,

-continued

AAZ32732 position 835, AAZ32731 position 835,
AAZ32730 position 835, AAZ32729 position 835,
ABA54595 position 835, ABA54594 position 835,
ABA54593 position 835, ABA54592 position 835,
ABA54591 position 835, ABA54590 position 835,
ABA54589 position 835, ABAA5488 position 835,
ABA54587 position 835, ABAA54586 position 835,
ABA54585 position 835, ABA54584 position 835,
ABA54583 position 835, ABA54582 position 835,
ABA54581 position 835, ABA54580 position 835,
ABA54579 position 835, ABA54578 position 835,
ABA54577 position 835, ABA54576 position 835,
ABA54575 position 835, AAY54162 position 835.
2006
CAL49454 position 835, ABI97486 position 835,
ABG81344 position 835, ABG81343 position 835,
ABG81342 position 835, ABG81341 position 835,
ABG81340 position 835, ABG76816 position 835,
ABG76815 position 835, ABG76814 position 835,
ABG76813 position 835, ABG76812 position 835,
ABG76811 position 835, ABG76810 position 835,
ABG76809 position 835, ABG76808 position 835,
ABG76807 position 835, ABG76806 position 835,
ABG76805 position 835, ABG76804 position 835,
ABG76803 position 835, ABG76802 position 835,
ABG76801 position 835, ABG76800 position 835,
ABG76799 position 835, ABG76798 position 835,
ABG76797 position 835, ABG76796 position 835,
ABG76795 position 835, ABD19642 position 835,
ABD19641 position 835, ABD19640 position 835,
ABD19513 position 835, ABD19512 position 835,
ABD19511 position 835, ABD19510 position 835,
ABD85083 position 835, ABD85082 position 835,
ABD85081 position 835, ABD85080 position 835,
ABD85078 position 835, ABD85077 position 835,
ABD85076 position 835, ABD85075 position 835,
ABD85074 position 835, ABD85073 position 835,
ABD85072 position 835, ABD85070 position 835,
ABD85069 position 835, ABD85068 position 835,
ABD85067 position 835, ABD85066 position 835,
ABD85065 position 835, ABD85064 position 835,
ABD67762 position 835, ABD67761 position 835,
ABD67760 position 835, ABD67759 position 835,
ABD67758 position 835, ABD67757 position 835,
ABD67756 position 835.
2007
ABV22897 position 835, ABU54838 position 835,
ABU52997 position 835, ABQ52692 position 835,
CAM91200 position 835, ABR10608 position 377.

Sequence History by Year
HLKCRVKMEK (SEQ ID NO: 200)
All occurences of the sequence by year:
1982
ABC497717 position 575.
1985
P06935 position 571, AAA48498 position 571.
1988
P14335 position 575, BAA00176 position 575.
1989
ABR19636 position 575.
1993
NP_776014 position 281, NP_041724 position 571.
1998
AAD28624 position 550.
1999
AAD31720 position 285, AAF20205 position 575,
AAF26360 position 575, AAD28623 position 550,
AAF20092 position 575, AAG02040 position 575,
AAF18443 position 575.
2000
ABR19638 position 575, AAK06624 position 575,
AAG02039 position 575, AAG02038 position 575.
2001
AAM70028 position 285, AAL14222 position 285,
AAL14221 position 285, AAL14220 position 285,
AAL14219 position 285, AAL14218 position 285,
AAL14217 position 285, AAL14216 position 285,
AAL14215 position 285, AAK58104 position 285,
AAK58103 position 285, AAK58102 position 285,
AAK58101 position 285, AAK58100 position 285,
AAK58099 position 285, AAK58098 position 285,
AAK58097 position 285, AAK58096 position 285,
AAK52303 position 285, AAK52302 position 285,
AAK52301 position 285, AAK52300 position 285,
AAK62766 position 285, AAK62765 position 285,
AAK62764 position 285, AAK62763 position 285,
AAK62762 position 285, AAK62761 position 285,
AAK67760 position 285, AAK62759 position 285, -continued AAK62758 position 285, AAK62757 position 285,
AAK62756 position 285, AAK91592 position 176,
ABR19637 position 575, AAM81753 position 575,
AAM81752 position 575, AAM81751 position 575,
AAM81750 position 575, AAM81749 position 575,
AAM21944 position 198, AAM21941 position 264.

2002
AAO26579 position 285, AAO26578 position 285,
AAN85090 position 575, AAO73303 position 452,
AAO73302 position 285, AAO73301 position 452,
AAO73300 position 452, AAO73299 position 452,
AAO73298 position 285, AAO73297 position 452,
AAO73296 position 452, AAO73295 position 452,
AAL87234 position 285, CAD60131 position 575.

2003
AAP20887 position 575, AAR10793 position 128,
AAR10784 position 128, AAR17575 position 285,
AAR17574 position 285, AAR17573 position 285,
AAR17572 position 285, AAR17571 position 285,
AAR17570 position 285, AAR17569 position 285,
AAR17568 position 285, AAR17567 position 285,
AAR17566 position 285, AAR17565 position 285,
AAR17564 position 285, AAR17563 position 285,
AAR17562 position 285, AAR17561 position 285,
AAR17560 position 285, AAR17559 position 285,
AAR17558 position 285, AAR17557 position 285,
AAR17556 position 285, AAR17545 position 285,
AAR17554 position 285, AAR17553 position 285,
AAR17552 position 285, AAR17555 position 285,
AAR17550 position 285, AAR17549 position 285,
AAR17548 position 285, AAR17547 position 285,
AAR17546 position 285, AAR17545 position 285,
AAR17544 position 285, AAR17543 position 285,
AAR17542 position 285, AAO87608 position 194,
AAO87607 position 194, AAO87606 position 58,
AAR10804 position 128, AAR10803 position 128,
AAR10802 position 128, AAR10801 position 128,
AAR10800 position 128, AAR10799 position 128,
AAR10798 position 128, AAR10797 position 128,
AAR10796 position 128, AAR10795 position 128,
AAR10794 position 128, AAR10792 position 128,
AAR10791 position 128, AAR10790 position 128,
AAR10789 position 128, AAR10788 position 128,
AAR10787 position 128, AAR10786 position 128,
AAR10785 position 128, AAR10783 position 128,
AAR10782 position 128, AAR10781 position 128,
AAR10780 position 128, AAX99361 position 575,
AAR84198 position 452, AAO55854 position 575
AAR14153 position 452, AAR84614 position 575,
AAR06948 position 452, AAR06947 position 452,
AAR06946 position 452, AAR06945 position 452,
AAR06944 position 452, AAR06943 position 452,
AAR06942 position 452, AAR06941 position 452,
AAR06940 position 452, AAR06939 position 452,
AAR06938 position 452, AAR06937 position 452,
AAR06936 position 452, AAR06935 position 452,
AAR06934 position 452, AAR06933 position 452,
AAR06932 position 452, AAR06931 position 452,
AAO00999 position 575, AAO00998 position 575,
AAP22087 position 575, AAP22086 position 575,
AAP22089 position 575, AAP22088 position 572, 2004
AAT11553 position 285, AAT11552 position 285,
AAT11551 position 285, AAT11550 position 285,
AAT11549 position 285, AAT11548 position 285,
AAT11547 position 285, AAT11546 position 285,
AAT11545 position 285, AAT11544 position 285,
AAT11543 position 285, AAT11542 position 285,
AAT11541 position 285, AAT11540 position 285,
AAT11539 position 285, AAT11538 position 285,
AAT11537 position 285, AAT11536 position 285,
AAT11535 position 285, AAT11534 position 285,
AAS75296 position 128, AAS75295 position 128,
AAS75294 position 128, AAS75293 position 128,
AAS75292 position 128, AAS75291 position 128,
AAT95390 position 575, AAU00153 position 575,
AAV54504 position 575, AAT02759 position 571,
ABG67747 position 575, ABG67746 position 575,
BAD34491 position 575, BAD34490 position 575,
BAD34489 position 575, BAD34488 position 575,
ABV82765 position 575, AAZ91684 position 575,
AAW56064 position 575, AAW56066 position 575, -continued AAW56065 position 575, AAW28871 position 575, AAT92099 position 575, AAT92098 position 575, AAV52690 position 575, AAV52689 position 575, AAV52688 position 575, AAV52687 position 575, AAV68177 position 575, AAX09982 position 575.

2005
YP_001527880 position 285, ABC40712 position 575, YP_001527877 position 575, ABB01533 position 575, ABA62343 position 575, AAY32590 position 452, AAY32589 position 452, AAY55949 position 575, AAZ32750 position 575, AAZ32749 position 575, AAZ32740 position 575, AAZ32739 position 575, AAZ32738 position 575, AAZ32737 position 575, AAZ32736 position 575, AAZ32735 position 575, AAZ32734 position 575, AAZ32733 position 575, AAZ32732 position 575, AAZ32731 position 575, AAZ32730 position 575, AAZ32729 position 575, ABC49716 position 571, ABA43046 position 452, ABA43045 position 452, ABA43044 position 452, ABA43043 position 452, ABA43042 position 452, ABA43041 position 452, ABA43040 position 452, ABA43039 position 452, ABA43038 position 452, ABA43037 position 452, ABA43036 position 452, ABA43035 position 452, ABA43034 position 452, ABA43033 position 452, ABA43032 position 452, ABA43031 position 452, ABA43030 position 452, ABA43029 position 452, ABA43028 position 452, ABA43027 position 452, ABA43026 position 452, ABA43025 position 452, ABA43024 position 452, ABA43023 position 452, ABA43022 position 452, ABA43021 position 452, ABA43020 position 452, ABA43019 position 452, ABA43018 position 452, ABA43017 position 452, ABA43016 position 452, ABA43015 position 452, ABA43014 position 452, ABA43013 position 452, ABA43012 position 452, ABA43011 position 452, ABA43010 position 452, ABA43009 position 452, ABA43008 position 452, ABA43007 position 452, ABA43006 position 452, ABA43005 position 452, ABA43004 position 452, ABA43003 position 452, ABA54595 position 575, ABA54594 position 575, ABA54593 position 575, ABA54592 position 575, ABA54591 position 575, ABA54590 position 575, ABA54589 position 575, ABA54588 position 575, ABA54587 position 575, ABA54586 position 575, ABA54585 position 575, ABA54584 position 575, ABA54583 position 575, ABA54582 position 575, ABA54581 position 575, ABA54580 position 575, ABA54579 position 575, ABA54578 position 575, ABA54577 position 575, ABA54576 position 575, ABA54575 position 575, AAY54162 position 575.

2006
ABI81406 position 275, ABI81405 position 275, ABI81404 position 275, ABI81403 position 275, ABI81402 position 275, ABI81401 position 275, ABI81400 position 275, ABI81399 position 275, ABI81398 position 275, ABI81397 position 275, ABI81396 position 275, ABI81395 position 275, ABI81394 position 275, ABI81393 position 275, ABI81392 position 275, ABI81391 position 275, ABI81390 position 275, ABI81389 position 275, ABI81388 position 275, ABI81387 position 275, ABI81386 position 275, ABI81385 position 275, ABI81384 position 275, ABI81383 position 275, ABI81382 position 275, ABI81381 position 275, ABI81380 position 275, ABI81379 position 275, ABI81378 position 275, ABI81377 position 275, ABI81376 position 275, ABI81375 position 275, ABI81374 position 275, ABI81373 position 275, ABI81372 position 275, ABI81371 position 275, ABI81370 position 275, ABI81369 position 275, ABI81368 position 275, ABI81367 position 275, ABI81366 position 275, ABI81365 position 275, ABI81364 position 275, ABI81363 position 275, ABI81362 position 275, ABI81361 position 275, ABI81360 position 275, ABI81359 position 275, ABI81358 position 275, ABI81357 position 275, ABI81356 position 275, ABI81355 position 275, ABI81354 position 275, ABI81353 position 275, ABI81351 position 275, ABI81350 position 275, ABI81349 position 275, ABI81348 position 275, ABI81347 position 275, ABI81346 position 275, -continued ABI81345 position 275, ABI81344 position 275,
ABI81343 position 275, ABI81342 position 275,
ABI81341 position 275, ABI81340 position 275,
ABI81339 position 275, ABI81338 position 275,
ABI81337 position 275, ABI81336 position 275,
ABI81335 position 275, ABI81334 position 275,
ABI81333 position 275, ABI81332 position 275,
ABI81331 position 275, ABI81330 position 275,
ABI81329 position 275, ABI81328 position 275,
ABI81327 position 275, ABI81326 position 275,
ABI81325 position 275, ABI81324 position 275,
ABI81323 position 275, ABI81322 position 275,
ABI81321 position 275, ABI81320 position 275,
ABI81319 position 275, ABI81318 position 275,
ABI81317 position 275, ABI81316 position 275,
ABI81315 position 275, ABI81314 position 275,
ABI81313 position 275, ABI81312 position 275,
ABI81311 position 275, ABI81310 position 275,
ABI81309 position 275, ABI81308 position 275,
ABI81307 position 275, ABI81306 position 275,
ABI81305 position 275, ABI81304 position 275,
ABI81303 position 275, ABI81302 position 275,
ABI81301 position 275, ABI81300 position 275,
ABI81299 position 275, ABI81298 position 275,
ABI81297 position 275, ABI81296 position 275,
ABI81295 position 275, ABI81294 position 275,
ABI81293 position 275, ABI81292 position 275,
ABI81291 position 275, ABI81290 position 275,
ABI81289 position 275, ABI81288 position 275,
ABI81287 position 275, ABI81286 position 275,
ABI81285 position 275, ABI81284 position 275,
ABI81283 position 275, ABI81282 position 275,
ABI81281 position 275, ABI81280 position 275,
ABI81279 position 275, ABI81278 position 275,
ABI81277 position 275, ABI81276 position 275,
ABI81275 position 275, ABI81274 position 275,
ABI81273 position 275, ABI81272 position 275,
ABI81271 position 275, ABI81270 position 275,
ABI81269 position 275, ABI81268 position 275,
ABI81267 position 275, ABI81266 position 275,
ABI81265 position 275, ABI81264 position 275, -continued ABI81263 position 275, ABI81262 position 275,
ABI81261 position 275, ABI81260 position 275,
ABI81259 position 275, ABI81258 position 275,
ABI81257 position 275, ABI81256 position 275,
ABI81255 position 275, ABI81254 position 275,
ABI81253 position 275, ABI81252 position 275,
ABI81251 position 275, ABI81250 position 275,
ABI81249 position 275, ABI81248 position 275,
ABI81247 position 275, ABI81246 position 275,
ABI81245 position 275, ABI81244 position 275,
ABI81243 position 275, ABI81242 position 275,
ABI81241 position 275, ABI81240 position 275,
ABI81239 position 275, ABI81238 position 275,
ABI81237 position 275, ABI81236 position 275,
ABI81235 position 275, ABI81234 position 275,
ABI81233 position 275, ABI81232 position 275,
ABI81231 position 275, ABI81230 position 275,
ABI81229 position 275, ABI81228 position 275,
ABI81133 position 275, ABI81901 position 275,
ABJ90131 position 309, ABJ90130 position 309,
ABJ90129 position 309, ABJ90128 position 309,
ABJ90127 position 309, ABJ90126 position 309,
ABJ90125 position 309, ABJ90124 position 309,
ABJ90123 position 309, ABJ90122 position 309,
ABJ90121 position 309, ABJ90120 position 309,
ABJ90119 position 309, ABJ90118 position 309,
ABJ90117 position 309, ABJ90116 position 309,
ABJ90115 position 309, ABJ90114 position 309,
ABJ90113 position 309, ABJ90112 position 309,
ABJ90111 position 309, ABJ90110 position 309,
ABJ90109 position 309, ABJ90108 position 309,
ABJ90107 position 309, ABJ90106 position 309,
ABJ90105 position 309, ABJ90104 position 309,
ABJ90103 position 309, ABJ90102 position 309,
ABJ90101 position 309, ABJ90100 position 309,
ABJ90099 position 309, ABJ90098 position 309,
ABJ90097 position 309, ABJ90096 position 309,
ABJ90095 position 309, ABJ90094 position 309,
ABJ90093 position 309, ABJ90092 position 309,
ABJ90091 position 309, ABJ90090 position 309, -continued ABJ90088 position 309, ABJ90087 position 309, ABJ90086 position 309, ABJ90085 position 309, ABJ90084 position 309, ABJ90083 position 309, ABJ90082 position 309, ABJ90081 position 309, ABJ90080 position 309, ABJ90079 position 309, ABJ90078 position 309, ABJ90077 position 309, ABJ90076 position 309, ABJ90075 position 309, ABJ90074 position 309, ABJ90073 position 309, ABJ90072 position 309, ABJ90071 position 309, ABJ90070 position 309, ABJ90069 position 309, ABJ90068 position 309, ABJ90067 position 309, ABJ90066 position 309, CAL49454 position 575, ABI97486 position 575, ABG36517 position 452, ABG81344 position 575, ABG81343 position 575, ABG81342 position 575, ABG81341 position 575, ABG81340 position 575, ABG76816 position 575, ABG76815 position 575, ABG76814 position 575, ABG76813 position 575, ABG76812 position 575, ABG76811 position 575, ABG76810 position 575, ABG76809 position 575, ABG76808 position 575, ABG76807 position 575, ABG76806 position 575, ABG76805 position 575, ABG76804 position 575, ABG76803 position 575, ABG76802 position 575, ABG76801 position 575, ABG76800 position 575, ABG76799 position 575, ABG76798 position 575, ABG76797 position 575, ABG76796 position 575, ABG76795 position 575, ABI26622 position 575, ABI26621 position 575, ABD19642 position 575, ABD19641 position 575, ABD19640 position 575, ABD19513 position 575, ABD19512 position 575, ABD19511 position 575, ABD19510 position 575, ABD85083 position 575, ABD85082 position 575, ABD85081 position 575, ABD85080 position 575, ABD85078 position 575, ABD85077 position 575, ABD85076 position 575, ABD85075 position 575, ABD85074 position 575, ABD85073 position 575, ABD85072 position 575, ABD85070 position 575, ABD85069 position 575, ABD85068 position 575, ABD85067 position 575, ABD85066 position 575, ABD85065 position 575, ABD85064 position 575, ABD67762 position 575, ABD67761 position 575, -continued ABD67760 position 575, ABD67759 position 575, ABD67758 position 575, ABD67757 position 575, ABD67756 position 575, CAM90885 position 285, CAM90884 position 285.

2007
ABR19639 position 575, ABV22897 position 575, ABU54838 position 575, ABU52997 position 575, ABO52692 position 575, ABO69610 position 452, ABO69609 position 452, ABO69608 position 452, ABU69607 position 452, ABO69606 position 452, ABO69605 position 452, ABO69604 position 452, ABO69603 position 452, ABO69602 position 452, ABO69601 position 452, ABO69600 position 452, ABO69599 position 452, ABO69598 position 452, ABO69597 position 452, ABO69596 position 452, ABO69595 position 452, ABO69594 position 452, ABO69593 position 452, ABO69592 position 452, ABU41789 position 575, CAMP1200 position 575.

2008
ABZ10682 position 285, A13Z10681 position 285, ABZ10680 position 285, ABZ10679 position 285, ABZ10678 position 285.

Sequence History by Year
KLTSGHLK (SEQ ID NO: 201)
All occurences of the sequence by year:
1982
ABC49717 position 570.

1985
P06935 position 566, AAA48498 position 566.

1988
P14335 position 570, BAA00176 position 570.

1989
ABR19636 position 570.

1993
NP_776014 position 276, NP_041724 position 566.

1998
AAD28624 position 545, AAW81711 position 570.

1999
AAD21720 position 280, AAF20205 position 570, AAF26360 position 570, AAD28623 position 545, AAF20092 position 570, AAG02040 position 570, AAF18443 position 570.

2000
ABR19638 position 570, AAK06624 position 570, AA602039 position 570, AAG02038 position 570.

2001
AAM70028 position 280, AAL14222 position 280, AAL14221 position 280, AAL14220 position 280, AAL14219 position 280, AAL14218 position 280, AAL14217 position 280, AAL14216 position 280, AAL14215 position 280, AAK58104 position 280, AAK58103 position 280, AAK58102 position 280, AAK58101 position 280, AAK58100 position 280, AAK58099 position 280, AAK58098 position 280, AAK58097 position 280, AAK58096 position 280, AAK52303 position 280, AAK52302 position 280, AAK52301 position 280, AAK52300 position 280, AAK62766 position 280, AAK62765 position 280, AAK62764 position 280, AAK62763 position 280, AAK62766 position 280, AAK62761 position 280, AAK62760 position 280, AAK62759 position 280, AAK62758 position 280, AAK62757 position 280, AAK62756 position 280, AAK91592 position 171, ABR19637 position 570, AAM81753 position 570, AAM81752 position 570, AAM81751 position 570, AAM81750 position 570, AAM81749 position 570, AAM21944 position 193, AAM21941 position 259.

2002
AAO26579 position 280, AAO26578 position 280, AAN77484 position 129, AAN85090 position 570, AAO73303 position 447, AAO73302 position 447, AAO73301 position 447, AAO73300 position 447, AAO73299 position 447, XAO73298 position 447, AAO73297 position 447, AAO73296 position 447, AAO73295 position 447, AAL87234 position 570, CAD60131 position 570.

2003
AAP20887 position 570, AAR10793 position 123, AAR10784 position 123, AAR17575 position 280, AAR17574 position 280, AAR17573 position 280, AAR17572 position 280, AAR17571 position 280, AAR17570 position 280, AAR17569 position 280, AAR17568 position 280, AARI7567 position 280, AAR17566 position 280, AAR17565 position 280, AAR17564 position 280, AAR17563 position 280, AAR17562 position 280, AAR17561 position 280, AAR17560 position 280, AAR17559 position 280, AAR17558 position 280, AAR17557 position 280, AAR17556 position 280, AAR17555 position 280, AAR17554 position 280, AAR17553 position 280, AAR17552 position 280, AAR17551 position 280, AAR17550 position 280, AAR17549 position 280, AAR17548 position 280, AAR17547 position 280, AAR17546 position 280, AAR17545 position 280, AAR17544 position 280, AAR17543 position 280, AAR17542 position 280, AAO87608 position 189, AAQ87607 position 189, AAO87606 position 53, AAR10804 position 123, AAR10803 position 123, AAR10802 position 123, AAR10801 position 123, AAR10800 position 123, AAR10799 position 123, AAR10798 position 123, AAR10797 position 123, AAR10796 position 123, AAR10795 position 123, AAR10794 position 123, AAR10792 position 123, AAR10791 position 123, AAR10790 position 123, AAR10789 position 123, AAR10788 position 123, AAR10787 position 123, AAR10786 position 123, AAR10785 position 123, AAR10783 position 123, AAR10782 position 123, AAR10781 position 123, AAR10780 position 123, AAX99361 position 570, AAR84198 position 447, AAO55854 position 570, AAR14153 position 447, AAR84614 position 570, AAR06948 position 447, AAR06947 position 447, AAR06946 position 447, AAR06945 position 447, AAR06944 position 447, AAR06943 position 447, AAR06942 position 447, AAR06941 position 447, AAR06940 position 447, AAR06939 position 447, AAR06938 position 447, AAR06937 position 447, AAR06936 position 447, AAR06935 position 447, AAR06934 position 447, AAR06933 position 447, AAR06932 position 447, AAR06931 position 447, AAO00999 position 570, AAO00998 position 570, AAP22087 position 570, AAP22086 position 570, AAP22089 position 570.

2004
AAT11593 position 280, AAT11552 position 280, AAT11551 position 280, AAT11550 position 280, AAT11549 position 280, AAT11548 position 280, AAT11547 position 280, AAT11546 position 280, -continued AAT11545 position 280, AAT11544 position 280,
AAT11543 position 280, AAT11542 position 280,
AAT11541 position 280, AAT11540 position 280,
AAT11539 position 280, AAT11538 position 280,
AAT11537 position 280, AAT11536 position 280,
AAT11535 position 280, AAT11534 position 280,
AAS75296 position 123, AAS75295 position 123,
AAS75294 position 123, AAS75293 position 123,
AAS75292 position 123, AAS75291 position 123,
AAT95390 position 570, AAU00153 position 570,
AAV54504 position 570, AAT02759 position 566,
ABG67747 position 570, ABG67746 position 570,
BAD34491 position 570, BAD34490 position 570,
BAD34489 position 570, BAD34488 position 570,
ABV82765 position 570, AAZ91684 position 570,
AAW56064 position 570, AAW56066 position 570,
AAW56065 position 570, AAW28871 position 570,
AXT92099 position 570, AAT92098 position 570,
AAV52690 position 570, AAV52689 position 570,
AAV52688 position 570, AAV52687 position 570,
AAV68177 position 570, AAX09982 position 570.

2005
YP_001527880 position 280, ABC40712 position 570,
YP_001527877 position 570, ABB01533 position 570,
ABA62343 position 570, AAY32590 position 447,
AAY32589 position 447, AAY55949 position 570,
AAZ32750 position 570, AAZ32749 position 570,
AAZ32748 position 570, AAZ32747 position 570,
AAZ32746 position 570, AAZ32745 position 570,
AAZ32744 position 570, AAZ32743 position 570,
AAZ32742 position 570, AAZ32741 position 570,
AAZ32740 position 570, AAZ32739 position 570,
AAZ32738 position 570, AAZ32737 position 570,
AAZ32736 position 570, AAZ32735 position 570,
AAZ32734 position 570, AAZ32733 position 570,
AAZ32732 position 570, AAZ32731 position 570,
AAZ32730 position 570, AAZ32729 position 570,
ABC49716 position 566, ABA43046 position 570,
ABA43045 position 447, ABA43044 position 447,
ABA43043 position 447, ABA43042 position 570,
ABA43041 position 447, ABA43040 position 447, ABA43039 position 447, ABA43038 position 570,
ABA43037 position 447, ABA43036 position 447,
ABA43035 position 447, ABA43034 position 570,
ABA43033 position 447, ABA43032 position 447,
ABA43031 position 447, ABA43030 position 570,
ABA43029 position 447, ABA43028 position 447,
ABA43027 position 447, ABA43026 position 570,
ABA43025 position 447, ABA43024 position 447,
ABA43023 position 447, ABA43022 position 570,
ABA43021 position 447, ABA43020 position 447,
ABA43019 position 447, ABA43018 position 570,
ABA43017 position 447, ABA43016 position 447,
ABA43015 position 447, ABA43014 position 570,
ABA43013 position 447, ABA43012 position 447,
ABA43011 position 447, ABA43010 position 570,
ABA43009 position 447, ABA43008 position 447,
ABA43007 position 447, ABA43006 position 570,
ABA43005 position 447, ABA43004 position 447,
ABA43003 position 447, ABA54595 position 570,
ABA54594 position 570, ABA54593 position 570,
ABA54592 position 570, ABA54591 position 570,
ABA54590 position 570, ABA54589 position 570,
ABA54588 position 570. ABA54587 position 570,
ABA54586 position 570, ABA54585 position 570,
ABA54584 position 570, ABA54583 position 570,
ABA54582 position 570, ABA54581 position 570,
ABA54580 position 570, ABA54579 position 570,
ABA54578 position 570, ABA54547 position 570,
ABA54576 position 570, ABA54575 position 570,
AAY54162 position 570.

2006
ABI81406 position 270, ABI81405 position 270,
ABI81404 position 270, ABI81403 position 270,
ABI81402 position 270, ABI81401 position 270,
ABI81400 position 270, ABI81399 position 270,
ABI81398 position 270, ABI81397 position 270,
ABI81396 position 270, ABI81395 position 270,
ABI81394 position 270, ABI81393 position 270,
ABI81392 position 270, ABI81391 position 270,
ABI81390 position 270, ABI81389 position 270,
ABI81388 position 270, ABI81387 position 270, ABI81386 position 270, ABI81385 position 270,
ABI81384 position 270, ABI81383 position 270,
ABI81382 position 270, ABI81381 position 270,
ABI81380 position 270, ABI81379 position 270,
ABI81378 position 270, ABI81377 position 270,
ABI81376 position 270, ABI81375 position 270,
ABI81374 position 270, ABI81373 position 270,
ABI81372 position 270, ABI81371 position 270,
ABI81370 position 270, ABI81369 position 270,
ABI81368 position 270, ABI81367 position 270,
ABI81366 position 270, ABI81365 position 270,
ABI81364 position 270, ABI81363 position 270,
ABI81362 position 270, ABI81361 position 270,
ABI81360 position 270, ABI81359 position 270,
ABI81358 position 270, ABI81357 position 270,
ABI81356 position 270, ABI81355 position 270,
ABI81354 position 270, ABI81353 position 270,
ABI81351 position 270, ABI81350 position 270,
ABI81349 position 270, ABI81348 position 270,
ABI81347 position 270, ABI81346 position 270,
ABI81345 position 270, ABI81344 position 270,
ABI81343 position 270, ABI81342 position 270,
ABI81341 position 270, ABI81340 position 270,
ABI81339 position 270, ABI81338 position 270,
ABI81337 position 270, ABI81336 position 270,
ABI81335 position 270, ABI81334 position 270,
ABI81333 position 270, ABI81332 position 270,
ABI81331 position 270, ABI81330 position 270,
ABI81329 position 270, ABI81328 position 270,
ABI81327 position 270, ABI81326 position 270,
ABI81325 position 270, ABI81324 position 270,
ABI81323 position 270, ABI81322 position 270,
ABI81321 position 270, ABI81320 position 270,
ABI81319 position 270, ABI81318 position 270,
ABI81317 position 270, ABI81316 position 270,
ABI81315 position 270, ABI81314 position 270,
ABI81313 position 270, ABI81312 position 270,
ABI81311 position 270, ABI81310 position 270,
ABI81309 position 270, ABI81308 position 270,
ABI81307 position 270, ABI81306 position 270,
ABI81305 position 270, ABI81304 position 270,
ABI81303 position 270, ABI81302 position 270,
ABI81301 position 270, ABI81300 position 270,
ABI81299 position 270, ABI81298 position 270,
ABI81297 position 270, ABI81296 position 270,
ABI81295 position 270, ABI81294 position 270,
ABI81293 position 270, ABI81292 position 270,
ABI81291 position 270, ABI81290 position 270,
ABI81289 position 270, ABI81288 position 270,
ABI81287 position 270, ABI81286 position 270,
ABI81285 position 270, ABI81284 position 270,
ABI81283 position 270, ABI81282 position 270,
ABI81281 position 270, ABI81280 position 270,
ABI81279 position 270, ABI81278 position 270,
ABI81277 position 270, ABI81276 position 270,
ABI81275 position 270, ABI81274 position 270,
ABI81273 position 270, ABI81272 position 270,
ABI81271 position 270, ABI81270 position 270,
ABI81269 position 270, ABI81268 position 270,
ABI81267 position 270, ABI81266 position 270,
ABI81265 position 270, ABI81264 position 270,
ABI81263 position 270, ABI81262 position 270,
ABI81261 position 270, ABI81260 position 270,
ABI81259 position 270, ABI81258 position 270,
ABI81257 position 270, ABI81256 position 270,
ABI81255 position 270, ABI81254 position 270,
ABI81253 position 270, ABI81252 position 270,
ABI81251 position 270, ABI81250 position 270,
ABI81249 position 270, ABI81248 position 270,
ABI81247 position 270, ABI81246 position 270,
ABI81245 position 270, ABI81244 position 270,
ABI81243 position 270, ABI81242 position 270,
ABI81241 position 270, ABI81240 position 270,
ABI81239 position 270, ABI81238 position 270,
ABI81237 position 270, ABI81236 position 270,
ABI81235 position 270, ABI81234 position 270,
ABI81233 position 270, ABI81232 position 270,
ABI81231 position 270, ABI81230 position 270,
ABI81229 position 270, ABI81228 position 270,
ABJ90133 position 304, ABJ90132 position 304,
ABJ90131 position 304, ABJ90130 position 304, ABJ90129 position 304, ABJ90128 position 304, ABJ90127 position 304, ABJ90126 position 304, ABJ90125 position 304, ABJ90124 position 304, ABJ90123 position 304, ABJ90122 position 304, ABJ90121 position 304, ABJ90120 position 304, ABJ90119 position 304, ABJ90118 position 304, ABJ90117 position 304, ABJ90116 position 304, ABJ90115 position 304, ABJ90114 position 304, ABJ90113 position 304, ABJ90112 position 304, ABJ90111 position 304, ABJ90110 position 304, ABJ90109 position 304, ABJ90108 position 304, ABJ90107 position 304, ABJ90106 position 304, ABJ90105 position 304, ABJ90104 position 304, ABJ90103 position 304, ABJ90102 position 304, ABJ90101 position 304, ABJ90100 position 304, ABJ90099 position 304, ABJ90098 position 304, ABJ90097 position 304, ABJ90096 position 304, ABJ90095 position 304, ABJ90094 position 304, ABJ90093 position 304, ABJ90092 position 304, ABJ90091 position 304, ABJ90090 position 304, ABJ90089 position 304, ABJ90088 position 304, ABJ90087 position 304, ABJ90086 position 304, ABJ90085 position 304, ABJ90084 position 304, ABJ90083 position 304, ABJ90082 position 304, ABJ90081 position 304, ABJ90080 position 304, ABJ90079 position 304, ABJ90078 position 304, ABJ90077 position 304, ABJ90076 position 304, ABJ90075 position 304, ABJ90074 position 304, ABJ90073 position 304, ABJ90072 position 304, ABJ90071 position 304, ABJ90070 position 304, ABJ90069 position 304, ABJ90068 position 304, ABJ90067 position 304, ABJ90066 position 304, CAL49454 position 570, ABI97486 position 570, ABG36517 position 447, ABG81344 position 570, ABG81343 position 570, ABG81342 position 570, ABG81341 position 570, ABG81340 position 570, ABG76816 position 570, ABG76815 position 570, ABG76814 position 570, ABG76813 position 570, ABG76812 position 570, ABG76811 position 570, ABG76810 position 570, ABG76809 position 570, ABG76808 position 570, ABG76807 position 570, ABG76806 position 570, ABG76805 position 570, ABG76804 position 570, ABG76803 position 570, ABG76802 position 570, ABG76801 position 570, ABG76800 position 570, ABG76799 position 570, ABG76798 position 570, ABG76797 position 570, ABG76796 position 570, ABG76795 position 570, ABI26622 position 570, ABI26621 position 570, ABD19642 position 570, ABD19641 position 570, ABD19640 position 570, ABD19513 position 570, ABD19512 position 570, ABD19511 position 570, ABD85010 position 570, ABD85083 position 570, ABD85082 position 570, ABD85081 position 570, ABD85080 position 570, ABD85078 position 570, ABD85077 position 570, ABD85076 position 570, ABD85075 position 570, ABD85074 position 570, ABD85073 position 570, ABD85072 position 570, ABD85070 position 570, ABD85069 position 570, ABD85068 position 570, ABD85067 position 570, ABD85066 position 570, ABD85065 position 570, ABD67764 position 570, ABD67762 position 570, ABD67761 position 570, ABD67760 position 570, ABD67759 position 570, ABD67758 position 570, ABD67757 position 570, ABD67756 position 570, CAM90885 position 280, CAM90884 position 280.

2007
ABR19639 position 570, ABV22897 position 570, ABU54838 position 570, ABU52997 position 570, ABQ52692 position 570, ABO69610 position 447, ABO69609 position 447, ABO69608 position 447, ABO69607 position 447, ABO69606 position 447, ABO69605 position 447, ABO69604 position 447, ABO69603 position 447, ABO69602 position 447, ABO69601 position 447, ABO69600 position 447, ABO69599 position 447, ABO69598 position 447, ABO69597 position 447, ABO69596 position 447, ABO69595 position 447, ABO69594 position 447, ABO69593 position 447, ABO69592 position 447, ABU41789 position 570, CAM91200 position 570.

-continued

2008
ABZ10682 position 280, ABZ10681 position 280,

ABZ10680 position 280, ABZ10679 position 280,

AB710678 position 280.

A "more recent arrival'- a WNV replikin which
appeared in 1998
Sequence Histony by Year
HNDKRADPAFVCK (SEQ ID NO: 202)
All occurrences of the sequence by year:
1998
AAD28624 position 346.

2000
AAG2039 position 371.

2001
AAL87748 position 346, AAL87746 position 346.

2003
AAR84614 position 371.

The sequence listing, saved as file named 47504-seqlisting.txt, created on Apr. 23, 2008, and totaling 87000 bytes, is hereby incorporated by reference in its entirety.

What is claimed is:

1. A method of increasing survival in shrimp exposed to taura syndrome virus comprising administering to at least one shrimp a substance comprising a mixture of isolated or synthetic peptides, wherein each peptide of the mixture consists of 7 to 50 amino acids and wherein the mixture includes peptides comprising at least each of the following sequences of KVGSRRYKSH (SEQ ID NO: 1), HFATKCFGEVPKK (SEQ ID NO: 2), KAENEFWDGVKQSH (SEQ ID NO: 3), KGHRKVPCEQK (SEQ ID NO: 4), HRKVPCEQK (SEQ ID NO: 5), KVPCEQKIWLH (SEQ ID NO: 6), KIWLHQNPGK (SEQ ID NO: 7), HQNPGKTQQDMK (SEQ ID NO: 8), KGNTRVHVK (SEQ ID NO: 9), KEHVEKIVDK (SEQ ID NO: 10), and HVEKIVDKAK (SEQ ID NO: 11).

2. The method of claim 1, wherein said isolated or synthetic peptides are synthetic.

3. The method of claim 1, wherein said substance comprises a mixture consisting of the isolated or synthetic peptides KVGSRRYKSH (SEQ ID NO: 1), HFATKCFGEVPKK (SEQ ID NO: 2), KAENEFWDGVKQSH (SEQ ID NO: 3), KGHRKVPCEQK (SEQ ID NO: 4), HRKVPCEQK (SEQ ID NO: 5), KVPCEQKIWLH (SEQ ID NO: 6), KIWLHQNPGK (SEQ ID NO: 7), HQNPGKTQQDMK (SEQ ID NO: 8), KGNTRVHVK (SEQ ID NO: 9), KEHVEKIVDK (SEQ ID NO: 10), and HVEKIVDKAK (SEQ ID NO: 11).

4. The method of claim 1, wherein said isolated or synthetic peptides consist of up to 15 amino acids.

5. The method of claim 1, wherein said substance further comprises a pharmaceutically acceptable carrier.

6. The method of claim 1, wherein said substance comprises feed.

7. The method of claim 6, wherein said feed comprises a daily ration of feed for shrimp.

8. The method of claim 3, wherein said substance comprises an equal mixture by weight of each of said isolated or synthetic peptides.

9. The method of claim 3, wherein said substance is administered to shrimp at a dose of about 0.01 mg to about 2 mg per gram of body weight of each shrimp per day.

10. The method of claim 9, wherein said dose is about 0.2 mg to 1.0 mg per gram of body weight of each shrimp per day.

11. The method of claim 10, wherein said dose is about 0.5 mg per gram of body weight of each shrimp per day.

12. The method of claim 1, wherein said substance is administered to shrimp as a prophylactic therapy prior to the onset of symptoms of a taura syndrome virus.

13. The method of claim 1, wherein said substance is administered to shrimp as a therapy after the onset of symptoms of taura syndrome virus.

14. The method of claim 1, wherein said substance is administered to shrimp as a prophylactic therapy at subtherapeutic concentrations.

15. The method of claim 14, wherein said substance is administered over substantially the entire life cycle of at least one shrimp.

16. The method of claim 1, wherein said substance is administered orally, via submersion of the invertebrate in an aqueous medium containing said substance, or via injection.

17. The method of claim 1, wherein said substance is administered orally.

* * * * *

SEQUENCE LISTING

<160> NUMBER OF SEQ ID NOS: 203

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Val Gly Ser Arg Arg Tyr Lys Ser His
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

His Phe Ala Thr Lys Cys Phe Gly Glu Val Pro Lys Lys
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Ala Glu Asn Glu Phe Trp Asp Gly Val Lys Gln Ser His
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Gly His Arg Lys Val Pro Cys Glu Gln Lys
1               5                   10

<210> SEQ ID NO 5
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

His Arg Lys Val Pro Cys Glu Gln Lys
1               5

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Val Pro Cys Glu Gln Lys Ile Trp Leu His
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Ile Trp Leu His Gln Asn Pro Gly Lys
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

His Gln Asn Pro Gly Lys Thr Gln Gln Asp Met Lys
1               5                   10

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Gly Asn Thr Arg Val His Val Lys
1               5

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Glu His Val Glu Lys Ile Val Asp Lys
```

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

His Val Glu Lys Ile Val Asp Lys Ala Lys
1               5                   10

<210> SEQ ID NO 12
<211> LENGTH: 29
<212> TYPE: PRT
<213> ORGANISM: Goose Influenza virus

<400> SEQUENCE: 12

Lys Lys Gly Thr Ser Tyr Pro Lys Leu Ser Lys Ser Tyr Thr Asn Asn
1               5                   10                  15

Lys Gly Lys Glu Val Leu Val Leu Trp Gly Val His His
            20                  25

<210> SEQ ID NO 13
<211> LENGTH: 29
<212> TYPE: PRT
<213> ORGANISM: Human influenza virus

<400> SEQUENCE: 13

Lys Lys Gly Ser Ser Tyr Pro Lys Leu Ser Lys Ser Tyr Val Asn Asn
1               5                   10                  15

Lys Gly Lys Glu Val Leu Val Leu Trp Gly Val His His
            20                  25

<210> SEQ ID NO 14
<211> LENGTH: 29
<212> TYPE: PRT
<213> ORGANISM: Human influenza virus

<400> SEQUENCE: 14

Lys Lys Glu Asn Ser Tyr Pro Lys Leu Ser Lys Ser Tyr Val Asn Asn
1               5                   10                  15

Lys Gly Lys Glu Val Leu Val Leu Trp Gly Val His His
            20                  25

<210> SEQ ID NO 15
<211> LENGTH: 29
<212> TYPE: PRT
<213> ORGANISM: Human influenza virus

<400> SEQUENCE: 15

Lys Lys Gly Asp Ser Tyr Pro Lys Leu Thr Asn Ser Tyr Val Asn Asn
1               5                   10                  15

Lys Gly Lys Glu Val Leu Val Leu Trp Gly Val His His
            20                  25

<210> SEQ ID NO 16
<211> LENGTH: 29
<212> TYPE: PRT
<213> ORGANISM: Human influenza virus

<400> SEQUENCE: 16

```
Lys Lys Gly Thr Ser Tyr Pro Lys Leu Ser Lys Ser Tyr Thr Asn Asn
1               5                   10                  15

Lys Gly Lys Glu Val Leu Val Leu Trp Gly Val His His
            20                  25
```

<210> SEQ ID NO 17
<211> LENGTH: 29
<212> TYPE: PRT
<213> ORGANISM: Human influenza virus

<400> SEQUENCE: 17

```
Lys Lys Gly Thr Ser Tyr Pro Lys Leu Ser Lys Ser Tyr Thr Asn Asn
1               5                   10                  15

Lys Gly Lys Glu Val Leu Val Leu Trp Gly Val His His
            20                  25
```

<210> SEQ ID NO 18
<211> LENGTH: 29
<212> TYPE: PRT
<213> ORGANISM: Human influenza virus

<400> SEQUENCE: 18

```
Lys Lys Gly Asn Ser Tyr Pro Lys Leu Ser Lys Ser Tyr Thr Asn Asn
1               5                   10                  15

Lys Gly Lys Glu Val Leu Val Ile Trp Gly Val His His
            20                  25
```

<210> SEQ ID NO 19
<211> LENGTH: 29
<212> TYPE: PRT
<213> ORGANISM: Human influenza virus

<400> SEQUENCE: 19

```
Lys Lys Gly Asn Ser Tyr Pro Lys Leu Ser Lys Ser Tyr Thr Asn Asn
1               5                   10                  15

Lys Gly Lys Glu Val Leu Val Ile Trp Gly Val His His
            20                  25
```

<210> SEQ ID NO 20
<211> LENGTH: 29
<212> TYPE: PRT
<213> ORGANISM: Human influenza virus

<400> SEQUENCE: 20

```
Lys Lys Gly Thr Ser Tyr Pro Lys Leu Ser Lys Ser Tyr Thr Asn Asn
1               5                   10                  15

Lys Gly Lys Glu Val Leu Val Leu Trp Gly Val His His
            20                  25
```

<210> SEQ ID NO 21
<211> LENGTH: 29
<212> TYPE: PRT
<213> ORGANISM: Human influenza virus

<400> SEQUENCE: 21

```
Lys Lys Gly Asn Ser Tyr Pro Lys Leu Ser Lys Ser Tyr Thr Asn Asn
1               5                   10                  15

Lys Gly Lys Glu Val Leu Val Ile Trp Gly Val His His
            20                  25
```

<210> SEQ ID NO 22

<211> LENGTH: 29
<212> TYPE: PRT
<213> ORGANISM: Human influenza virus

<400> SEQUENCE: 22

Lys Lys Gly Thr Ser Tyr Pro L

```
Lys Gly Lys Glu Val Leu Val Ile Trp Gly Val His His
        20                  25

<210> SEQ ID NO 28
<211> LENGTH: 29
<212> TYPE: PRT
<213> ORGANISM: Human influenza virus

<400> SEQUENCE: 28

Lys Lys Gly Ser Ser Tyr Pro Lys Leu Ser Lys Ser Tyr Val Asn Asn
1               5                   10                  15

Lys Gly Lys Glu Val Leu Val Leu Trp Gly Val His His
        20                  25

<210> SEQ ID NO 29
<211> LENGTH: 29
<212> TYPE: PRT
<213> ORGANISM: Human influenza virus

<400> SEQUENCE: 29

Lys Lys Gly Ser Ser Tyr Pro Lys Leu Ser Lys Ser Tyr Val Asn Asn
1               5                   10                  15

Lys Gly Lys Glu Val Leu Val Leu Trp Gly Val His His
        20                  25

<210> SEQ ID NO 30
<211> LENGTH: 29
<212> TYPE: PRT
<213> ORGANISM: Human influenza virus

<400> SEQUENCE: 30

Lys Lys Gly Asn Ser Tyr Pro Lys Leu Ser Lys Ser Tyr Thr Asn Asn
1               5                   10                  15

Lys Gly Lys Glu Val Leu Val Ile Trp Gly Val His His
        20                  25

<210> SEQ ID NO 31
<211> LENGTH: 29
<212> TYPE: PRT
<213> ORGANISM: Human influenza virus

<400> SEQUENCE: 31

Lys Lys Gly Asn Ser Tyr Pro Lys Leu Ser Lys Ser Tyr Thr Asn Asn
1               5                   10                  15

Lys Gly Lys Glu Val Leu Val Ile Trp Gly Val His His
        20                  25

<210> SEQ ID NO 32
<211> LENGTH: 29
<212> TYPE: PRT
<213> ORGANISM: Human influenza virus

<400> SEQUENCE: 32

Lys Lys Gly Asn Ser Tyr Pro Lys Leu Ser Lys Ser Tyr Thr Asn Asn
1               5                   10                  15

Lys Gly Lys Glu Val Leu Val Ile Trp Gly Val His His
        20                  25

<210> SEQ ID NO 33
<211> LENGTH: 29
<212> TYPE: PRT
<213> ORGANISM: Human influenza virus
```

```
<400> SEQUENCE: 33

Lys Lys Gly Asn Ser Tyr Pro Lys Leu Ser Lys Ser Tyr Thr Asn Asn
1               5                   10                  15

Lys Gly Lys Glu Val Leu Val Ile Trp Gly Val His His
            20                  25

<210> SEQ ID NO 34
<211> LENGTH: 29
<212> TYPE: PRT
<213> ORGANISM: Human influenza virus

<400> SEQUENCE: 34

Lys Lys Gly Asn Ser Tyr Pro Lys Ile Ser Lys Ser Tyr Ile Asn Asn
1               5                   10                  15

Lys Glu Lys Glu Val Leu Val Leu Trp Gly Ile His His
            20                  25

<210> SEQ ID NO 35
<211> LENGTH: 29
<212> TYPE: PRT
<213> ORGANISM: Human influenza virus

<400> SEQUENCE: 35

Lys Lys Gly Asn Ser Tyr Pro Lys Leu Ser Lys Ser Tyr Ile Asn Asn
1               5                   10                  15

Lys Lys Lys Glu Val Leu Val Ile Trp Gly Ile His His
            20                  25

<210> SEQ ID NO 36
<211> LENGTH: 29
<212> TYPE: PRT
<213> ORGANISM: Human influenza virus

<400> SEQUENCE: 36

Lys Lys Gly Asn Ser Tyr Pro Lys Leu Ser Lys Ser Tyr Ile Asn Asn
1               5                   10                  15

Lys Gly Lys Lys Val Leu Val Leu Trp Gly Ile His His
            20                  25

<210> SEQ ID NO 37
<211> LENGTH: 29
<212> TYPE: PRT
<213> ORGANISM: Human influenza virus

<400> SEQUENCE: 37

Lys Lys Gly Thr Ser Tyr Pro Lys Leu Ser Lys Ser Tyr Thr Asn Asn
1               5                   10                  15

Lys Lys Lys Glu Val Leu Val Leu Trp Gly Val His His
            20                  25

<210> SEQ ID NO 38
<211> LENGTH: 28
<212> TYPE: PRT
<213> ORGANISM: Human influenza virus

<400> SEQUENCE: 38

Lys Asn Gly Leu Tyr Pro Asn Leu Ser Lys Ser Tyr Ala Asn Asn Lys
1               5                   10                  15

Glu Lys Glu Val Leu Val Leu Trp Gly Val His His
            20                  25
```

```
<210> SEQ ID NO 39
<211> LENGTH: 28
<212> TYPE: PRT
<213> ORGANISM: Human influenza virus

<400> SEQUENCE: 39

Lys

-continued

```
Asn Val Glu Asp Leu Leu Ile Leu Trp Gly Ile His His
            20                  25

<210> SEQ ID NO 45
<211> LENGTH: 29
<212> TYPE: PRT
<213> ORGANISM: Human influenza virus

<400> SEQUENCE: 45

Lys Lys Asn Asn Ala Tyr Pro Thr Ile Lys Arg Ser Tyr Ser Asn Thr
1               5                   10                  15

Asn Gln Glu Asp Leu Leu Val Leu Trp Gly Ile His His
            20                  25

<210> SEQ ID NO 46
<211> LENGTH: 29
<212> TYPE: PRT
<213> ORGANISM: Human influenza virus

<400> SEQUENCE: 46

Lys Lys Asn Asn Ala Tyr Pro Thr Ile Lys Arg Thr Tyr Asn Asn Thr
1               5                   10                  15

Asn Ile Glu Asp Leu Leu Ile Leu Trp Gly Ile His His
            20                  25

<210> SEQ ID NO 47
<211> LENGTH: 29
<212> TYPE: PRT
<213> ORGANISM: Human influenza virus

<400> SEQUENCE: 47

Lys Lys Asn Asn Ala Tyr Pro Thr Ile Lys Arg Thr Tyr Asn Asn Thr
1               5                   10                  15

Asn Met Glu Asp Leu Leu Ile Leu Trp Gly Ile His His
            20                  25

<210> SEQ ID NO 48
<211> LENGTH: 29
<212> TYPE: PRT
<213> ORGANISM: Human influenza virus

<400> SEQUENCE: 48

Lys Lys Gly Asn Ala Tyr Pro Thr Ile Lys Arg Thr Tyr Asn Asn Thr
1               5                   10                  15

Asn Val Glu Asp Leu Leu Ile Leu Trp Gly Ile His His
            20                  25

<210> SEQ ID NO 49
<211> LENGTH: 29
<212> TYPE: PRT
<213> ORGANISM: Human influenza virus

<400> SEQUENCE: 49

Lys Lys Asn Asn Thr Tyr Pro Thr Ile Lys Arg Ser Tyr Asn Asn Thr
1               5                   10                  15

Asn Gln Glu Asp Leu Leu Ile Leu Trp Gly Ile His His
            20                  25

<210> SEQ ID NO 50
<211> LENGTH: 29
<212> TYPE: PRT
<213> ORGANISM: Human influenza virus
```

<400> SEQUENCE: 50

Lys Lys Asn Ser Ala Tyr Pro Thr Ile Lys Arg Ser Tyr Asn Asn Thr
1               5                   10                  15

Asn Gln Glu Asp Leu Leu Val Leu Trp Gly Ile His His
            20                  25

<210> SEQ ID NO 51
<211> LENGTH: 29
<212> TYPE: PRT
<213> ORGANISM: Human influenza virus

<400> SEQUENCE: 51

Lys Lys Asn Ser Ala Tyr Pro Thr Ile Lys Arg Ser Tyr Asn Asn Thr
1               5                   10                  15

Asn Gln Glu Asp Leu Leu Val Leu Trp Gly Ile His His
            20                  25

<210> SEQ ID NO 52
<211> LENGTH: 29
<212> TYPE: PRT
<213> ORGANISM: Human influenza virus

<400> SEQUENCE: 52

Lys Lys Asn Ser Ala Tyr Pro Thr Ile Lys Arg Ser Tyr Asn Asn Thr
1               5                   10                  15

Asn Gln Glu Asp Leu Leu Val Leu Trp Gly Ile His His
            20                  25

<210> SEQ ID NO 53
<211> LENGTH: 29
<212> TYPE: PRT
<213> ORGANISM: Human influenza virus

<400> SEQUENCE: 53

Lys Lys Asn Ser Ala Tyr Pro Thr Ile Lys Arg Ser Tyr Asn Asn Thr
1               5                   10                  15

Asn Gln Glu Asp Leu Leu Val Leu Trp Gly Ile His His
            20                  25

<210> SEQ ID NO 54
<211> LENGTH: 29
<212> TYPE: PRT
<213> ORGANISM: Human influenza virus

<400> SEQUENCE: 54

Lys Lys Asn Ser Ala Tyr Pro Thr Ile Lys Arg Ser Tyr Asn Asn Thr
1               5                   10                  15

Asn Gln Glu Asp Leu Leu Val Leu Trp Gly Ile His His
            20                  25

<210> SEQ ID NO 55
<211> LENGTH: 29
<212> TYPE: PRT
<213> ORGANISM: Human influenza virus

<400> SEQUENCE: 55

Lys Lys Asn Ser Ala Tyr Pro Thr Ile Lys Arg Ser Tyr Asn Asn Thr
1               5                   10                  15

Asn Gln Glu Asp Leu Leu Val Leu Trp Gly Ile His His
            20                  25

```
<210> SEQ ID NO 56
<211> LENGTH: 29
<212> TYPE: PRT
<213> ORGANISM: Human influenza virus

<400> SEQUENCE: 56

Lys Lys Asn Asn Ala Tyr Pro Thr Ile Lys Arg Ser Tyr Asn Asn Thr
1               5                   10                  15

Asn Gln Glu Asp Leu Leu Val Leu Trp Gly Ile His His
            20                  25

<210> SEQ ID NO 57
<211> LENGTH: 29
<212> TYPE: PRT
<213> ORGANISM: Human influenza virus

<400> SEQUENCE: 57

Lys Lys Asn Ser Ala Tyr Pro Thr Ile Lys Arg Ser Tyr Asn Asn Thr
1               5                   10                  15

Asn Gln Glu Asp Leu Leu Val Leu Trp Gly Ile His His
            20                  25

<210> SEQ ID NO 58
<211> LENGTH: 29
<212> TYPE: PRT
<213> ORGANISM: Human influenza virus

<400> SEQUENCE: 58

Lys Lys Asn Ser Thr Tyr Pro Thr Ile Lys Arg Ser Tyr Asn Asn Thr
1               5                   10                  15

Asn Gln Glu Asp Leu Leu Val Leu Trp Gly Ile His His
            20                  25

<210> SEQ ID NO 59
<211> LENGTH: 29
<212> TYPE: PRT
<213> ORGANISM: Human influenza virus

<400> SEQUENCE: 59

Lys Lys Asn Ser Thr Tyr Pro Thr Ile Lys Arg Ser Tyr Asn Asn Thr
1               5                   10                  15

Asn Gln Glu Asp Leu Leu Val Leu Trp Gly Ile His His
            20                  25

<210> SEQ ID NO 60
<211> LENGTH: 29
<212> TYPE: PRT
<213> ORGANISM: Human influenza virus

<400> SEQUENCE: 60

Lys Lys Asn Ser Thr Tyr Pro Thr Ile Lys Arg Ser Tyr Asn Asn Thr
1               5                   10                  15

Asn Gln Glu Asp Leu Leu Val Leu Trp Gly Ile His His
            20                  25

<210> SEQ ID NO 61
<211> LENGTH: 29
<212> TYPE: PRT
<213> ORGANISM: Human influenza virus

<400> SEQUENCE: 61

Lys Lys Asn Ser Thr Tyr Pro Thr Ile Lys Arg Ser Tyr Asn Asn Thr
1               5                   10                  15
```

```
Asn Gln Glu Asp Leu Leu Val Leu Trp Gly Ile His His
            20                  25
```

<210> SEQ ID NO 62
<211> LENGTH: 29
<212> TYPE: PRT
<213> ORGANISM: Human influenza virus

<400> SEQUENCE: 62

```
Lys Lys Asn Ser Thr Tyr Pro Thr Ile Lys Arg Ser Tyr Asn Asn Thr
1               5                   10                  15

Asn Gln Glu Asp Leu Leu Val Leu Trp Gly Ile His His
            20                  25
```

<210> SEQ ID NO 63
<211> LENGTH: 29
<212> TYPE: PRT
<213> ORGANISM: Human influenza virus

<400> SEQUENCE: 63

```
Lys Lys Asn Asn Ala Tyr Pro Thr Ile Lys Arg Ser Tyr Asn Asn Thr
1               5                   10                  15

Asn Gln Glu Asp Leu Leu Val Leu Trp Gly Ile His His
            20                  25
```

<210> SEQ ID NO 64
<211> LENGTH: 29
<212> TYPE: PRT
<213> ORGANISM: Human influenza virus

<400> SEQUENCE: 64

```
Lys Lys Asn Ser Thr Tyr Pro Thr Ile Lys Arg Ser Tyr Asn Asn Thr
1               5                   10                  15

Asn Gln Glu Asp Leu Leu Val Met Trp Gly Ile His His
            20                  25
```

<210> SEQ ID NO 65
<211> LENGTH: 29
<212> TYPE: PRT
<213> ORGANISM: Human influenza virus

<400> SEQUENCE: 65

```
Lys Lys Asn Ser Ala Tyr Pro Thr Ile Lys Arg Ser Tyr Asn Asn Thr
1               5                   10                  15

Asn Gln Glu Asp Leu Leu Val Leu Trp Gly Ile His His
            20                  25
```

<210> SEQ ID NO 66
<211> LENGTH: 29
<212> TYPE: PRT
<213> ORGANISM: Human influenza virus

<400> SEQUENCE: 66

```
Lys Lys Asn Ser Thr Tyr Pro Thr Ile Lys Arg Ser Tyr Asn Asn Thr
1               5                   10                  15

Asn Gln Glu Asp Leu Leu Val Leu Trp Gly Ile His His
            20                  25
```

<210> SEQ ID NO 67
<211> LENGTH: 29
<212> TYPE: PRT
<213> ORGANISM: Human influenza virus

<400> SEQUENCE: 67

Lys Lys Asn Ser Thr Tyr Pro Thr Ile Lys Arg Ser Tyr Asn Asn Thr
1               5                   10                  15

Asn Gln Glu Asp Leu Leu Val Leu Trp Gly Ile His His
            20                  25

<210> SEQ ID NO 68
<211> LENGTH: 29
<212> TYPE: PRT
<213> ORGANISM: Human influenza virus

<400> SEQUENCE: 68

Lys Lys Asn Ser Thr Tyr Pro Thr Ile Lys Arg Ser Tyr Asn Asn Thr
1               5                   10                  15

Asn Gln Glu Asp Leu Leu Val Leu Trp Gly Ile Gln His
            20                  25

<210> SEQ ID NO 69
<211> LENGTH: 29
<212> TYPE: PRT
<213> ORGANISM: Human influenza virus

<400> SEQUENCE: 69

Lys Lys Asn Ser Ala Tyr Pro Ile Ile Lys Arg Ser Tyr Asn Asn Thr
1               5                   10                  15

Asn Gln Glu Asp Leu Leu Val Leu Trp Gly Ile His His
            20                  25

<210> SEQ ID NO 70
<211> LENGTH: 29
<212> TYPE: PRT
<213> ORGANISM: Goose influenza virus
<220> FEATURE:
<221> NAME/KEY: MOD_RES
<222> LOCATION: (13)..(13)
<223> OTHER INFORMATION: Any amino acid

<400> SEQUENCE: 70

Lys Lys Asn Ser Ala Tyr Pro Thr Ile Lys Arg Ser Xaa Asn Asn Thr
1               5                   10                  15

Asn His Glu Asp Leu Leu Val Leu Trp Gly Ile His His
            20                  25

<210> SEQ ID NO 71
<211> LENGTH: 29
<212> TYPE: PRT
<213> ORGANISM: Human influenza virus

<400> SEQUENCE: 71

Lys Lys Asn Ser Ala Tyr Pro Thr Ile Lys Arg Ser Tyr Asn Asn Thr
1               5                   10                  15

Asn Gln Glu Asp Leu Leu Val Leu Trp Gly Ile His His
            20                  25

<210> SEQ ID NO 72
<211> LENGTH: 29
<212> TYPE: PRT
<213> ORGANISM: Human influenza virus

<400> SEQUENCE: 72

Lys Lys Asn Asn Ala Tyr Pro Thr Ile Lys Arg Ser Tyr Asn Asn Thr
1               5                   10                  15

```
Asn Gln Glu Asp Leu Leu Val Leu Trp Gly Ile His His
            20                  25
```

<210> SEQ ID NO 73
<211> LENGTH: 29
<212> TYPE: PRT
<213> ORGANISM: Human influenza virus

<400> SEQUENCE: 73

```
Lys Lys Asn Asn Thr Tyr Pro Thr Ile Lys Ser Tyr Asn Asn Thr
1               5                   10                  15

Asn Gln Glu Asp Leu Leu Val Leu Trp Gly Ile His His
            20                  25
```

<210> SEQ ID NO 74
<211> LENGTH: 29
<212> TYPE: PRT
<213> ORGANISM: Human influenza virus

<400> SEQUENCE: 74

```
Lys Lys Asn Ser Thr Tyr Pro Thr Ile Lys Arg Ser Tyr Asn Asn Thr
1               5                   10                  15

Asn Gln Glu Asp Leu Leu Val Ile Trp Gly Ile His His
            20                  25
```

<210> SEQ ID NO 75
<211> LENGTH: 5
<212> TYPE: PRT
<213> ORGANISM: Human influenza virus

<400> SEQUENCE: 75

```
Leu Val Leu Trp Gly
1               5
```

<210> SEQ ID NO 76
<211> LENGTH: 29
<212> TYPE: PRT
<213> ORGANISM: Goose influenza virus

<400> SEQUENCE: 76

```
Lys Lys Gly Thr Ser Tyr Pro Lys Leu Ser Lys Ser Tyr Thr Asn Asn
1               5                   10                  15

Lys Gly Lys Glu Val Leu Val Leu Trp Gly Val His His
            20                  25
```

<210> SEQ ID NO 77
<211> LENGTH: 29
<212> TYPE: PRT
<213> ORGANISM: Pig influenza virus

<400> SEQUENCE: 77

```
Lys Lys Gly Asn Ser Tyr Pro Lys Leu Ser Lys Ser Tyr Thr Asn Asn
1               5                   10                  15

Lys Gly Lys Glu Val Leu Val Ile Trp Gly Val His His
            20                  25
```

<210> SEQ ID NO 78
<211> LENGTH: 29
<212> TYPE: PRT
<213> ORGANISM: Shrimp white spot virus

<400> SEQUENCE: 78

```
Lys Lys Asn Val Lys Ser Ala Lys Gln Leu Pro His Leu Lys Val Leu
1               5                   10                  15

Lys Lys Leu Asp Val Arg Gly Ala Lys Gln Leu Pro His
            20                  25
```

<210> SEQ ID NO 79
<211> LENGTH: 28
<212> TYPE: PRT
<213> ORGANISM: Shrimp white spot virus

<400> SEQUENCE: 79

```
Lys Val His Leu Asp Val Lys Gly Val Lys Gln Leu Leu His Leu Lys
1               5                   10                  15

Val Arg Leu Asp Val Arg Gly Ala Lys Gln Leu His
            20                  25
```

<210> SEQ ID NO 80
<211> LENGTH: 29
<212> TYPE: PRT
<213> ORGANISM: Human influenza virus

<400> SEQUENCE: 80

```
Lys Lys Glu Asn Ser Tyr Pro Lys Leu Arg Lys Ser Ile Ile Ile Asn
1               5                   10                  15

Lys Lys Glu Val Lys Leu Val Ile Trp Gly Ile His His
            20                  25
```

<210> SEQ ID NO 81
<211> LENGTH: 19
<212> TYPE: PRT
<213> ORGANISM: Human influenza virus

<400> SEQUENCE: 81

```
Lys Ser Tyr Lys Asn Thr Arg Lys Asp Pro Ala Leu Ile Ile Trp Gly
1               5                   10                  15

Ile His His
```

<210> SEQ ID NO 82
<211> LENGTH: 29
<212> TYPE: PRT
<213> ORGANISM: Human influenza virus

<400> SEQUENCE: 82

```
Lys Lys Gly Pro Asn Tyr Pro Val Ala Lys Arg Ser Tyr Asn Asn Thr
1               5                   10                  15

Ser Gly Glu Gln Met Leu Ile Ile Trp Gly Val His His
            20                  25
```

<210> SEQ ID NO 83
<211> LENGTH: 29
<212> TYPE: PRT
<213> ORGANISM: Human influenza virus

<400> SEQUENCE: 83

```
Lys Lys Gly Pro Asn Tyr Pro Val Ala Lys Arg Ser Tyr Asn Asn Thr
1               5                   10                  15

Ser Gly Glu Gln Met Leu Ile Ile Trp Gly Ile His His
            20                  25
```

<210> SEQ ID NO 84
<211> LENGTH: 29
<212> TYPE: PRT

```
<213> ORGANISM: Human influenza virus

<400> SEQUENCE: 84

Lys Lys Asn Asn Ala Tyr Pro Thr Ile L

<400> SEQUENCE: 89

His Phe Ala Thr Lys Cys Phe Gly Glu Val Pro Lys Lys Lys Lys
1               5                   10                  15
Lys Lys His Lys
            20

<210> SEQ ID NO 90
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Lys Ala Glu Asn Glu Phe Trp Asp Gly Val Lys Gln Ser His Lys Lys
1               5                   10                  15
Lys Lys Lys His Lys
            20

<210> SEQ ID NO 91
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Lys Gly His Arg Lys Val Pro Cys Glu Gln Lys Lys Lys Lys Lys Lys
1               5                   10                  15
His Lys

<210> SEQ ID NO 92
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

His Arg Lys Val Pro Cys Glu Gln Lys Lys Lys Lys Lys Lys His Lys
1               5                   10                  15

<210> SEQ ID NO 93
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Lys Val Pro Cys Glu Gln Lys Ile Trp Leu His Lys Lys Lys Lys Lys
1               5                   10                  15
His Lys

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 94

Lys Ile Trp Leu His Gln Asn Pro Gly Lys Lys Lys Lys Lys His
1               5                   10                  15

Lys

<210> SEQ ID NO 95
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

His Gln Asn Pro Gly Lys Thr Gln Gln Asp Met Lys Lys Lys Lys
1               5                   10                  15

Lys His Lys

<210> SEQ ID NO 96
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Lys Gly Asn Thr Arg Val His Val Lys Lys Lys Lys Lys His Lys
1               5                   10                  15

<210> SEQ ID NO 97
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Lys Glu His Val Glu Lys Ile Val Asp Lys Lys Lys Lys Lys His
1               5                   10                  15

Lys

<210> SEQ ID NO 98
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

His Val Glu Lys Ile Val Asp Lys Ala Lys Lys Lys Lys Lys His
1               5                   10                  15

Lys

<210> SEQ ID NO 99
<211> LENGTH: 29
<212> TYPE: PRT
<213> ORGANISM: Human influenza virus

<400> SEQUENCE: 99

Lys Lys Gly Ser Ser Tyr Pro Lys Leu Ser Lys Ser Tyr Val Asn Asn
```

-continued 1 5 10 15

Lys Gly Lys Glu Val Leu Val Leu Trp Gly Val His His
20 25

<210> SEQ ID NO 100
<211> LENGTH: 28
<212> TYPE: PRT
<213> ORGANISM: Human influenza virus

<400> SEQUENCE: 100

Lys Gly Ser Ser Tyr Pro Lys Leu Ser Lys Ser Tyr Val Asn Asn Lys
1 5 10 15

Gly Lys Glu Val Leu Val Leu Trp Gly Val His His
20 25

<210> SEQ ID NO 101
<211> LENGTH: 28
<212> TYPE: PRT
<213> ORGANISM: Shrimp White spot virus

<400> SEQUENCE: 101

Lys Val His Leu Asp Val Lys Gly Val Lys Gln Leu Leu His Leu Lys
1 5 10 15

Val Arg Leu Asp Val Arg Gly Ala Lys Gln Leu His
20 25

<210> SEQ ID NO 102
<211> LENGTH: 29
<212> TYPE: PRT
<213> ORGANISM: Shrimp White spot virus

<400> SEQUENCE: 102

Lys Lys Asn Val Lys Ser Ala Lys Gln Leu Pro His Leu Lys Val Leu
1 5 10 15

Lys Lys Leu Asp Val Arg Gly Ala Lys Gln Leu Pro His
20 25

<210> SEQ ID NO 103
<211> LENGTH: 32
<212> TYPE: PRT
<213> ORGANISM: Taura syndrome virus

<400> SEQUENCE: 103

Lys Lys Val Gln Ala Asn Lys Thr Arg Val Phe Ala Ala Ser Asn Gln
1 5 10 15

Gly Leu Ala Leu Ala Leu Arg Arg Tyr Tyr Leu Ser Phe Leu Asp His
20 25 30

<210> SEQ ID NO 104
<211> LENGTH: 33
<212> TYPE: PRT
<213> ORGANISM: Taura syndrome virus

<400> SEQUENCE: 104

Lys Lys Ala Cys Arg Asn Ala Gly Tyr Lys Glu Ala Cys Leu His Glu
1 5 10 15

Leu Asp Cys Lys Ser Phe Leu Leu Ala Gln Gln Gly Arg Ala Gly Ala
20 25 30

His

<210> SEQ ID NO 105

<211> LENGTH: 1011
<212> TYPE: PRT
<213> ORGANISM: Taura syndrome virus

<400> SEQUENCE: 105

```
Met Pro Ala Asn Pro Val Glu Ile Asp Asn Phe Asp Thr Thr Thr Ser
1               5                   10                  15

Gly Gly Leu Ile Pro Gly Gly Ser Val Thr Asn Ser Glu Gly Ser Thr
            20                  25                  30

Ile Leu Met Asn Asp Ile Pro Ile Thr Asn Gln Asn Val Leu Ser
        35                  40                  45

Lys Asn Val Thr Asp Asn Leu Phe Glu Val Gln Asp Gln Ala Leu Ile
50                  55                  60

Glu Ser Leu Ser Arg Asp Val Leu Leu His Asn Asp Ser Trp Thr Ser
65                  70                  75                  80

Ser Asp Asp Glu Ile Gly Thr Thr Met Thr Gln Glu Gln Leu Ala Thr
                85                  90                  95

Glu Phe Asn Gln Pro His Leu Tyr Glu Ile Ser Leu Pro Asp Asp Ile
            100                 105                 110

Val Arg Lys Ser Leu Phe Met Ser Asn Lys Leu Ala Asn Ile Ala Tyr
        115                 120                 125

Met Arg Cys Asp Tyr Glu Val Thr Val Arg Val Gln Ala Thr Pro Phe
130                 135                 140

Leu Gln Gly Ala Leu Trp Leu Trp Asn Lys Met Asn Ala Lys Gln Thr
145                 150                 155                 160

Ser Ile Ile Arg Arg Thr Leu Thr Glu His Leu Arg Ser Ile Thr Ser
                165                 170                 175

Phe Pro Gly Ile Glu Met Asn Leu Gln Ser Glu Ala Arg Ala Ile Thr
            180                 185                 190

Leu Ser Ile Pro Tyr Thr Ser Glu Phe Gln Val Phe Asn Pro Arg Asn
        195                 200                 205

Val Asn Asn Leu Asn Ser Ile Arg Leu Ser Val Leu Ser Gln Leu Gln
210                 215                 220

Gly Pro Glu Asp Val Glu Ser Ala Ser Tyr Ser Ile Tyr Gly Arg Leu
225                 230                 235                 240

Lys Asn Ile Lys Leu Tyr Gly His Ala Pro Ser Val Thr Ser Ser Val
                245                 250                 255

Tyr Pro Ser Thr Gln Ser Gly Tyr Asp Asp Cys Pro Ile Val His
            260                 265                 270

Ala Gly Thr Asp Glu Asp Ser Ser Lys Gln Gly Ile Val Ser Arg Val
        275                 280                 285

Ala Asp Thr Val Gly Ala Val Ala Asn Val Val Asp Gly Val Gly Val
290                 295                 300

Pro Ile Leu Ser Thr Ile Ala Lys Pro Val Ser Trp Val Ser Gly Val
305                 310                 315                 320

Val Ser Asn Val Ala Ser Met Phe Gly Phe Ser Lys Asp Arg Asp Met
                325                 330                 335

Thr Lys Val Asn Ala Tyr Glu Asn Leu Pro Gly Lys Gly Phe Thr His
            340                 345                 350

Gly Val Gly Phe Asp Tyr Gly Val Pro Leu Ser Leu Phe Pro Asn Asn
        355                 360                 365

Ala Ile Asp Pro Thr Ile Ala Val Pro Glu Gly Leu Asp Glu Met Ser
370                 375                 380

Ile Glu Tyr Leu Ala Gln Arg Pro Tyr Met Leu Asn Arg Tyr Thr Ile
```

-continued

```
            385                 390                 395                 400
        Arg Gly Gly Asp Thr Pro Asp Val His Gly Thr Ile Val Ala Asp Ile
                        405                 410                 415

Pro Val Ser Pro Val Asn Phe Ser Leu Tyr Gly Lys Val Ile Ala Lys
                        420                 425                 430

Tyr Arg Thr Leu Phe Ala Ala Pro Val Ser Leu Ala Val Ala Met Ala
                        435                 440                 445

Asn Trp Trp Arg Gly Asn Ile Asn Leu Asn Leu Arg Phe Ala Lys Thr
                    450                 455                 460

Gln Tyr His Gln Cys Arg Leu Leu Val Gln Tyr Leu Pro Tyr Gly Ser
        465                 470                 475                 480

Gly Val Gln Pro Ile Glu Ser Ile Leu Ser Gln Ile Ile Asp Ile Ser
                                485                 490                 495

Gln Val Asp Asp Lys Gly Ile Asp Ile Ala Phe Pro Ser Val Tyr Pro
                        500                 505                 510

Asn Lys Trp Met Arg Val Tyr Asp Pro Ala Lys Val Gly Tyr Thr Ala
                        515                 520                 525

Asp Cys Ala Pro Gly Arg Ile Val Ile Ser Val Leu Asn Pro Leu Ile
                    530                 535                 540

Ser Ala Ser Thr Val Ser Pro Asn Ile Val Met Tyr Pro Trp Val His
        545                 550                 555                 560

Trp Ser Asn Leu Glu Val Ala Glu Pro Gly Thr Leu Ala Lys Ala Ala
                        565                 570                 575

Ile Gly Phe Asn Tyr Pro Ala Asp Val Pro Glu Glu Pro Thr Phe Ser
                        580                 585                 590

Val Thr Arg Ala Pro Val Ser Gly Thr Leu Phe Thr Leu Leu Gln Asp
                        595                 600                 605

Thr Lys Val Ser Leu Gly Glu Ala Asp Gly Val Phe Ser Leu Tyr Phe
                    610                 615                 620

Thr Asn Thr Thr Thr Gly Arg Arg His Arg Leu Thr Tyr Ala Gly Leu
        625                 630                 635                 640

Pro Gly Glu Leu Gly Ser Cys Glu Ile Val Lys Leu Pro Gln Gly Gln
                        645                 650                 655

Tyr Ser Ile Glu Tyr Ala Ala Thr Ser Ala Pro Thr Leu Val Leu Asp
                        660                 665                 670

Arg Pro Ile Phe Ser Glu Pro Ile Gly Pro Lys Tyr Val Val Thr Lys
                        675                 680                 685

Val Lys Asn Gly Asp Val Val Ser Ile Ser Glu Glu Thr Leu Val Thr
                    690                 695                 700

Cys Gly Ser Met Ala Ala Leu Gly Gly Ala Thr Val Ala Leu Gln Ser
        705                 710                 715                 720

Val Asp Glu Thr Ile Glu Ile Leu Lys Leu Glu Ser Asp Phe Glu Ser
                        725                 730                 735

Lys Ala Pro Val Lys Phe Thr Pro Gly Asn Tyr Thr Val Thr Glu
                        740                 745                 750

Ala Ser Asp Val Glu Leu Val Thr Asn Gln Asp Ile Thr Val Asn Glu
                        755                 760                 765

His Asn Pro Arg Thr His Ala Gly Ile Asp Glu Pro Pro Val Lys
                    770                 775                 780

Arg Ser Val Ile Gly Arg Ile Arg Arg Val Ala Arg Tyr Val Pro
        785                 790                 795                 800

Asn Lys Leu Ile Arg Arg Ile Leu Arg Asp Leu Ser Gln Ser Pro Cys
                        805                 810                 815
```

Ile Tyr Pro Ser Thr His Ala Gly Leu Asp Tyr Ser Ser Asp Thr
            820                 825                 830

Ser Thr Met Leu Thr Thr Met Gly Glu Gln Phe Val Ser Leu Arg Met
            835                 840                 845

Leu Thr Arg Arg Ser Ser Pro Val Asp Ile Leu Arg Gly Asp Leu Val
        850                 855                 860

Thr Leu Pro Gly Ile Ser Phe Gly Thr Asp Asn Ser Leu Arg Gln Ser
865                 870                 875                 880

Leu Val Asn Ile Ile Ser Tyr Met Tyr Arg Phe Thr His Gly Ser Ile
            885                 890                 895

Ser Tyr Lys Ile Ile Pro Lys Asn Lys Gly Asp Leu Tyr Ile Thr Thr
            900                 905                 910

Thr Ser Pro Asp Ser Ile Glu Thr Ser Thr Ser Ala Tyr Gln Phe Asp
            915                 920                 925

Thr Asn Arg Ala Met His Tyr Ile Asn Thr Ser Leu Asn Pro Met Ala
        930                 935                 940

Gln Ile Ser Leu Pro Tyr Tyr Ser Pro Ala Glu Asn Leu Val Ile Asp
945                 950                 955                 960

Ser Lys Ser Phe Pro Gln Leu Ser Asp Leu Ser Ile Ser Asn Leu Glu
            965                 970                 975

Arg Thr Glu Asn Glu Tyr Phe Val Leu Ala Ser Ala Gly Asp His
            980                 985                 990

Thr Phe Ser Gln Leu Ala Gly Cys Pro Ala Phe Thr Phe Gly Pro Ala
        995                 1000                1005

Glu Leu Ala
    1010

<210> SEQ ID NO 106
<211> LENGTH: 21
<212> TYPE: PRT
<213> ORGANISM: Taura syndrome virus

<400> SEQUENCE: 106

His Leu Tyr Glu Ile Ser Leu Pro Asp Asp Ile Val Arg Lys Ser Leu
1               5                   10                  15

Phe Met Ser Asn Lys
            20

<210> SEQ ID NO 107
<211> LENGTH: 21
<212> TYPE: PRT
<213> ORGANISM: Taura syndrome virus

<400> SEQUENCE: 107

Lys Asp Arg Asp Met Thr Lys Val Asn Ala Tyr Glu Asn Leu Pro Gly
1               5                   10                  15

Lys Gly Phe Thr His
            20

<210> SEQ ID NO 108
<211> LENGTH: 15
<212> TYPE: PRT
<213> ORGANISM: Taura syndrome virus

<400> SEQUENCE: 108

Lys Val Asn Ala Tyr Glu Asn Leu Pro Gly Lys Gly Phe Thr His
1               5                   10                  15

<210> SEQ ID NO 109
<211> LENGTH: 46
<212> TYPE: PRT
<213> ORGANISM: Taura syndrome virus

<400> SEQUENCE: 109

Lys Leu Glu Ser Asp Phe Glu Ser Lys Ala Pro Val Lys Phe Thr Pro
1               5                   10                  15

Gly Asn Tyr Thr Val Val Thr Glu Ala Ser Asp Val Glu Leu Val Thr
            20                  25                  30

Asn Gln Asp Ile Thr Val Asn Glu His Asn Pro Arg Thr His
        35                  40                  45

<210> SEQ ID NO 110
<211> LENGTH: 41
<212> TYPE: PRT
<213> ORGANISM: Taura syndrome virus

<400> SEQUENCE: 110

Lys Leu Glu Ser Asp Phe Glu Ser Lys Ala Pro Val Lys Phe Thr Pro
1               5                   10                  15

Gly Asn Tyr Thr Val Val Thr Glu Ala Ser Asp Val Glu Leu Val Thr
            20                  25                  30

Asn Gln Asp Ile Thr Val Asn Glu His
        35                  40

<210> SEQ ID NO 111
<211> LENGTH: 13
<212> TYPE: PRT
<213> ORGANISM: Taura syndrome virus

<400> SEQUENCE: 111

His Gly Ser Ile Ser Tyr Lys Ile Ile Pro Lys Asn Lys
1               5                   10

<210> SEQ ID NO 112
<211> LENGTH: 36
<212> TYPE: PRT
<213> ORGANISM: Taura syndrome virus

<400> SEQUENCE: 112

Lys Ile Ile Pro Lys Asn Lys Gly Asp Leu Tyr Ile Thr Thr Thr Ser
1               5                   10                  15

Pro Asp Ser Ile Glu Thr Ser Thr Ser Ala Tyr Gln Phe Asp Thr Asn
            20                  25                  30

Arg Ala Met His
        35

<210> SEQ ID NO 113
<211> LENGTH: 2107
<212> TYPE: PRT
<213> ORGANISM: Taura syndrome virus

<400> SEQUENCE: 113

Met Ala Ser Tyr Tyr Leu Asn Ile Lys Thr His Asn Leu Arg Arg Thr
1               5                   10                  15

Pro Gly Ala His Arg Ala Phe Tyr Val Met Asn Asp Asp Gly Glu Asn
            20                  25                  30

Arg Ile Tyr Ser Leu Ile Gly Thr Leu Arg Arg Ala Pro Ala Phe Lys
        35                  40                  45

Val Gly Ser Arg Arg Tyr Lys Ser His Ile Pro Tyr Arg Arg Lys Ala
 50                  55                  60

Thr Val Ala Glu Leu Cys Asn Gln Leu His Asp Arg Val Leu Pro Phe
 65                  70                  75                  80

Ala Asn Pro Gln Val Trp Lys Glu Val Ile Ser Glu Asn Lys Val Gln
                 85                  90                  95

Pro Asp Ser Met Leu Lys Ala Ala Phe Gly Asn Trp Glu Glu Trp Pro
             100                 105                 110

Lys Asp Lys Val Cys Glu Glu Leu Tyr Ser Glu Cys Cys Gly Tyr
             115                 120                 125

Val Gly Thr Cys Tyr Val Ser Val Asp Trp Leu Arg Pro Gln Ala Thr
130                 135                 140

Lys Cys Asn Asp Cys Ile Leu Lys Met Asn Arg Asn Val Glu Tyr Pro
145                 150                 155                 160

Tyr His Thr Ile Gly Val Ser Gly Asn Val Val Thr Asn Thr Asp Ile
                 165                 170                 175

Val Tyr Thr Gly Tyr Ala Asp Val Phe Lys Cys Glu Lys Cys Asp Leu
             180                 185                 190

Leu Met Gly Ala Trp Ala Pro Asn Asp Ile Pro Ala Leu Thr His Asn
             195                 200                 205

Ile Arg Ser Ser Gln Cys Val Gln Phe Lys Leu Pro Thr Glu Asn Leu
210                 215                 220

Ala Ala Arg Asn Tyr Val Leu Leu Cys Glu Glu Ile Glu Arg Glu Asn
225                 230                 235                 240

Ile Pro Val Ile Phe Gln Asp Tyr Ser Glu Gly Asn Val Phe Thr Cys
                 245                 250                 255

Arg Ile Val Ser Gly Asp Leu Thr Ala Val Gly Thr Ala Ser Asn Met
             260                 265                 270

Tyr Thr Ala Arg Asp Val Ala Ser Lys Ser Leu Leu Asp Gln Leu His
             275                 280                 285

Asn Thr Pro Asn Val His Met His Ser Leu His Ser Leu Pro Tyr Glu
290                 295                 300

Asn Phe Pro Cys Glu Ala Leu Glu Phe Ala Val Glu Gln Gly Ile Ile
305                 310                 315                 320

Pro Pro Val Thr Phe Asp Glu Val Phe Ala Asn Asp Glu Tyr Val Ile
                 325                 330                 335

Thr Ile Ser Cys Ser Leu Leu Val Val Ser Asp Val Gly Pro Thr Gln
             340                 345                 350

Ala Val Ala Arg Glu Arg Ala Lys Arg Phe Leu Lys Met Tyr Asp
             355                 360                 365

Tyr Ser Ala Ser Tyr Pro Ser Thr His Met Phe Thr Leu Ser Thr Leu
370                 375                 380

Pro Gln Arg Ser Gly Glu Thr Leu Glu Leu Ala Asn Ala Thr Leu Asn
385                 390                 395                 400

His Val Asn Asn Val Ile Asp Arg His Asp Glu Ala Ile Ser Asn Val
                 405                 410                 415

Arg Gln Asn Val Glu Val Lys Leu Thr Asp Val Ser Arg Gln Val Gly
             420                 425                 430

Ala Met Leu Pro Lys Val Glu Thr Val Ile Asp Asp Val Ser Ser Thr
             435                 440                 445

Leu Ser Ser Phe Arg Gly Val Leu Asp Lys Ile Ser Ala Trp Met Pro
450                 455                 460

Ser Ser Asn Pro Lys Ile Ile Asp Leu Ile Lys Glu Thr Phe Val Ser

-continued

```
            465                 470                 475                 480
        Leu Phe Phe Ala Ile Leu Thr Lys Ser Leu Tyr Pro Ile Ile Gln Gly
                        485                 490                 495

Ile Ser Ser Tyr Ala Leu Arg Asn Asn Leu Met Ala Asn His Leu Thr
                        500                 505                 510

Ala Leu Ser Glu Trp Leu Met Thr Leu Glu Tyr Asp Ser Pro Asp Glu
                        515                 520                 525

Glu Glu Met Pro Ser Thr His Gly Phe Met Asp Asp Leu Thr Ser Arg
                        530                 535                 540

Leu Pro Gly Leu Asn Gly Ala Lys Val Gln Ala Thr Ile Tyr Glu
        545                 550                 555                 560

Ser Ile Gly Thr Gly Leu Cys Val Ala Leu Ser Gly Ile Leu Ser Phe
                        565                 570                 575

Ile Ala Val Met Cys Leu Gly Ile Thr Asp Leu Ser Ala Val Thr Phe
                        580                 585                 590

Asn Lys Leu Leu Thr Gln Ser Ser Leu Val Gly Arg Ala Leu Val Gly
                        595                 600                 605

Val Arg Ser Phe Lys Asp Val Phe Gly Ile Trp Asp Tyr Val Asp
        610                 615                 620

Asn Gln Val Cys Glu Ile Leu Tyr Gly Lys Ser Arg Lys Asn Leu Asp
        625                 630                 635                 640

Leu Leu Lys Glu Tyr Pro Ser Leu Asp Ser Leu Leu Ser Ile Phe Asn
                        645                 650                 655

Tyr Phe His Asp Thr Val Asp Ala Asn Val Leu Ile Ser Cys Asn Arg
                        660                 665                 670

Ala Ala Cys Glu Leu Leu Val Lys Ala Asp Asn Leu Tyr Gln Gly Tyr
                        675                 680                 685

Leu Asp Lys Ser Ile Thr Leu Met His Arg Glu Ile Ser Ser Arg Leu
                        690                 695                 700

Lys Glu Ala Arg Asn Ser Val Lys Asp Leu Ile Ala Lys Ala Gln Val
        705                 710                 715                 720

Tyr Leu Thr Cys Gly Asp Gly Ser Arg Val Pro Pro Val Val Tyr
                        725                 730                 735

Met Tyr Gly Asp Ala Gly Cys Gly Lys Thr Glu Leu Ser Met Ala Leu
                        740                 745                 750

Gln Asp His Phe Ala Thr Lys Tyr Phe Gly Glu Val Pro Lys Lys Asp
                        755                 760                 765

Val Ile Tyr Ser Arg Lys Ala Glu Asn Glu Phe Trp Asp Gly Val Lys
        770                 775                 780

Gln Ser His Lys Ile Ile Ala Tyr Asp Asp Val Leu Gln Ile Val Asp
        785                 790                 795                 800

Ser Ala Gln Lys Pro Asn Pro Glu Leu Phe Glu Phe Ile Arg Leu Asn
                        805                 810                 815

Asn Ser Asp Pro Tyr Gln Val His Met Ser Ser Val Ser Asp Lys Ala
                        820                 825                 830

Asn Thr Phe Ile Ala Pro Ser Phe Val Phe Ala Thr Ser Asn Val Asn
                        835                 840                 845

Pro Gly Thr Tyr Val Pro Lys Ser Ile His Ser Ala Asp Ala Phe Arg
                        850                 855                 860

Arg Arg Leu Asp Leu Cys Val Tyr Val Asp Val Lys Asp Glu Phe Ala
        865                 870                 875                 880

Arg Ile Val Ala Gly Ser Lys Gly His Arg Lys Val Pro Cys Glu Gln
                        885                 890                 895
```

-continued

Lys Ile Trp Leu His Gln Asn Pro Gly Lys Thr Gln His Asp Met Lys
              900                 905                 910

His Glu Ile Val Ala Gly Thr Tyr Lys Ile Thr Pro Glu Thr Ala Val
              915                 920                 925

Tyr Glu Leu His Val Asp Thr Thr Leu Ala Gly Asp Ala Gln Ser Lys
              930                 935                 940

Val Cys Ala Tyr Asp Gly Leu Val Ser Leu Ile Glu Gln Val Arg Arg
945                 950                 955                 960

Leu Arg Val Ala Ala His Ser Asp Lys Val Glu Thr Asp Val Pro Val
              965                 970                 975

Leu Pro Thr Arg Leu His Glu Leu Ser Gln Glu Thr Phe Pro Asn Thr
              980                 985                 990

His Ala Gly Val Gly Phe Gln Phe Ala Thr Asp Trp Leu Gly Asp Phe
              995                 1000                1005

Asp Arg Pro Val Glu Ala Leu Ser Tyr Leu Asn Lys Thr Leu Glu
          1010              1015              1020

Ala His Phe Val Ser Arg Ser Ala Asn Asp Gly Ser Met Phe Ile
          1025              1030              1035

Pro Ala Ser Glu Val Ala Asp Leu Leu Cys Gln Arg His Asn Asn
          1040              1045              1050

Thr Asn Leu Asn Glu Glu Leu Val Tyr Leu Thr Trp Met Thr Gln
          1055              1060              1065

Ile Thr Asp Lys Glu Leu Ala Ser Ser Leu Val Tyr Phe Thr Asn
          1070              1075              1080

Asn Gly Met Asp Lys Ser Ile Trp Lys Lys Ser Ala Glu Arg Ser
          1085              1090              1095

Ala Gln Ala Ile Ser Gln Cys Lys Asn Ala Trp Thr Arg Ile Asn
          1100              1105              1110

Asp Phe Leu Lys Asn His Trp Ile Ser Ile Ser Ala Val Ile Gly
          1115              1120              1125

Ser Ala Leu Leu Ile Gly Gly Val Ser Ser Ala Val Lys Cys Ala
          1130              1135              1140

Thr Lys Cys Arg Val Arg Lys Ile Leu Gln Asp Gly Gly Ser Ile
          1145              1150              1155

Met Gln Leu Val Gly Val Arg Ser Cys Met Tyr Ala Cys Gln Leu
          1160              1165              1170

Cys Lys Arg Ile Lys Asn Cys Asp Leu Arg Leu Arg Val Arg Asn
          1175              1180              1185

Arg Ser Glu Gly Val Thr Thr Phe Val Pro Gly Asp Val Arg Arg
          1190              1195              1200

Val Ala Arg His Val Ile Ser Ala Ala Asp Val Cys Glu Val Pro
          1205              1210              1215

Val His His Ser Phe Ile Gln Ser Leu Cys Asp Glu Ala Phe Thr
          1220              1225              1230

Val His Ser Asp Lys Glu Glu Thr Phe Ser Ile Leu Asp Phe Thr
          1235              1240              1245

Pro Glu Ala Lys Gly Arg Asn Pro Pro Glu Ser Ala Val Val Glu
          1250              1255              1260

Ser His Gln Asp Tyr Arg Val Lys Ala Ala Val Glu Ser His
          1265              1270              1275

Gln Asp Phe Lys Pro Lys Asp Ala Ile Val Glu Ser Thr Ile Asp
          1280              1285              1290

```
Thr Val Phe Thr Glu Ser His Gln Asp Val Arg Val Lys Leu His
1295                1300                1305

Pro Gln Ile Glu Ser His Gln Asp Phe Arg Ala Lys Asn Pro Ile
1310                1315                1320

Val Glu Ser Arg Lys Pro Asp Tyr Gln Val Glu Trp Thr Asp Leu
1325                1330                1335

Arg Thr Glu Ser Ser Asn Asp Arg Asn Ala Gln Asp Ile Ser Asn
1340                1345                1350

Arg Ile Leu Ser Arg Asn Phe Val Arg Leu Tyr Val Pro Gly Ser
1355                1360                1365

Ser Leu Tyr Thr His Gly Leu Phe Ala Tyr Gly Arg Met Leu Leu
1370                1375                1380

Met Pro Lys His Met Phe Asp Met Leu Asn Gly Ser Val Glu Ile
1385                1390                1395

Val Ser Ile Ala Asp Lys Gly Asn Thr Arg Val His Val Lys Ile
1400                1405                1410

Gln Ser His Lys Thr Val Thr Arg Gly Gly Tyr Glu Val Asp Ile
1415                1420                1425

Val Ile Cys Glu Met Gly Asn Ser Ile Ser Ala Arg Lys Asp Ile
1430                1435                1440

Thr Ser Tyr Phe Pro Thr Val Lys Glu Leu Pro Gly Leu Thr Gly
1445                1450                1455

Met Met Ser Ser Gly Arg Met Arg Val Phe Ser Thr Ala Lys Phe
1460                1465                1470

Lys Ala Ser Asp Ser Cys Ser Tyr Leu Met Pro Gln Asp Phe Val
1475                1480                1485

Ala Lys Tyr Ile Ala Ala Val Asp His Ile Thr Ser Lys Ser Pro
1490                1495                1500

Glu Lys Lys Ser Tyr Phe Ile Arg Gln Gly Phe Glu Ala Glu Ser
1505                1510                1515

Asp Ser Met Gln Gly Asp Cys Cys Ser Pro Tyr Val Leu Phe Asn
1520                1525                1530

Ser Ala Ser Arg Ala Lys Ile Val Gly Leu His Cys Ala Gly Phe
1535                1540                1545

Asp Gly Thr Ala Arg Val Phe Ala Gln Ile Ile Thr Gln Glu Asp
1550                1555                1560

Ile Met Ala Ala Thr Pro Thr His Ala Gly Arg Val Thr Thr
1565                1570                1575

Glu Phe Pro His Thr Ser Leu Arg Asp Ser Pro Leu Pro Asn Ser
1580                1585                1590

Met Ala Ile Gly Ser Val Lys Thr Ala Pro Asn Pro Thr Lys Ser
1595                1600                1605

Glu Ile Thr Arg Ser Pro Ile His Gly Cys Phe Pro Val Arg Thr
1610                1615                1620

Ala Pro Ala Thr Leu Tyr Ser Pro Thr Glu Asn Leu Leu Ile Lys
1625                1630                1635

Asn Ala Met Lys Val Thr Lys Asn Val Glu Leu Leu Glu Glu Asp
1640                1645                1650

Leu Ile Asp Ala Cys Val His Asp Val Lys Arg Ile Leu Asn Ala
1655                1660                1665

Pro Gly Val Ser Asp Val Glu Lys Arg Val Leu Thr His Glu Glu
1670                1675                1680

Ser Ile Thr Gly Ile Glu Asn Arg Gln Tyr Met Asn Ala Leu Asn
```

```
            1685                1690                1695

Arg Ser Thr Ser Ala Gly Phe Pro Tyr Ser Ser Arg Lys Ala Lys
    1700                1705                1710

Gly Lys Ser Gly Lys Gln Thr Trp Leu Gly Ser Glu Glu Phe Ile
    1715                1720                1725

Val Asp Asn Pro Asp Leu Lys Glu His Val Glu Lys Ile Val Asp
    1730                1735                1740

Lys Ala Lys Asp Gly Ile Val Asp Val Ser Leu Gly Ile Phe Ala
    1745                1750                1755

Ala Thr Leu Lys Asp Glu Arg Arg Pro Leu Glu Lys Val Gln Ala
    1760                1765                1770

Asn Lys Thr Arg Val Phe Ala Ala Ser Asn Gln Gly Leu Ala Leu
    1775                1780                1785

Ala Leu Arg Arg Tyr Tyr Leu Ser Phe Leu Asp His Val Met Thr
    1790                1795                1800

Asn Arg Ile Asp Asn Glu Ile Gly Leu Gly Val Asn Val Tyr Ser
    1805                1810                1815

Tyr Asp Trp Thr Arg Ile Val Asn Lys Leu Lys Arg Val Gly Asp
    1820                1825                1830

Lys Val Ile Ala Gly Asp Phe Ser Asn Phe Asp Gly Ser Leu Asn
    1835                1840                1845

Ser Gln Ile Leu Ser Arg Val Ser Glu Ile Val Thr Asp Trp Tyr
    1850                1855                1860

Gly Asp Asp Ala Glu Asn Gly Leu Ile Arg His Thr Leu Leu Glu
    1865                1870                1875

Tyr Leu Phe Asn Ala Thr Trp Leu Met Asn Gly Lys Val Phe Gln
    1880                1885                1890

Leu Asn His Ser Gln Pro Ser Gly Asn Pro Leu Thr Thr Leu Ile
    1895                1900                1905

Asn Cys Val Tyr Asn Met Ile Ile Phe Arg Tyr Val Tyr Leu Leu
    1910                1915                1920

Ala Gln Arg Glu Asn Gly Phe Pro Met Thr Leu Ser Gly Phe Thr
    1925                1930                1935

Thr Asn Val Ala Cys Ile Phe Tyr Gly Asp Asp Ser Leu Cys Ser
    1940                1945                1950

Val Ser Asp Lys Val Ser Glu Trp Phe Asn Gln His Val Ile Thr
    1955                1960                1965

Arg Leu Met Ala Ala Thr Gly His Glu Tyr Thr Asp Glu Thr Lys
    1970                1975                1980

Ser Gly Ser Pro Pro Tyr Arg Ser Leu Asn Glu Val Thr Phe
    1985                1990                1995

Leu Lys Arg Glu Phe Val Leu Arg Asp His Phe Trp Ile Ala Pro
    2000                2005                2010

Leu Ser Arg Asn Thr Ile Glu Asp Met Cys Met Trp Ser Arg Lys
    2015                2020                2025

Asn Ile Asp Ala Gln Asp Ala Leu Leu Gln Thr Thr Arg Ile Ala
    2030                2035                2040

Ser Phe Glu Ala Ser Leu His Glu Lys Asn Tyr Phe Leu Met Phe
    2045                2050                2055

Cys Asp Val Ile Lys Lys Ala Cys Arg Asn Ala Gly Tyr Lys Glu
    2060                2065                2070

Ala Cys Leu His Glu Leu Asp Cys Lys Ser Phe Leu Leu Ala Gln
    2075                2080                2085
```

```
Gln Gly Arg Ala Gly Ala His Asp Ser Glu Phe Leu Ser Gln Leu
    2090            2095                2100

Leu Asp Leu Asn
    2105
```

<210> SEQ ID NO 114
<211> LENGTH: 44
<212> TYPE: PRT
<213> ORGANISM: Taura syndrome virus

<400> SEQUENCE: 114

```
His Arg Ala Phe Tyr Val Met Asn Asp Asp Gly Glu Asn Arg Ile Tyr
1               5                   10                  15

Ser Leu Ile Gly Thr Leu Arg Arg Ala Pro Ala Phe Lys Val Gly Ser
            20                  25                  30

Arg Arg Tyr Lys Ser His Ile Pro Tyr Arg Arg Lys
        35                  40
```

<210> SEQ ID NO 115
<211> LENGTH: 10
<212> TYPE: PRT
<213> ORGANISM: Taura syndrome virus

<400> SEQUENCE: 115

```
Lys Val Gly Ser Arg Arg Tyr Lys Ser His
1               5                   10
```

<210> SEQ ID NO 116
<211> LENGTH: 27
<212> TYPE: PRT
<213> ORGANISM: Taura syndrome virus

<400> SEQUENCE: 116

```
Lys Val Gly Ser Arg Arg Tyr Lys Ser His Ile Pro Tyr Arg Arg Lys
1               5                   10                  15

Ala Thr Val Ala Glu Leu Cys Asn Gln Leu His
            20                  25
```

<210> SEQ ID NO 117
<211> LENGTH: 9
<212> TYPE: PRT
<213> ORGANISM: Taura syndrome virus

<400> SEQUENCE: 117

```
Lys Ser His Ile Pro Tyr Arg Arg Lys
1               5
```

<210> SEQ ID NO 118
<211> LENGTH: 20
<212> TYPE: PRT
<213> ORGANISM: Taura syndrome virus

<400> SEQUENCE: 118

```
Lys Ser His Ile Pro Tyr Arg Arg Lys Ala Thr Val Ala Glu Leu Cys
1               5                   10                  15

Asn Gln Leu His
            20
```

<210> SEQ ID NO 119
<211> LENGTH: 38
<212> TYPE: PRT
<213> ORGANISM: Taura syndrome virus

```
<400> SEQUENCE: 119

His Ile Pro Tyr Arg Arg Lys Ala Thr Val Ala Glu Leu Cys Asn Gln
1               5                   10                  15

Leu His Asp Arg Val Leu Pro Phe Ala Asn Pro Gln Val Trp Lys Glu
            20                  25                  30

Val Ile Ser Glu Asn Lys
        35

<210> SEQ ID NO 120
<211> LENGTH: 46
<212> TYPE: PRT
<213> ORGANISM: Taura syndrome virus

<400> SEQUENCE: 120

His Ile Pro Tyr Arg Arg Lys Ala Thr Val Ala Glu Leu Cys Asn Gln
1               5                   10                  15

Leu His Asp Arg Val Leu Pro Phe Ala Asn Pro Gln Val Trp Lys Glu
            20                  25                  30

Val Ile Ser Glu Asn Lys Val Gln Pro Asp Ser Met Leu Lys
        35                  40                  45

<210> SEQ ID NO 121
<211> LENGTH: 29
<212> TYPE: PRT
<213> ORGANISM: Taura syndrome virus

<400> SEQUENCE: 121

His Asp Arg Val Leu Pro Phe Ala Asn Pro Gln Val Trp Lys Glu Val
1               5                   10                  15

Ile Ser Glu Asn Lys Val Gln Pro Asp Ser Met Leu Lys
            20                  25

<210> SEQ ID NO 122
<211> LENGTH: 21
<212> TYPE: PRT
<213> ORGANISM: Taura syndrome virus

<400> SEQUENCE: 122

His Asp Arg Val Leu Pro Phe Ala Asn Pro Gln Val Trp Lys Glu Val
1               5                   10                  15

Ile Ser Glu Asn Lys
            20

<210> SEQ ID NO 123
<211> LENGTH: 18
<212> TYPE: PRT
<213> ORGANISM: Taura syndrome virus

<400> SEQUENCE: 123

Lys Cys Asn Asp Cys Ile Leu Lys Met Asn Arg Asn Val Glu Tyr Pro
1               5                   10                  15

Tyr His

<210> SEQ ID NO 124
<211> LENGTH: 42
<212> TYPE: PRT
<213> ORGANISM: Taura syndrome virus

<400> SEQUENCE: 124

Lys Ile Ile Asp Leu Ile Lys Glu Thr Phe Val Ser Leu Phe Phe Ala
```

```
                1               5                  10                 15
        Ile Leu Thr Lys Ser Leu Tyr Pro Ile Ile Gln Gly Ile Ser Ser Tyr
                       20                  25                 30

Ala Leu Arg Asn Asn Leu Met Ala Asn His
                       35                  40

<210> SEQ ID NO 125
<211> LENGTH: 26
<212> TYPE: PRT
<213> ORGANISM: Taura syndrome virus

<400> SEQUENCE: 125

Lys Ser Arg Lys Asn Leu Asp Leu Leu Lys Glu Tyr Pro Ser Leu Asp
1               5                  10                 15

Ser Leu Leu Ser Ile Phe Asn Tyr Phe His
                20                  25

<210> SEQ ID NO 126
<211> LENGTH: 23
<212> TYPE: PRT
<213> ORGANISM: Taura syndrome virus

<400> SEQUENCE: 126

Lys Asn Leu Asp Leu Leu Lys Glu Tyr Pro Ser Leu Asp Ser Leu Leu
1               5                  10                 15

Ser Ile Phe Asn Tyr Phe His
                20

<210> SEQ ID NO 127
<211> LENGTH: 16
<212> TYPE: PRT
<213> ORGANISM: Taura syndrome virus

<400> SEQUENCE: 127

His Arg Glu Ile Ser Ser Arg Leu Lys Glu Ala Arg Asn Ser Val Lys
1               5                  10                 15

<210> SEQ ID NO 128
<211> LENGTH: 51
<212> TYPE: PRT
<213> ORGANISM: Taura syndrome virus

<400> SEQUENCE: 128

Lys Glu Ala Arg Asn Ser Val Lys Asp Leu Ile Ala Lys Ala Gln Val
1               5                  10                 15

Tyr Leu Thr Cys Gly Asp Gly Ser Arg Val Pro Pro Val Val Val Tyr
                20                  25                 30

Met Tyr Gly Asp Ala Gly Cys Gly Lys Thr Glu Leu Ser Met Ala Leu
                35                  40                 45

Gln Asp His
        50

<210> SEQ ID NO 129
<211> LENGTH: 12
<212> TYPE: PRT
<213> ORGANISM: Taura syndrome virus

<400> SEQUENCE: 129

His Phe Ala Thr Lys Tyr Phe Gly Glu Val Pro Lys
1               5                  10
```

```
<210> SEQ ID NO 130
<211> LENGTH: 13
<212> TYPE: PRT
<213> ORGANISM: Taura syndrome virus

<400> SEQUENCE: 130

His Phe Ala Thr Lys Tyr Phe Gly Glu Val Pro Lys Lys
1               5                   10

<210> SEQ ID NO 131
<211> LENGTH: 20
<212> TYPE: PRT
<213> ORGANISM: Taura syndrome virus

<400> SEQUENCE: 131

His Phe Ala Thr Lys Tyr Phe Gly Glu Val Pro Lys Lys Asp Val Ile
1               5                   10                  15

Tyr Ser Arg Lys
            20

<210> SEQ ID NO 132
<211> LENGTH: 30
<212> TYPE: PRT
<213> ORGANISM: Taura syndrome virus

<400> SEQUENCE: 132

His Phe Ala Thr Lys Tyr Phe Gly Glu Val Pro Lys Lys Asp Val Ile
1               5                   10                  15

Tyr Ser Arg Lys Ala Glu Asn Glu Phe Trp Asp Gly Val Lys
            20                  25                  30

<210> SEQ ID NO 133
<211> LENGTH: 29
<212> TYPE: PRT
<213> ORGANISM: Taura syndrome virus

<400> SEQUENCE: 133

Lys Tyr Phe Gly Glu Val Pro Lys Lys Asp Val Ile Tyr Ser Arg Lys
1               5                   10                  15

Ala Glu Asn Glu Phe Trp Asp Gly Val Lys Gln Ser His
            20                  25

<210> SEQ ID NO 134
<211> LENGTH: 22
<212> TYPE: PRT
<213> ORGANISM: Taura syndrome virus

<400> SEQUENCE: 134

Lys Lys Asp Val Ile Tyr Ser Arg Lys Ala Glu Asn Glu Phe Trp Asp
1               5                   10                  15

Gly Val Lys Gln Ser His
            20

<210> SEQ ID NO 135
<211> LENGTH: 21
<212> TYPE: PRT
<213> ORGANISM: Taura syndrome virus

<400> SEQUENCE: 135

Lys Asp Val Ile Tyr Ser Arg Lys Ala Glu Asn Glu Phe Trp Asp Gly
1               5                   10                  15

Val Lys Gln Ser His
            20
```

<210> SEQ ID NO 136
<211> LENGTH: 14
<212> TYPE: PRT
<213> ORGANISM: Taura syndrome virus

<400> SEQUENCE: 136

Lys Ala Glu Asn Glu Phe Trp Asp Gly Val Lys Gln Ser His
1               5                   10

<210> SEQ ID NO 137
<211> LENGTH: 51
<212> TYPE: PRT
<213> ORGANISM: Taura syndrome virus

<400> SEQUENCE: 137

Lys Ala Glu Asn Glu Phe Trp Asp Gly Val Lys Gln Ser His Lys Ile
1               5                   10                  15

Ile Ala Tyr Asp Asp Val Leu Gln Ile Val Asp Ser Ala Gln Lys Pro
            20                  25                  30

Asn Pro Glu Leu Phe Glu Phe Ile Arg Leu Asn Asn Ser Asp Pro Tyr
        35                  40                  45

Gln Val His
    50

<210> SEQ ID NO 138
<211> LENGTH: 49
<212> TYPE: PRT
<213> ORGANISM: Taura syndrome virus

<400> SEQUENCE: 138

His Ser Ala Asp Ala Phe Arg Arg Leu Asp Leu Cys Val Tyr Val
1               5                   10                  15

Asp Val Lys Asp Glu Phe Ala Arg Ile Val Ala Gly Ser Lys Gly His
            20                  25                  30

Arg Lys Val Pro Cys Glu Gln Lys Ile Trp Leu His Gln Asn Pro Gly
        35                  40                  45

Lys

<210> SEQ ID NO 139
<211> LENGTH: 40
<212> TYPE: PRT
<213> ORGANISM: Taura syndrome virus

<400> SEQUENCE: 139

His Ser Ala Asp Ala Phe Arg Arg Leu Asp Leu Cys Val Tyr Val
1               5                   10                  15

Asp Val Lys Asp Glu Phe Ala Arg Ile Val Ala Gly Ser Lys Gly His
            20                  25                  30

Arg Lys Val Pro Cys Glu Gln Lys
        35                  40

<210> SEQ ID NO 140
<211> LENGTH: 46
<212> TYPE: PRT
<213> ORGANISM: Taura syndrome virus

<400> SEQUENCE: 140

Lys Gly His Arg Lys Val Pro Cys Glu Gln Lys Ile Trp Leu His Gln
1               5                   10                  15

Asn Pro Gly Lys Thr Gln His Asp Met Lys His Glu Ile Val Ala Gly
            20                  25                  30

Thr Tyr Lys Ile Thr Pro Glu Thr Ala Val Tyr Glu Leu His
        35                  40                  45

<210> SEQ ID NO 141
<211> LENGTH: 15
<212> TYPE: PRT
<213> ORGANISM: Taura syndrome virus

<400> SEQUENCE: 141

Lys Gly His Arg Lys Val Pro Cys Glu Gln Lys Ile Trp Leu His
1               5                   10                  15

<210> SEQ ID NO 142
<211> LENGTH: 11
<212> TYPE: PRT
<213> ORGANISM: Taura syndrome virus

<400> SEQUENCE: 142

Lys Gly His Arg Lys Val Pro Cys Glu Gln Lys
1               5                   10

<210> SEQ ID NO 143
<211> LENGTH: 23
<212> TYPE: PRT
<213> ORGANISM: Taura syndrome virus

<400> SEQUENCE: 143

Lys Gly His Arg Lys Val Pro Cys Glu Gln Lys Ile Trp Leu His Gln
1               5                   10                  15

Asn Pro Gly Lys Thr Gln His
            20

<210> SEQ ID NO 144
<211> LENGTH: 27
<212> TYPE: PRT
<213> ORGANISM: Taura syndrome virus

<400> SEQUENCE: 144

Lys Gly His Arg Lys Val Pro Cys Glu Gln Lys Ile Trp Leu His Gln
1               5                   10                  15

Asn Pro Gly Lys Thr Gln His Asp Met Lys His
            20                  25

<210> SEQ ID NO 145
<211> LENGTH: 33
<212> TYPE: PRT
<213> ORGANISM: Taura syndrome virus

<400> SEQUENCE: 145

His Arg Lys Val Pro Cys Glu Gln Lys Ile Trp Leu His Gln Asn Pro
1               5                   10                  15

Gly Lys Thr Gln His Asp Met Lys His Glu Ile Val Ala Gly Thr Tyr
            20                  25                  30

Lys

<210> SEQ ID NO 146
<211> LENGTH: 18
<212> TYPE: PRT
<213> ORGANISM: Taura syndrome virus

<400> SEQUENCE: 146

-continued

His Arg Lys Val Pro Cys Glu Gln Lys Ile Trp Leu His Gln Asn Pro
1               5                   10                  15

Gly Lys

<210> SEQ ID NO 147
<211> LENGTH: 9
<212> TYPE: PRT
<213> ORGANISM: Taura syndrome virus

<400> SEQUENCE: 147

His Arg Lys Val Pro Cys Glu Gln Lys
1               5

<210> SEQ ID NO 148
<211> LENGTH: 24
<212> TYPE: PRT
<213> ORGANISM: Taura syndrome virus

<400> SEQUENCE: 148

His Arg Lys Val Pro Cys Glu Gln Lys Ile Trp Leu His Gln Asn Pro
1               5                   10                  15

Gly Lys Thr Gln His Asp Met Lys
            20

<210> SEQ ID NO 149
<211> LENGTH: 11
<212> TYPE: PRT
<213> ORGANISM: Taura syndrome virus

<400> SEQUENCE: 149

Lys Val Pro Cys Glu Gln Lys Ile Trp Leu His
1               5                   10

<210> SEQ ID NO 150
<211> LENGTH: 19
<212> TYPE: PRT
<213> ORGANISM: Taura syndrome virus

<400> SEQUENCE: 150

Lys Val Pro Cys Glu Gln Lys Ile Trp Leu His Gln Asn Pro Gly Lys
1               5                   10                  15

Thr Gln His

<210> SEQ ID NO 151
<211> LENGTH: 23
<212> TYPE: PRT
<213> ORGANISM: Taura syndrome virus

<400> SEQUENCE: 151

Lys Val Pro Cys Glu Gln Lys Ile Trp Leu His Gln Asn Pro Gly Lys
1               5                   10                  15

Thr Gln His Asp Met Lys His
            20

<210> SEQ ID NO 152
<211> LENGTH: 42
<212> TYPE: PRT
<213> ORGANISM: Taura syndrome virus

<400> SEQUENCE: 152

Lys Val Pro Cys Glu Gln Lys Ile Trp Leu His Gln Asn Pro Gly Lys
1               5                   10                  15

```
Thr Gln His Asp Met Lys His Glu Ile Val Ala Gly Thr Tyr Lys Ile
            20                  25                  30

Thr Pro Glu Thr Ala Val Tyr Glu Leu His
        35                  40

<210> SEQ ID NO 153
<211> LENGTH: 10
<212> TYPE: PRT
<213> ORGANISM: Taura syndrome virus

<400> SEQUENCE: 153

Lys Ile Trp Leu His Gln Asn Pro Gly Lys
1               5                   10

<210> SEQ ID NO 154
<211> LENGTH: 13
<212> TYPE: PRT
<213> ORGANISM: Taura syndrome virus

<400> SEQUENCE: 154

Lys Ile Trp Leu His Gln Asn Pro Gly Lys Thr Gln His
1               5                   10

<210> SEQ ID NO 155
<211> LENGTH: 17
<212> TYPE: PRT
<213> ORGANISM: Taura syndrome virus

<400> SEQUENCE: 155

Lys Ile Trp Leu His Gln Asn Pro Gly Lys Thr Gln His Asp Met Lys
1               5                   10                  15

His

<210> SEQ ID NO 156
<211> LENGTH: 36
<212> TYPE: PRT
<213> ORGANISM: Taura syndrome virus

<400> SEQUENCE: 156

Lys Ile Trp Leu His Gln Asn Pro Gly Lys Thr Gln His Asp Met Lys
1               5                   10                  15

His Glu Ile Val Ala Gly Thr Tyr Lys Ile Thr Pro Glu Thr Ala Val
            20                  25                  30

Tyr Glu Leu His
        35

<210> SEQ ID NO 157
<211> LENGTH: 12
<212> TYPE: PRT
<213> ORGANISM: Taura syndrome virus

<400> SEQUENCE: 157

His Gln Asn Pro Gly Lys Thr Gln His Asp Met Lys
1               5                   10

<210> SEQ ID NO 158
<211> LENGTH: 21
<212> TYPE: PRT
<213> ORGANISM: Taura syndrome virus

<400> SEQUENCE: 158

His Gln Asn Pro Gly Lys Thr Gln His Asp Met Lys His Glu Ile Val
```

```
                1               5                  10                 15
Ala Gly Thr Tyr Lys
            20

<210> SEQ ID NO 159
<211> LENGTH: 7
<212> TYPE: PRT
<213> ORGANISM: Taura syndrome virus

<400> SEQUENCE: 159

Lys Thr Gln His Asp Met Lys
1               5

<210> SEQ ID NO 160
<211> LENGTH: 8
<212> TYPE: PRT
<213> ORGANISM: Taura syndrome virus

<400> SEQUENCE: 160

Lys Thr Gln His Asp Met Lys His
1               5

<210> SEQ ID NO 161
<211> LENGTH: 27
<212> TYPE: PRT
<213> ORGANISM: Taura syndrome virus

<400> SEQUENCE: 161

Lys Thr Gln His Asp Met Lys His Glu Ile Val Ala Gly Thr Tyr Lys
1               5                  10                 15

Ile Thr Pro Glu Thr Ala Val Tyr Glu Leu His
            20                  25

<210> SEQ ID NO 162
<211> LENGTH: 13
<212> TYPE: PRT
<213> ORGANISM: Taura syndrome virus

<400> SEQUENCE: 162

His Asp Met Lys His Glu Ile Val Ala Gly Thr Tyr Lys
1               5                  10

<210> SEQ ID NO 163
<211> LENGTH: 10
<212> TYPE: PRT
<213> ORGANISM: Taura syndrome virus

<400> SEQUENCE: 163

Lys His Glu Ile Val Ala Gly Thr Tyr Lys
1               5                  10

<210> SEQ ID NO 164
<211> LENGTH: 21
<212> TYPE: PRT
<213> ORGANISM: Taura syndrome virus

<400> SEQUENCE: 164

Lys His Glu Ile Val Ala Gly Thr Tyr Lys Ile Thr Pro Glu Thr Ala
1               5                  10                 15

Val Tyr Glu Leu His
            20

<210> SEQ ID NO 165
```

```
<211> LENGTH: 32
<212> TYPE: PRT
<213> ORGANISM: Taura syndrome virus

<400> SEQUENCE: 165

His Trp Ile Ser Ile Ser Ala Val Ile Gly Ser Ala Leu Leu Ile Gly
1               5                   10                  15

Gly Val Ser Ser Ala Val Lys Cys Ala Thr Lys Cys Arg Val Arg Lys
            20                  25                  30

<210> SEQ ID NO 166
<211> LENGTH: 51
<212> TYPE: PRT
<213> ORGANISM: Taura syndrome virus

<400> SEQUENCE: 166

His Gln Asp Phe Lys Pro Lys Asp Ala Ile Val Glu Ser Thr Ile Asp
1               5                   10                  15

Thr Val Phe Thr Glu Ser His Gln Asp Val Arg Val Lys Leu His Pro
            20                  25                  30

Gln Ile Glu Ser His Gln Asp Phe Arg Ala Lys Asn Pro Ile Val Glu
        35                  40                  45

Ser Arg Lys
        50

<210> SEQ ID NO 167
<211> LENGTH: 29
<212> TYPE: PRT
<213> ORGANISM: Taura syndrome virus

<400> SEQUENCE: 167

His Gln Asp Val Arg Val Lys Leu His Pro Gln Ile Glu Ser His Gln
1               5                   10                  15

Asp Phe Arg Ala Lys Asn Pro Ile Val Glu Ser Arg Lys
            20                  25

<210> SEQ ID NO 168
<211> LENGTH: 21
<212> TYPE: PRT
<213> ORGANISM: Taura syndrome virus

<400> SEQUENCE: 168

His Pro Gln Ile Glu Ser His Gln Asp Phe Arg Ala Lys Asn Pro Ile
1               5                   10                  15

Val Glu Ser Arg Lys
            20

<210> SEQ ID NO 169
<211> LENGTH: 15
<212> TYPE: PRT
<213> ORGANISM: Taura syndrome virus

<400> SEQUENCE: 169

His Gln Asp Phe Arg Ala Lys Asn Pro Ile Val Glu Ser Arg Lys
1               5                   10                  15

<210> SEQ ID NO 170
<211> LENGTH: 40
<212> TYPE: PRT
<213> ORGANISM: Taura syndrome virus

<400> SEQUENCE: 170
```

```
His Gly Leu Phe Ala Tyr Gly Arg Met Leu Met Pro Lys His Met
1               5                   10                  15

Phe Asp Met Leu Asn Gly Ser Val Glu Ile Val Ser Ile Ala Asp Lys
            20                  25                  30

Gly Asn Thr Arg Val His Val Lys
        35                  40

<210> SEQ ID NO 171
<211> LENGTH: 26
<212> TYPE: PRT
<213> ORGANISM: Taura syndrome virus

<400> SEQUENCE: 171

His Met Phe Asp Met Leu Asn Gly Ser Val Glu Ile Val Ser Ile Ala
1               5                   10                  15

Asp Lys Gly Asn Thr Arg Val His Val Lys
            20                  25

<210> SEQ ID NO 172
<211> LENGTH: 9
<212> TYPE: PRT
<213> ORGANISM: Taura syndrome virus

<400> SEQUENCE: 172

Lys Gly Asn Thr Arg Val His Val Lys
1               5

<210> SEQ ID NO 173
<211> LENGTH: 13
<212> TYPE: PRT
<213> ORGANISM: Taura syndrome virus

<400> SEQUENCE: 173

Lys Gly Asn Thr Arg Val His Val Lys Ile Gln Ser His
1               5                   10

<210> SEQ ID NO 174
<211> LENGTH: 42
<212> TYPE: PRT
<213> ORGANISM: Taura syndrome virus

<400> SEQUENCE: 174

His Val Lys Ile Gln Ser His Lys Thr Val Thr Arg Gly Gly Tyr Glu
1               5                   10                  15

Val Asp Ile Val Ile Cys Glu Met Gly Asn Ser Ile Ser Ala Arg Lys
            20                  25                  30

Asp Ile Thr Ser Tyr Phe Pro Thr Val Lys
        35                  40

<210> SEQ ID NO 175
<211> LENGTH: 36
<212> TYPE: PRT
<213> ORGANISM: Taura syndrome virus

<400> SEQUENCE: 175

His Lys Thr Val Thr Arg Gly Gly Tyr Glu Val Asp Ile Val Ile Cys
1               5                   10                  15

Glu Met Gly Asn Ser Ile Ser Ala Arg Lys Asp Ile Thr Ser Tyr Phe
            20                  25                  30

Pro Thr Val Lys
        35
```

<210> SEQ ID NO 176
<211> LENGTH: 26
<212> TYPE: PRT
<213> ORGANISM: Taura syndrome virus

<400> SEQUENCE: 176

His Thr Ser Leu Arg Asp Ser Pro Leu Pro Asn Ser Met Ala Ile Gly
1               5                   10                  15

Ser Val Lys Thr Ala Pro Asn Pro Thr Lys
            20                  25

<210> SEQ ID NO 177
<211> LENGTH: 17
<212> TYPE: PRT
<213> ORGANISM: Taura syndrome virus

<400> SEQUENCE: 177

Lys Thr Ala Pro Asn Pro Thr Lys Ser Glu Ile Thr Arg Ser Pro Ile
1               5                   10                  15

His

<210> SEQ ID NO 178
<211> LENGTH: 30
<212> TYPE: PRT
<213> ORGANISM: Taura syndrome virus

<400> SEQUENCE: 178

His Gly Cys Phe Pro Val Arg Thr Ala Pro Ala Thr Leu Tyr Ser Pro
1               5                   10                  15

Thr Glu Asn Leu Leu Ile Lys Asn Ala Met Lys Val Thr Lys
            20                  25                  30

<210> SEQ ID NO 179
<211> LENGTH: 23
<212> TYPE: PRT
<213> ORGANISM: Taura syndrome virus

<400> SEQUENCE: 179

Lys Asn Ala Met Lys Val Thr Lys Asn Val Glu Leu Leu Glu Glu Asp
1               5                   10                  15

Leu Ile Asp Ala Cys Val His
            20

<210> SEQ ID NO 180
<211> LENGTH: 44
<212> TYPE: PRT
<213> ORGANISM: Taura syndrome virus

<400> SEQUENCE: 180

Lys Asn Ala Met Lys Val Thr Lys Asn Val Glu Leu Leu Glu Glu Asp
1               5                   10                  15

Leu Ile Asp Ala Cys Val His Asp Val Lys Arg Ile Leu Asn Ala Pro
            20                  25                  30

Gly Val Ser Asp Val Glu Lys Arg Val Leu Thr His
            35                  40

<210> SEQ ID NO 181
<211> LENGTH: 38
<212> TYPE: PRT
<213> ORGANISM: Taura syndrome virus

<400> SEQUENCE: 181

His Glu Glu Ser Ile Thr Gly Ile Glu Asn Arg Gln Tyr Met Asn Ala
1               5                   10                  15

Leu Asn Arg Ser Thr Ser Ala Gly Phe Pro Tyr Ser Arg Lys Ala
            20                  25                  30

Lys Gly Lys Ser Gly Lys
            35

<210> SEQ ID NO 182
<211> LENGTH: 27
<212> TYPE: PRT
<213> ORGANISM: Taura syndrome virus

<400> SEQUENCE: 182

Lys Ala Lys Gly Lys Ser Gly Lys Gln Thr Trp Leu Gly Ser Glu Glu
1               5                   10                  15

Phe Ile Val Asp Asn Pro Asp Leu Lys Glu His
            20                  25

<210> SEQ ID NO 183
<211> LENGTH: 10
<212> TYPE: PRT
<213> ORGANISM: Taura syndrome virus

<400> SEQUENCE: 183

Lys Glu His Val Glu Lys Ile Val Asp Lys
1               5                   10

<210> SEQ ID NO 184
<211> LENGTH: 34
<212> TYPE: PRT
<213> ORGANISM: Taura syndrome virus

<400> SEQUENCE: 184

His Val Glu Lys Ile Val Asp Lys Ala Lys Asp Gly Ile Val Asp Val
1               5                   10                  15

Ser Leu Gly Ile Phe Ala Ala Thr Leu Lys Asp Glu Arg Arg Pro Leu
            20                  25                  30

Glu Lys

<210> SEQ ID NO 185
<211> LENGTH: 10
<212> TYPE: PRT
<213> ORGANISM: Taura syndrome virus

<400> SEQUENCE: 185

His Val Glu Lys Ile Val Asp Lys Ala Lys
1               5                   10

<210> SEQ ID NO 186
<211> LENGTH: 39
<212> TYPE: PRT
<213> ORGANISM: Taura syndrome virus

<400> SEQUENCE: 186

Lys Asp Glu Arg Arg Pro Leu Glu Lys Val Gln Ala Asn Lys Thr Arg
1               5                   10                  15

Val Phe Ala Ala Ser Asn Gln Gly Leu Ala Leu Ala Leu Arg Arg Tyr
            20                  25                  30

Tyr Leu Ser Phe Leu Asp His
            35

<210> SEQ ID NO 187
<211> LENGTH: 35
<212> TYPE: PRT
<213> ORGANISM: Taura syndrome virus

<400> SEQUENCE: 187

His Val Met Thr Asn Arg Ile Asp Asn Glu Ile Gly Leu Gly Val Asn
1               5                   10                  15

Val Tyr Ser Tyr Asp Trp Thr Arg Ile Val Asn Lys Leu Lys Arg Val
            20                  25                  30

Gly Asp Lys
        35

<210> SEQ ID NO 188
<211> LENGTH: 48
<212> TYPE: PRT
<213> ORGANISM: Taura syndrome virus

<400> SEQUENCE: 188

Lys Leu Lys Arg Val Gly Asp Lys Val Ile Ala Gly Asp Phe Ser Asn
1               5                   10                  15

Phe Asp Gly Ser Leu Asn Ser Gln Ile Leu Ser Arg Val Ser Glu Ile
            20                  25                  30

Val Thr Asp Trp Tyr Gly Asp Asp Ala Glu Asn Gly Leu Ile Arg His
        35                  40                  45

<210> SEQ ID NO 189
<211> LENGTH: 23
<212> TYPE: PRT
<213> ORGANISM: Taura syndrome virus

<400> SEQUENCE: 189

His Glu Lys Asn Tyr Phe Leu Met Phe Cys Asp Val Ile Lys Lys Ala
1               5                   10                  15

Cys Arg Asn Ala Gly Tyr Lys
            20

<210> SEQ ID NO 190
<211> LENGTH: 33
<212> TYPE: PRT
<213> ORGANISM: Taura syndrome virus

<400> SEQUENCE: 190

His Glu Lys Asn Tyr Phe Leu Met Phe Cys Asp Val Ile Lys Lys Ala
1               5                   10                  15

Cys Arg Asn Ala Gly Tyr Lys Glu Ala Cys Leu His Glu Leu Asp Cys
            20                  25                  30

Lys

<210> SEQ ID NO 191
<211> LENGTH: 15
<212> TYPE: PRT
<213> ORGANISM: Taura syndrome virus

<400> SEQUENCE: 191

Lys Lys Ala Cys Arg Asn Ala Gly Tyr Lys Glu Ala Cys Leu His
1               5                   10                  15

<210> SEQ ID NO 192
<211> LENGTH: 33
<212> TYPE: PRT

-continued

<213> ORGANISM: Taura syndrome virus

<400> SEQUENCE: 192

Lys Lys Ala Cys Arg Asn Ala Gly Tyr Lys Glu Ala Cys Leu His Glu
1               5                   10                  15

Leu Asp Cys Lys Ser Phe Leu Leu Ala Gln Gln Gly Arg Ala Gly Ala
            20                  25                  30

His

<210> SEQ ID NO 193
<211> LENGTH: 32
<212> TYPE: PRT
<213> ORGANISM: Taura syndrome virus

<400> SEQUENCE: 193

Lys Ala Cys Arg Asn Ala Gly Tyr Lys Glu Ala Cys Leu His Glu Leu
1               5                   10                  15

Asp Cys Lys Ser Phe Leu Leu Ala Gln Gln Gly Arg Ala Gly Ala His
            20                  25                  30

<210> SEQ ID NO 194
<211> LENGTH: 14
<212> TYPE: PRT
<213> ORGANISM: Taura syndrome virus

<400> SEQUENCE: 194

Lys Ala Cys Arg Asn Ala Gly Tyr Lys Glu Ala Cys Leu His
1               5                   10

<210> SEQ ID NO 195
<211> LENGTH: 11
<212> TYPE: PRT
<213> ORGANISM: Taura syndrome virus

<400> SEQUENCE: 195

Lys Glu Ala Cys Leu His Glu Leu Asp Cys Lys
1               5                   10

<210> SEQ ID NO 196
<211> LENGTH: 24
<212> TYPE: PRT
<213> ORGANISM: Taura syndrome virus

<400> SEQUENCE: 196

Lys Glu Ala Cys Leu His Glu Leu Asp Cys Lys Ser Phe Leu Leu Ala
1               5                   10                  15

Gln Gln Gly Arg Ala Gly Ala His
            20

<210> SEQ ID NO 197
<211> LENGTH: 32
<212> TYPE: PRT
<213> ORGANISM: Taura syndrome virus

<400> SEQUENCE: 197

Lys Lys Val Gln Ala Asn Lys Thr Arg Val Phe Ala Ala Ser Asn Gln
1               5                   10                  15

Gly Leu Ala Leu Ala Leu Arg Arg Tyr Tyr Leu Ser Phe Leu Asp His
            20                  25                  30

<210> SEQ ID NO 198
<211> LENGTH: 33

```
<212> TYPE: PRT
<213> ORGANISM: Taura syndrome virus

<400> SEQUENCE: 198

Lys Lys Ala Cys Arg Asn Ala Gly Tyr Lys Glu Ala Cys Leu His Glu
1               5                   10                  15

Leu Asp Cys Lys Ser Phe Leu Leu Ala Gln Gln Gly Arg Ala Gly Ala
            20                  25                  30

His

<210> SEQ ID NO 199
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Lys Ile Ile Gln Lys Ala His Lys
1               5

<210> SEQ ID NO 200
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

His Leu Lys Cys Arg Val Lys Met Glu Lys
1               5                   10

<210> SEQ ID NO 201
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Lys Leu Thr Ser Gly His Leu Lys
1               5

<210> SEQ ID NO 202
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

His Asn Asp Lys Arg Ala Asp Pro Ala Phe Val Cys Lys
1               5                   10
```

-continued

```
<210> SEQ ID NO 203
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Lys Lys Lys Lys Lys His Lys
1               5
```